United States Patent
Joerg et al.

(10) Patent No.: US 12,296,008 B2
(45) Date of Patent: *May 13, 2025

(54) PHARMACEUTICAL PRODUCTS AND STABLE LIQUID COMPOSITIONS OF IL-17 ANTIBODIES

(71) Applicant: NOVARTIS AG, Basel (CH)

(72) Inventors: Susanne Joerg, Binningen (CH); Kathrin Serno-Schersch, Basel (CH)

(73) Assignee: NOVARTIS AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 18/823,573

(22) Filed: Sep. 3, 2024

(65) Prior Publication Data

US 2024/0415961 A1    Dec. 19, 2024

Related U.S. Application Data

(60) Continuation of application No. 18/481,213, filed on Oct. 4, 2023, which is a division of application No. 15/538,257, filed as application No. PCT/IB2015/059836 on Dec. 21, 2015, now Pat. No. 11,801,300.

(60) Provisional application No. 62/095,210, filed on Dec. 22, 2014.

(51) Int. Cl.
    *A61K 39/395* (2006.01)
    *C07K 16/24* (2006.01)

(52) U.S. Cl.
    CPC ...... *A61K 39/39591* (2013.01); *C07K 16/244* (2013.01); *C07K 2317/21* (2013.01)

(58) Field of Classification Search
    CPC .................. A61K 39/39591; C07K 16/244
    See application file for complete search history.

(56) References Cited

U.S. PATENT DOCUMENTS

| | | | |
|---|---|---|---|
| 5,250,442 A | 10/1993 | Cabezas | |
| 5,272,135 A | 12/1993 | Harun et al. | |
| 6,309,636 B1 | 10/2001 | do Couto et al. | |
| 8,119,131 B2 | 2/2012 | Di Padova et al. | |
| 8,568,720 B2 | 10/2013 | Morichika | |
| 9,717,791 B2 | 8/2017 | Guettner et al. | |
| 9,744,234 B2 | 8/2017 | Mpofu et al. | |
| 11,280,479 B2 | 3/2022 | Meyer et al. | |
| 2001/0055617 A1 | 12/2001 | Mattern | |
| 2002/0052422 A1 | 5/2002 | Milstein | |
| 2002/0081302 A1 | 6/2002 | Cvitkovitch | |
| 2003/0012817 A1 | 1/2003 | Milstein | |
| 2003/0104996 A1 | 6/2003 | Tiansheng et al. | |
| 2004/0033228 A1* | 2/2004 | Krause ................... A61P 31/12 424/145.1 | |
| 2004/0038878 A1 | 2/2004 | Tanikawa et al. | |
| 2005/0147609 A1 | 7/2005 | Filvaroff | |
| 2007/0212362 A1 | 9/2007 | Filvaroff | |
| 2008/0044423 A1 | 2/2008 | Cochrane et al. | |
| 2008/0286280 A1 | 11/2008 | Kallmeyer | |
| 2009/0136491 A1 | 5/2009 | Chen | |
| 2010/0080812 A1 | 4/2010 | Auer | |
| 2010/0092566 A1 | 4/2010 | Alessi | |
| 2010/0266496 A1 | 10/2010 | Hansen | |
| 2010/0266608 A1 | 10/2010 | Cooreman et al. | |
| 2010/0272636 A1 | 10/2010 | Byrd | |
| 2010/0285011 A1* | 11/2010 | Morichika ............... A61P 37/02 424/133.1 | |
| 2011/0263828 A1 | 10/2011 | Wong | |
| 2012/0045848 A1 | 2/2012 | Haugland et al. | |
| 2012/0100068 A1 | 4/2012 | Byrd | |
| 2012/0183531 A1 | 7/2012 | Lucas et al. | |
| 2013/0017191 A1 | 1/2013 | Werner et al. | |
| 2013/0202610 A1 | 8/2013 | Guettner et al. | |
| 2013/0209480 A1 | 8/2013 | Mpofu et al. | |
| 2018/0008706 A1 | 1/2018 | Mpofu et al. | |

FOREIGN PATENT DOCUMENTS

| | | |
|---|---|---|
| CN | 104011223 A | 8/2014 |
| CN | 104244979 A | 12/2014 |
| EP | 0734728 A1 | 10/1996 |
| EP | 0734729 A1 | 10/1996 |
| EP | 0734730 A1 | 10/1996 |
| EP | 2796429 A1 | 10/2014 |
| EP | 3111954 A1 | 1/2017 |
| JP | 2000186046 A | 7/2000 |
| JP | 2000186048 A | 7/2000 |

(Continued)

OTHER PUBLICATIONS

ACR Call for Late-Breaking Abstracts, Guidelines for Submission, Nov. 10-14, 2022.
ACR/ARHP Call for abstracts Guidelines, Oct. 2010.
Aletaha, et al., 2010 Rheumatoid arthritis classification criteria: an American College of Rheumatology/European League Against Rheumatism collaborative initiative, Annals of Rheumatic Diseases, 69, 1580-1588, 2010.
Amgen Wyeth Press Release, Jul. 24, 2003, ENBREL Is First Biologic to Receive FDA Approval for the Treatment of Ankylosing Spondylitis.
Anonymous: ""Object"—Definition & Meaning—Merriam-Webster", , Dec. 8, 2021 (Dec. 8, 2021), pp. 1-15, XP055870736, Retrieved from the Internet: URL:https://www.merriam-webster.com/dictionary/object [retrieved on Dec. 8, 2021.

(Continued)

*Primary Examiner* — Vanessa L. Ford
*Assistant Examiner* — Sandra Carter
(74) *Attorney, Agent, or Firm* — David Goetz

(57) ABSTRACT

The disclosure is directed to pharmaceutical products and stable liquid compositions of IL-17 antibodies and antigen-binding fragments thereof, e.g., AIN457 (secukinumab), and processes of making these pharmaceutical products and compositions. The disclosure is also directed to the use of these pharmaceutical products and liquid compositions (e.g., as part of a kit having instructions for use) for the treatment of various IL-17-mediated disorders (e.g., autoimmune disorders, such as psoriasis, ankylosing spondylitis, psoriatic arthritis, and rheumatoid arthritis).

38 Claims, 18 Drawing Sheets

Specification includes a Sequence Listing.

(56) References Cited

FOREIGN PATENT DOCUMENTS

| | | |
|---|---|---|
| JP | 2015519311 A | 7/2015 |
| WO | 8700196 A1 | 1/1987 |
| WO | 9423767 A1 | 10/1994 |
| WO | 9533488 A1 | 12/1995 |
| WO | 9632096 A1 | 10/1996 |
| WO | 9704801 A1 | 2/1997 |
| WO | 0045790 A2 | 8/2000 |
| WO | 0056772 A1 | 9/2000 |
| WO | 0069463 A1 | 11/2000 |
| WO | 0124814 A1 | 4/2001 |
| WO | 0185137 A2 | 11/2001 |
| WO | 0202642 A2 | 1/2002 |
| WO | 03020299 A1 | 3/2003 |
| WO | 03039467 A2 | 5/2003 |
| WO | 03039485 A2 | 5/2003 |
| WO | 03087335 A2 | 10/2003 |
| WO | 2004007520 A2 | 1/2004 |
| WO | 2004055164 A2 | 7/2004 |
| WO | 2004058156 A2 | 7/2004 |
| WO | 2004060343 A1 | 7/2004 |
| WO | 2004110498 A2 | 12/2004 |
| WO | 2005010044 A2 | 2/2005 |
| WO | 2005049078 A2 | 6/2005 |
| WO | 2005058365 A1 | 6/2005 |
| WO | 2005063291 A1 | 7/2005 |
| WO | 2005077414 A1 | 8/2005 |
| WO | 2006013107 A1 | 2/2006 |
| WO | 2006039704 A2 | 4/2006 |
| WO | 2006044908 A2 | 4/2006 |
| WO | 2006054059 A1 | 5/2006 |
| WO | 2006063864 A2 | 6/2006 |
| WO | 2006063865 A2 | 6/2006 |
| WO | 2006081587 A2 | 8/2006 |
| WO | 2006083689 A2 | 8/2006 |
| WO | 2006088833 A2 | 8/2006 |
| WO | 2006088925 A2 | 8/2006 |
| WO | 2006096011 A1 | 9/2006 |
| WO | 2006096488 A2 | 9/2006 |
| WO | 2006096491 A2 | 9/2006 |
| WO | 2006138181 A2 | 12/2006 |
| WO | 2007002543 A2 | 1/2007 |
| WO | 2007027761 A2 | 3/2007 |
| WO | 2007036745 A2 | 4/2007 |
| WO | 2007059188 A1 | 5/2007 |
| WO | 2007070750 A1 | 6/2007 |
| WO | 2007076062 A2 | 7/2007 |
| WO | 2007092829 A2 | 8/2007 |
| WO | 2007095288 A2 | 8/2007 |
| WO | 2007095337 A2 | 8/2007 |
| WO | 2007106769 A2 | 9/2007 |
| WO | 2007109221 A2 | 9/2007 |
| WO | 2007110339 A1 | 10/2007 |
| WO | 2007117749 A2 | 10/2007 |
| WO | 2007124299 A2 | 11/2007 |
| WO | 2007143701 A2 | 12/2007 |
| WO | 2007147019 A2 | 12/2007 |
| WO | 2007149032 A1 | 12/2007 |
| WO | 2007149814 A1 | 12/2007 |
| WO | 2008011571 A1 | 1/2008 |
| WO | 2008021156 A2 | 2/2008 |
| WO | 2008029908 A1 | 3/2008 |
| WO | 2008030611 A2 | 3/2008 |
| WO | 2008047134 A2 | 4/2008 |
| WO | 2008051363 A2 | 5/2008 |
| WO | 2008054603 A2 | 5/2008 |
| WO | 2008065304 A1 | 6/2008 |
| WO | 2008067223 A2 | 6/2008 |
| WO | 2008071394 A1 | 6/2008 |
| WO | 2008071751 A1 | 6/2008 |
| WO | 2008079359 A2 | 7/2008 |
| WO | 2008079890 A1 | 7/2008 |
| WO | 2008086395 A2 | 7/2008 |
| WO | 2008087329 A2 | 7/2008 |
| WO | 2008121615 A2 | 10/2008 |
| WO | 2008121865 A1 | 10/2008 |
| WO | 2008132439 A2 | 11/2008 |
| WO | 2008134659 A2 | 11/2008 |
| WO | 2008149143 A2 | 12/2008 |
| WO | 2008149144 A2 | 12/2008 |
| WO | 2008149146 A2 | 12/2008 |
| WO | 2008149147 A2 | 12/2008 |
| WO | 2008149148 A2 | 12/2008 |
| WO | 2008149149 A2 | 12/2008 |
| WO | 2008149150 A2 | 12/2008 |
| WO | 2008150479 A2 | 12/2008 |
| WO | 2008156865 A2 | 12/2008 |
| WO | 2009003096 A2 | 12/2008 |
| WO | 2009006301 A2 | 1/2009 |
| WO | 2009007272 A1 | 1/2009 |
| WO | 2009015063 A2 | 1/2009 |
| WO | 2009025763 A2 | 2/2009 |
| WO | 2009037190 A2 | 3/2009 |
| WO | 2009055343 A2 | 4/2009 |
| WO | 2009064838 A1 | 5/2009 |
| WO | 2009074634 A2 | 6/2009 |
| WO | 2009080541 A1 | 7/2009 |
| WO | 2009084659 A1 | 7/2009 |
| WO | 2009089036 A2 | 7/2009 |
| WO | 2009100297 A1 | 8/2009 |
| WO | 2009130459 A2 | 10/2009 |
| WO | 2009133103 A1 | 11/2009 |
| WO | 2009141239 A1 | 11/2009 |
| WO | 2009149168 A2 | 12/2009 |
| WO | 2009149189 A2 | 12/2009 |
| WO | 2010006060 A2 | 1/2010 |
| WO | 2010017296 A1 | 2/2010 |
| WO | 2010025400 A2 | 3/2010 |
| WO | 2010030670 A2 | 3/2010 |
| WO | 2010032220 A1 | 3/2010 |
| WO | 2009136286 A9 | 4/2010 |
| WO | 2010034443 A1 | 4/2010 |
| WO | 2010042705 A1 | 4/2010 |
| WO | 2010056804 A1 | 5/2010 |
| WO | 2010060768 A1 | 6/2010 |
| WO | 2010062858 A1 | 6/2010 |
| WO | 2010062896 A1 | 6/2010 |
| WO | 2010065491 A2 | 6/2010 |
| WO | 2010066762 A1 | 6/2010 |
| WO | 2010069858 A1 | 6/2010 |
| WO | 2010081091 A2 | 7/2010 |
| WO | 2010091637 A1 | 8/2010 |
| WO | 2010100179 A2 | 9/2010 |
| WO | 2010102241 A1 | 9/2010 |
| WO | 2010102251 A2 | 9/2010 |
| WO | 2010114859 A1 | 10/2010 |
| WO | 2010123798 A2 | 10/2010 |
| WO | 2010124009 A2 | 10/2010 |
| WO | 2010128407 A2 | 11/2010 |
| WO | 2010148337 A1 | 12/2010 |
| WO | 2011005354 A2 | 1/2011 |
| WO | 2011008770 A1 | 1/2011 |
| WO | 2011012637 A2 | 2/2011 |
| WO | 2011023685 A1 | 3/2011 |
| WO | 2011028961 A2 | 3/2011 |
| WO | 2011028962 A1 | 3/2011 |
| WO | 2011029892 A2 | 3/2011 |
| WO | 2011034604 A2 | 3/2011 |
| WO | 2011044563 A2 | 4/2011 |
| WO | 2011053763 A2 | 5/2011 |
| WO | 2011076702 A1 | 6/2011 |
| WO | 2011080209 A2 | 7/2011 |
| WO | 2011096438 A1 | 8/2011 |
| WO | 2011104315 A2 | 9/2011 |
| WO | 2011112669 A1 | 9/2011 |
| WO | 2011139718 A1 | 11/2011 |
| WO | 2011141823 A2 | 11/2011 |
| WO | 2011161226 A2 | 12/2011 |
| WO | 2011163452 A2 | 12/2011 |
| WO | 2012018767 A2 | 2/2012 |
| WO | 2012028683 A1 | 3/2012 |
| WO | 2012045848 A1 | 4/2012 |
| WO | 2012064627 A2 | 5/2012 |
| WO | WO-2012059598 A2 * | 5/2012 ........... A61K 31/519 |

(56) References Cited

FOREIGN PATENT DOCUMENTS

| | | |
|---|---|---|
| WO | 2012082573 A1 | 6/2012 |
| WO | 2012094623 A2 | 7/2012 |
| WO | 2012095662 A1 | 7/2012 |
| WO | 2011088120 A9 | 8/2012 |
| WO | 2012103345 A1 | 8/2012 |
| WO | 2012121754 A1 | 9/2012 |
| WO | 2012151199 A1 | 11/2012 |
| WO | 2012154999 A1 | 11/2012 |
| WO | 2013057241 A1 | 4/2013 |
| WO | 2013063510 A1 | 5/2013 |
| WO | 2013077907 A1 | 5/2013 |
| WO | 2013083497 A1 | 6/2013 |
| WO | 2013087911 A1 | 6/2013 |
| WO | 2013087912 A1 | 6/2013 |
| WO | 2013087913 A1 | 6/2013 |
| WO | 2013087914 A1 | 6/2013 |
| WO | 2012156219 A9 | 7/2013 |
| WO | 2013134052 A1 | 9/2013 |
| WO | 2013158821 A2 | 10/2013 |
| WO | 2013164789 A2 | 11/2013 |
| WO | 2013164837 A1 | 11/2013 |
| WO | 2013186236 A1 | 12/2013 |
| WO | 2014001368 A1 | 1/2014 |
| WO | 2014036071 A1 | 3/2014 |
| WO | 2014036076 A1 | 3/2014 |
| WO | 2014044758 A1 | 3/2014 |
| WO | 2014076321 A1 | 5/2014 |
| WO | 2014085305 A1 | 6/2014 |
| WO | 2014090888 A1 | 6/2014 |
| WO | 2014096672 A1 | 6/2014 |
| WO | 2014122613 A1 | 8/2014 |
| WO | 2014141152 A2 | 9/2014 |
| WO | 2014143909 A1 | 9/2014 |
| WO | 2014146575 A1 | 9/2014 |
| WO | 2014096051 A9 | 10/2014 |
| WO | 2014155278 A2 | 10/2014 |
| WO | 2014160883 A1 | 10/2014 |
| WO | 2014161570 A1 | 10/2014 |
| WO | 2014186665 A2 | 11/2014 |
| WO | 2015049519 A2 | 4/2015 |
| WO | 2014114651 A9 | 5/2016 |
| WO | 2016103153 A1 | 6/2016 |
| WO | 2017068472 A1 | 4/2017 |

OTHER PUBLICATIONS

Baeten, et al., Anti-interleukin-17A monoclonal antibody secukinumab in treatment of ankylosing spondylitis: a randomised, double-blind, placebo-controlled trial, Lancet, 382(9906), 1705-1713, Nov. 23, 2013.
Baeten, et al., Secukinumab, a Monoclonal Antibody to Interleukin-17A, Significantly Improves Signs and Symptoms of Active Ankylosing Spondylitis: Results of a 52-Week Phase 3 Randomized Placebo-Controlled Trial with Intravenous Loading and Subcutaneous Maintenance Dosing, ACR/ARHP Annual Meeting, abstract 819, 2014.
Baeten, et al., Secukinumab, an Interleukin-17A Inhibitor, in Ankylosing Spondylitis, N Engl J Med, 373(26), 2534-2548, Dec. 24, 2015.
Baeten, et al., The Anti-IL17A Monoclonal Antibody Secukinumab (AIN457) Showed Good Safety and Efficacy in the Treatment of Active Ankylosing Spondylitis, Annals of Rheumatic Diseases, 70(3), 127, 2011.
Baeten, et al., The Anti-IL17A Monoclonal Antibody Secukinumab (AIN457) Showed Good Safety and Efficacy in the Treatment of Active Ankylosing Spondylitis, Arthritis and Rheumatism, 62(12), 3840-3841, 2010.
Baeten, et al., The Anti-IL17A Monoclonal Antibody Secukinumab (AIN457) Showed Good Safety and Efficacy in the Treatment of Active Ankylosing Spondylitis, Late Breaking Abstracts: American College of Rheumatology 2010 Annual Scientific Meeting, 3837-3845, 2010.
Balague, et al., Understanding autoimmune disease: new targets for drug discovery, Drug Discovery Today, 14(19-20), 926-934, Oct. 2009.
Baraliakos, et al., 2486D—Interleukin-17A Blockade with Secukinumab Reduces Spinal Inflammation in Patients with Ankylosing Spondylitis as Early as Week 6, As Detected by Magnetic Resonance Imaging, ACR/ARHP Scientific Meeting, 1-2, Nov. 8, 2011.
Baraliakos, et al., Biologic Therapies for Spondyloartritis: What is new?, Current Rheumatology Reports, 14, 422-427, Aug. 2, 2012.
Baraliakos, et al., Long-term effects of secukinumab on MRI findings in relation to clinical efficacy in subjects with active ankylosing spondylitis: an observational study, Annals of Rheumatic Diseases, 75, 408-412, Aug. 6, 2015.
Baron-Faust, The IL-17 Superfamily: What Future for PsA?, Rheumatology Network, Mar. 18, 2014.
Baseggio, et al., ContainerClosureIntegrityofaGlassPrefillableSyringeinDeepFrozenStorageConditions, Journal of Pharmaceutical Sciences, 113, 1248-1256, 2024.
Bee, et al., Formulation strategy and tactics for mAbs: not all mAbs are the same, Monoclonal Antibodies: Development, Delivery and Applications, 43-57, 2015.
Benhamou, et al., Clinical relevance of C-reactive protein in ankylosing spondylitis and evaluation of the NSAIDs/coxibs' treatment effect on C-reactive protein, Rheumatology, 49(3), 536-541, 2010.
Bhambhani, et al., Lyophilization Strategies for Development of a HighConcentration Monoclonal Antibody Formulation: Benefits and Pitfalls, American Pharmaceutical Review, Jan. 1, 2010.
Boehncke, et al., Burden of Disease: Psoriasis and Psoriatic Arthritis, American Journal of Clinical Dermatology, 14, 377-388, 2013.
Bontempo, Parenteral Formulation for Peptides, Proteins, and Monoclonal Antibodies Drugs: A Commercial Development Overview, Drug Delivery: Principles and Applications, 321-339, 2005.
Boswell, et al., Effects of charge on antibody tissue distribution and pharmacokinetics, Bioconjugate Chemistry, 21, 2153-2163, 2010.
Braun, et al., 2010 update of the ASAS/EULAR recommendations for the management of ankylosing spondylitis, Annals of Rheumatic Diseases, 70, 896-904, 2011.
Braun, et al., Emerging drugs for the treatment of axial and peripheral spondyloarthritis, Expert Opinion on Emerging Drugs, 20(1), 1-14, Jan. 9, 2015.
Braun, et al., Secukinumab (AIN457) in the treatment of ankylosing spondylitis, Expert Opinion on Biological Therapy, 16(5), 711-722, Apr. 7, 2016.
Buggage, et al., The Study of IL-17A Expression as a Biomarker for Patients With Active Noninfectious Uveitis Treated With AIN457, Presentation Abstract, May 4, 2010.
Bye, et al., Biopharmaceutical liquid formulation: a review of the science of protein stability and solubility in aqueous environments, Biotechnology Letters, Feb. 21, 2014.
Carpenter, et al., Rational Design of Stable Protein Formulations, 2002.
Caudill, et al., Container Closure Integrity Test Using Frequency Modulation Spectroscopy Headspace Analysis with Carbon Dioxide as a Tracer Gas, PDA J Pharm Sci and Tech, 75(2), 157-172, Mar.-Apr. 2021.
Chandran, et al., Reappraisal of the effectiveness of methotrexate in psoriatic arthritis: results from a longitudinal observational cohort, Journal of Rheumatology, 35(3), 469-471, 2008.
Chang, et al., Mechanisms of Protein Stabilization in the Solid State, Journal of Pharmaceutical Sciences, 98(9), 2886-2908, Sep. 2009.
Chang, et al., Practical Approaches to Protein Formulation Development, Rationale Design of Stable Protein Formulations—Theory and Practice, 1-25, 2002, Kluwer Academic, New York.
Chen, et al., Sulfasalazine for ankylosing spondylitis (Review), The Cochrane Collaboration, 2005.
Chioato, et al., Efficacy of Influenza and Meningococcal Vaccinations in Healthy Subjects Exposed to Secukinumab 150 Mg: Preliminary Study Results., Arthritis and Rheumatism, 63(10), S711, Oct. 2011.
Chu, et al., A Comprehensive Picture of Non-Site Specific Oxidation of Methionine Residues by Peroxides in Protein Pharmaceuticals, Journal of Pharmaceutical Sciences, 93(12), 3096-3102, Dec. 2004.

(56) References Cited

OTHER PUBLICATIONS

Chu, et al., A Structural and Mechanistic Study of the Oxidation of Methionine Residues in hPTH(1-34) via Experiments and Simulations, Biochemistry, 43, 14139-14148, 2004.
Chu, et al., Molecular Dynamics Simulations and Oxidation Rates of Methionine Residues of Granulocyte Colony-Stimulating Factor at Different pH Values, Biochemistry, 43(4), 1019-1029, 2004.
Chu, et al., On the Mechanisms of Oxidation of Organic Sulfides by H2O2 in Aqueous Solutions, JACS, 126, 900-908, 2004.
Chu, et al., Oxidation of Methionine Residues in Aqueous Solutions: Free Methionine and Methionine in Granulocyte Colony-Stimulating Factor, JACS, 126, 16601-16607, 2004.
Ciccia, et al., Overexpression of Interleukin-23, but Not Interleukin-17, as an Immunologic Signature of Subclinical Intestinal Inflammation in Ankylosing Spondylitis, Arthritis and Rheumatism, 60(4), 955-965, Apr. 2009.
Cimzia prescribing information, revised Jul. 2010, 25 pages.
Clinical trial NCT00809159, Dec. 16, 2008, available at https://www.clinicaltrials.gov/ct2/show/NCT00809159.
Clinical trial NCT00809159, Jun. 22, 2010, available at https://www.clinicaltrials.gov/ct2/show/NCT00809159.
Clinical trial NCT00809614, Apr. 29, 2010, available at https://www.clinicaltrials.gov/ct2/show/NCT00809614.
Clinical Trial NCT00928512, Jul. 29, 2015, available at https://clinicaltrials.gov/ct2/show/NCT00928512.
Clinical Trial NCT00928512, Jun. 25, 2009, available at https://clinicaltrials.gov/ct2/show/NCT00928512.
Clinical trial NCT01107457, Apr. 21, 2010, available at https://www.clinicaltrials.gov/ct2/show/NCT01107457.
Clinical trial NCT01109940, Jun. 22, 2010, available at https://www.clinicaltrials.gov/ct2/show/NCT01109940.
Clinical trial NCT01169844, Jul. 23, 2010, available at https://www.clinicaltrials.gov/ct2/show/NCT01169844.
Clinical trial NCT01649375, Jul. 25, 2012, available at https://www.clinicaltrials.gov/ct2/show/NCT01649375.
Clinical trial NCT01870284, last updated Sep. 15, 2014, available at https://www.clinicaltrials.gov/ct2/show/NCT01870284.
Clinical trial NCT02696785, Feb. 26, 2016, available at https://www.clinicaltrials.gov/ct2/show/NCT02696785.
Clinical Trial NCT04209205, Dec. 24, 2019, available at https://www.clinicaltrials.gov/ct2/show/NCT04209205.
Cosentyx prescribing information, revised Aug. 17, 2017, 44 pages.
Cosentyx prescribing information, revised Jan. 2016, 32 pages.
Cosentyx prescribing information, revised Jan. 2020.
Cosentyx Summary of Products Characteristics, Sep. 1, 2017.
Cross, et al., Postmarketing drug dosage changes of 499 FDA-approved new molecular entities, 1980-1999, Pharmacoepidemiology and Drug Safety, 11, 439-446, Aug. 12, 2002.
Cui, et al., Monoclonal antibodies: formulations of marketed products and recent advances in novel delivery system, Drug Development and Industrial Pharmacy, 43(4), 519-530, Jan. 22, 2017.
Cui, et al., Pharmaceutics, 2nd edition, 24 pages, 2011.
Curriculum Vitae Brian Oscar Porter, Feb. 2017.
Curriculum Vitae Didier Renard, Feb. 2017.
Daikh, et al., Advances in managing ankylosing spondylitis, F1000 Prime Reports, 6(78), Sep. 4, 2014.
Danve, et al., IL-17 Inhibition in Axial Spondyloarthritis, Current Treatment Options in Rheumatology, 1, 221-230, Apr. 2, 2015.
Das, Commercializing High-Concentration mAbs, BioPharm International, 29(11), 47-49, 2016.
Daugherty, et al., Formulation and delivery issues for monoclonal antibody therapeutics, Advanced Drug Delivery Reviews, 58, 686-706, May 22, 2006.
Davis, et al., Recombinant Human Tumor Necrosis Factor Receptor (Etanercept) for Treating Ankylosing Spondylitis, Arthritis and Rheumatism, 48(11), 3230-3236, Nov. 2003.
Declaration of Dr. Brian Oscar Porter, dated Feb. 21, 2017.
Declaration of Dr. Diane R. Mould, dated Jan. 29, 2014.
Declaration of Dr. Oliver Sander, dated Oct. 19, 2015.
Declaration of Dr. Renard Didier, dated Mar. 2, 2017.

Deodhar, et al., Secukinumab 150 mg significantly improved signs and symptoms of non-radiographic axial spondyloarthritis: Result from a phase 3 double-blind, randomized, placebo-controlled study, ACR/ARP Annual Meeting, abstract No. L21, Nov. 12, 2019.
Deodhar, et al., Secukinumab 150 mg significantly improved signs and symptoms of non-radiographic axial spondyloarthritis: Result from a phase 3 double-blind, randomized, placebo-controlled study, ACR/ARP annual meeting, presentation No. L21, Nov. 12, 2019.
Deodhar, et al., Secukinumab significantly improves physical function, quality of life, and work productivity through 52 weeks in subjects with active ankylosing spondylitis in the phase 3 measure 2 study, Annals of Rheumatic Diseases, 74, 1144, 2015.
Deodhar, et al., The term 'non-radiographic axial spondyloarthritis' is much more important to classify than to diagnose patients with axial spondyloarthritis, Annals of Rheumatic Diseases, 75, 791-794, 2016.
Dick, et al., Secukinumab in the Treatment of Noninfectious Uveitis: Results of Three Randomized, Controlled Clinical Trials, Ophthalmology, 120(4), 777-787, Apr. 2013.
Dougados, et al., Arthritis 2 Spondyloarthritis, Lancet, 377, 2127-2137, 2011.
Duncan, et al., The Application of Noninvasive Headspace Analysis to Media Fill Inspection, PDA Journal of Pharmaceutical Science and Technology, 70(3), 230-247, May-Jun. 2016.
EMA, "Summary of Opinion Cosentyx", dated Nov. 20, 2014, available at http://www.ema.europa.eu/docs/en_GB/document_library/Summary_of_opinion_-_Initial_authorisation/human/003729/WC500177620.pdf.
EMA, Committee for Medicinal Products for Human Use (CHMP), Cosentyx assessment report, Nov. 20, 2014.
EMA, Guide to information on human medicines, EMA/515416/2015, 2017, available at http://www.ema.europa.eu/ema/index.jsp?curl=pages/includes/document/document_detail.jsp?webContentId=WC500183131&mid=WC0b01ac058009a3dc.
EPO, Communication pursuant to Article 94(3) EPC, for counterpart EP 15823805.0 dated May 9, 2018.
European public assessment report page screenshot, dated Aug. 29, 2018, available at http://www.ema.europa.eu/ema/index.jsp?curl=pages/includes/document/document_detail.jsp?webContentId=WC500183131&mid=WC0b01ac058009a3dc.
Fagerli, et al., Switching between TNF inhibitors in psoriatic arthritis: data from the NOR-DMARD study, Annals of Rheumatic Diseases, 72, 1840-1844, Apr. 5, 2013.
Falconer, Advances in Liquid Formulations of Parenteral Therapeutic Proteins, Biotechnology Advances, 37, Jun. 27, 2019.
Freeman, Secukinumab improves patient-reported outcomes in ankylosing spondylitis, MDedge, Apr. 27, 2016.
Frokjaer, et al., Protein Drug Stability: A Formulation Challenge, Nature Reviews: Drug Discovery, 4, 298-306, Apr. 2005.
Gaffen, et al., The IL-23-IL-17 immune axis: from mechanisms to therapeutic testing, Nature Reviews Immunology, 14, 585-600, Sep. 2014.
Genco, FDA Approval of the First nr-AxSpA Biologics: Projecting Regulatory & Market Dynamics, Biosimilar Development, Feb. 27, 2019.
Genovese, et al., Efficacy and safety of secukinumab in patients with rheumatoid arthritis: a phase II, dose-finding, double-blind, randomised, placebo controlled study, Annals of Rheumatic Diseases, 72, 863-869, 2013.
Genovese, et al., LY2439821, a Humanized Anti-Interleukin-17 Monoclonal Antibody, in the Treatment of Patients With Rheumatoid Arthritis, Arthritis and Rheumatism, 62(4), 929-939, Apr. 2010.
Genovese, et al., Secukinumab (AIN457) showed a rapid decrease of disease activity in patients with active rheumatoid arthritis including those with high inflammatory burden, Annals of Rheumatic Diseases, 70(3), 472, 2011.
Genovese, et al., Secukinumab (AIN457), a Novel Monoclonal Antibody Targeting IL-17A Demonstrates Efficacy in Active Rheumatoid Arthritis Patients Despite Stable Methotrexate Treatment: Results of a Phase llb Study, Arthritis and Rheumatism, 62(12), 3842, 2010.

(56) References Cited

OTHER PUBLICATIONS

Gladman, et al., Psoriatic arthritis: epidemiology, clinical features, course, and outcome, Annals of Rheumatic Diseases, 64(II), ii14-ii17, 2005.
Goh, et al., Update on biologic therapies in ankylosing spondylitis: a literature review, International Journal of Rheumatic Disease, 15, 445-454, 2012.
Goodman, Secukinumab Successful in Spondylitis, Psoriatic Arthritis, Medscape, Nov. 24, 2014.
Gossec, et al., European League Against Rheumatism recommendations for the management of psoriatic arthritis with pharmacological therapies, Annals of Rheumatic Diseases, 71, 4-12, 2012.
Goswami, et al., Developments and Challenges for mAb-Based Therapeutics, Antibodies, 2, 452-500, Aug. 16, 2013.
Gottlieb, et al., Guidelines of care for the management of psoriasis and psoriatic arthritis Section 2. Psoriatic arthritis: Overview and guidelines of care for treatment with an emphasis on the biologics, Journal of the American Academy of Dermatology, 58(5), 851-864, May 2008.
Gottlieb, et al., Secukinumab Reduces Hscrp Levels in Subjects with Moderate-To-Severe Plaque Psoriasis and Concomitant Psoriatic Arthritis: A Sub-Analysis from the Phase 3 Erasure Study, Annals of the Rheumatic Diseases, 73, AB0738, 1047-1048, Jun. 2014.
Gottlieb, et al., Secukinumab Shows Substantial Improvement in Both Psoriasis Symptoms and Physical Functioning in Moderateto-Severe Plaque Psoriasis Patients With Psoriatic Arthritis: A Subanalysis of a Phase 3, Multicenter, Double-Blind, Placebo-Controlled Study, Abstract Submissions (ACR), Abstract 319, Oct. 25-30, 2013.
Goulabchand, et al., Effect of tumour necrosis factor blockers on radiographic progression of psoriatic arthritis: a systematic review and meta-analysis of randomised controlled trials, Annals of Rheumatic Diseases, 73, 414-419, 2014.
Griffiths, et al., Psoriasis and psoriatic arthritis: Immunological aspects and therapeutic guidelines, Clin Exp Rheumatol, 24(40), S72-S78, 2006.
Haibel, et al., Open label trial of anakinra in active ankylosing spondylitis over 24 weeks, Annals of Rheumatic Diseases, 64, 296-298, 2005.
Haller, Converting Intravenous Dosing to Subcutaneous Dosing With Recombinant Human Hyaluronidase, Pharmaceutical Technology, Oct. 2, 2007.
Hennigan, et al., Adalimumab in ankylosing spondylitis: an evidence_based review of its place in therapy, Core Evidence, 2(4), 295-305, 2008.
Herceptin® [Trastuxumab], FDA Label, Sep. 1998.
History of changes for Study NCT00669916, submitted on Apr. 9, 2015, available at https://clinicaltrials.gov/ct2/history/NCT00669916?V_5=View.
History of changes for Study NCT00669942, submitted on Mar. 27, 2015, available at https://clinicaltrials.gov/ct2/history/NCT00669942?A=5&B=5&C=merged.
History of changes for Study NCT00805480, submitted on Jan. 28, 2015, available at https://clinicaltrials.gov/ct2/history/NCT00805480?V_4=View.
History of changes for Study NCT00809159, submitted on Dec. 7, 2015, available at https://clinicaltrials.gov/ct2/history/NCT00809159?V_9=View#StudyPageTop.
History of changes for Study NCT00809614, submitted on Oct. 14, 2015, available at https://clinicaltrials.gov/ct2/history/NCT00809614?A=5&B=5&C=merged.
History of Changes for Study NCT00928512, Mar. 12, 2010, available at https://www.clinicaltrials.gov/ct2/show/NCT00928512.
History of changes for Study NCT00928512, submitted on Oct. 7, 2015, available at https://clinicaltrials.gov/ct2/history/NCT00928512?V_9=View#StudyPageTop.
History of Changes for Study NCT00995709, Oct. 14, 2009, available at https://www.clinicaltrials.gov/ct2/show/NCT00995709.
History of changes for Study NCT00995709, submitted on Aug. 13, 2015, available at https://clinicaltrials.gov/ct2/history/NCT00995709?V_7=View.
History of Changes for Study NCT01032915, Oct. 24, 2010, available at https://www.clinicaltrials.gov/study/NCT01032915.
History of changes for Study NCT01032915, submitted on Oct. 8, 2015, available at https://clinicaltrials.gov/ct2/history/NCT01032915?V_4=View.
History of Changes for Study NCT01071252, Feb. 18, 2010, available at https://www.clinicaltrials.gov/ct2/show/NCT01071252.
History of changes for Study NCT01071252, submitted on Feb. 12, 2015, available at https://clinicaltrials.gov/ct2/history/NCT01071252?V_1=View.
History of Changes for Study NCT01090310, Sep. 28, 2010, available at https://www.clinicaltrials.gov/ct2/show/NCT01090310.
History of changes for Study NCT01090310, submitted on Dec. 8, 2015, available at https://clinicaltrials.gov/ct2/history/NCT01090310?V_2=View.
History of changes for Study NCT01093846 submitted on Jan. 22, 2016, available at https://clinicaltrials.gov/ct2/history/NCT01093846?V_2=View.
History of Changes for Study NCT01093846, Oct. 13, 2010, available at https://www.clinicaltrials.gov/study/NCT01093846.
History of Changes for Study NCT01095250, Oct. 13, 2010, available at https://clinicaltrials.gov/ct2/history/NCT01095250?A=6&B=6&C=merged.
History of changes for Study NCT01095250, submitted on Oct. 5, 2015, available at https://clinicaltrials.gov/ct2/history/NCT01095250?A=6&B=6&C=merged.
History of Changes for Study NCT01103024, Oct. 15, 2010, available at https://clinicaltrials.gov/study/NCT01103024?a=2&tab=history.
History of changes for Study NCT01103024, submitted on May 2, 2012, available at https://clinicaltrials.gov/ct2/history/NCT01103024?A=2&B=2&C=merged.
History of changes for Study NCT01109940, submitted on Nov. 15, 2016, available at https://clinicaltrials.gov/ct2/history/NCT01109940?V_2=View.
History of changes for Study NCT01169844, submitted on Nov. 16, 2016, available at https://clinicaltrials.gov/ct2/history/NCT01169844?A=1&B=1&C=merged.
History of Changes for Study NCT01327664, Mar. 31, 2011, available at https://clinicaltrials.gov/study/NCT01327664?tab=history&a=1.
History of changes for Study NCT01327664, submitted on Dec. 5, 2013, available at https://clinicaltrials.gov/ct2/history/NCT01327664?V_1=View.
History of Changes for Study NCT01350804, Sep. 23, 2011, available at https://clinicaltrials.gov/study/NCT01350804?tab=history&a=3.
History of changes for Study NCT01350804, submitted on May 4, 2016, available at https://clinicaltrials.gov/ct2/history/NCT1350804?A=3&B=3&C=merged.
History of changes for Study NCT01358175, submitted on Oct. 20, 2011, available at https://clinicaltrials.gov/ct2/history/NCT01358175?V_2=View#StudyPageTop.
History of Changes for Study NCT01358578, Aug. 17, 2011, available at https://clinicaltrials.gov/study/NCT01358578?tab=history&a=6.
History of changes for Study NCT01358578, submitted on Mar. 29, 2019, available at https://clinicaltrials.gov/ct2/history/NCT01358578?A=6&B=6&C=merged.
History of Changes for Study NCT01365455, Oct. 12, 2011, available at https://clinicaltrials.gov/study/NCT01365455?a=10&tab=history.
History of changes for Study NCT01365455, submitted on Mar. 20, 2019, available at https://clinicaltrials.gov/ct2/history/NCT01365455?A=10&B=10&C=merged.
History of Changes for Study NCT01377012, Sep. 28, 2011, available at https://clinicaltrials.gov/study/NCT01377012?a=4&tab=history.

(56) References Cited

OTHER PUBLICATIONS

History of changes for Study NCT01377012, submitted on Feb. 9, 2017, available at https://clinicaltrials.gov/ct2/history/NCT1377012?A=4&B=4&C=merged.
History of Changes for Study NCT01392326, Sep. 23, 2011, available at https://clinicaltrials.gov/study/NCT01392326?tab=history&a=2.
History of changes for Study NCT01392326, submitted on Jan. 5, 2016, available at https://clinicaltrials.gov/ct2/history/NCT01392326?A=2&B=2&C=merged.
History of Changes for Study NCT01406938, Aug. 15, 2011, available at https://clinicaltrials.gov/study/NCT01406938?a=2&tab=history.
History of changes for Study NCT01406938, submitted on Apr. 30, 2015, available at https://clinicaltrials.gov/ct2/history/NCT01406938?A=2&B=2&C=merged.
History of Changes for Study NCT01412944, Aug. 8, 2011, available at https://clinicaltrials.gov/study/NCT01412944?tab=history&a=1.
History of changes for Study NCT01412944, submitted on Mar. 17, 2015, available at https://clinicaltrials.gov/ct2/history/NCT01412944?A=1&B=1&C=merged.
History of changes for Study NTC01359943, submitted on Oct. 18, 2011, available at https://clinicaltrials.gov/ct2/history/NCT01359943?V_2=View.
Hou, et al., Methotrexate ameliorates pristane-induced arthritis by decreasing IFN-alpha and IL-17A expressions, Journal of Zhejiang University—Science B, 12(1), 40-46, 2011.
Hueber, et al., Effects of AIN457, a Fully Human Antibody to Interleukin-17A, on Psoriasis, Rheumatoid Arthritis, and Uveitis, Science Translational Medicine, 2(52), 52ra72, Oct. 6, 2010.
Hueber, et al., Secukinumab, a human anti-IL-17A monoclonal antibody, for moderate to severe Crohn's disease: unexpected results of a randomised, double-blind placebo-controlled trial, Gut, 61, 1693-1700, 2012.
Humira prescribing information, revised Mar. 2020.
Igawa, et al., Reduced elimination of IgG antibodies by engineering the variable region, Protein Engineering, Design and Selection, 23(5), 385-392, Feb. 15, 2010.
Inman, et al., Efficacy and Safety of Golimumab in Patients With Ankylosing Spondylitis, Arthritis and Rheumatism, 58(11), 3402-3412, Nov. 2008.
International Nonproprietary Names for Pharmaceutical Substances (INN), WHO Drug Information, 24(3), 259-290, 2010.
Jacob, et al., Stability of Proteins in Aqueous Solution and Solid State, Indian Journal of Pharmaceutical Sciences, 68(2), 154-163, Apr. 9, 2006.
Jandus, et al., Increased Nos. of Circulating Polyfunctional Th17 Memory Cells in Patients With Seronegative Spondylarthritedes, Arthritis and Rheumatism, 58(8), 2307-2317, Aug. 2008.
Kagan, et al., Subcutaneous Absorption of Monoclonal Antibodies: Role of Dose, Site of Injection, and Injection Volume on Rituximab Pharmacokinetics in Rats, Pharmaceutical Research, 29, 490-499, 2012.
Kang, et al., Rapid Formulation Development for Monoclonal Antibodies, BioProcess International, 14(4), 40-45, Apr. 2016.
Katdare, et al., Excipient Development for Pharmaceutical, Biotechnology, and Drug Delivery Systems, 12 pages, 2006.
Kavanaugh, et al., Efficacy of Subcutaneous Secukinumab in Patients with Active Psoriatic Arthritis Stratified by Prior Tumor Necrosis Factor Inhibitor Use: Results from the Randomized Placebo-controlled FUTURE 2 Study, Journal of Rheumatology, 43(9), 1713-1717, 2016.
Kavanaugh, et al., The Infliximab Multinational Psoriatic Arthritis Controlled Trial (IMPACT): results of radiographic analyses after 1 year, Annals of Rheumatic Diseases, 65, 1038-1043, Jan. 26, 2006.
Kavanaugh, et al., Ustekinumab, an anti-IL-12/23 p40 monoclonal antibody, inhibits radiographic progression in patients with active psoriatic arthritis, Annals of Rheumatic Diseases, 73, 1000-1006, Feb. 19, 2014.
Kelly, Secukinumab Effective for Ankylosing Spondylitis in Phase 3 Trials, Medscape, Dec. 30, 2015.
Kelzer, et al., Clinical Pharmacokinetics of Therapeutic Monoclonal Antibodies, Clinical Pharmacokinetics, 49(8), 493-507, 2010.
Kiltz, et al., Treatment of ankylosing spondylitis in patients refractory to TNF-inhibition: are there alternatives?, Current Opinion in Rheumatology, 24(3), 252-260, May 2012.
Kivitz, et al., Efficacy and Safety of Secukinumab 150 mg with and Without Loading Regimen in Ankylosing Spondylitis: 104-week Results from MEASURE 4 Study, Rheumatology and Therapy, 5, 447-462, Aug. 18, 2018.
Kling, Highly Concentrated Protein Formulations: Finding Solutions for the Next Generation of Parenteral Biologics, BioProcess International, 12(5), May 2014.
Kocijan, et al., Anti-TNFs in axial spondyloarthritis, Wiener Medizinische Wochenschrift, 165, 10-13, Jan. 9, 2015.
Kroon, et al., Identification of Sites of Degradation in a Therapeutic Monoclonal Antibody by Peptide Mapping, Pharmaceutical Research, 9(11), 1386-1393, 1992.
Kunder, Treatment of the patients with psoriatic arthritis, Medical News, 6, 34-41, 2013.
Lacy, et al., Free sulfhydryl measurement as an indicator of antibody stability, Analytical Biochemistry, 382, 66-68, Jul. 26, 2008.
Lalonde, et al., Model-based Drug Development, Clinical Pharmacology and Therapeutics, 82(1), 21-32, Jul. 2007.
Lam, et al., Antioxidants for Prevention of Methionine Oxidation in Recombinant Monoclonal Antibody HER2, Journal of Pharmaceutical Sciences, 86(11), 1250-1255, Nov. 1997.
Landewe, et al., Efficacy of certolizumab pegol on signs and symptoms of axial spondyloarthritis including ankylosing spondylitis: 24-week results of a doubleblind randomised placebo-controlled Phase 3 stu, Annals of Rheumatic Diseases, 73, 39-47, 2014.
Langley, et al., Secukinumab in Plaque Psoriasis—Results of Two Phase 3 Trials, The New England Journal of Medicine, 371(4), 326-338, Jul. 24, 2014.
Late-Breaking Abstracts: American College of Rheumatology 2010 Annual Scientific Meeting.
Letko, et al., IV Secukinumab Is an Effective Treatment in Patients With Noninfectious Uveitis Requiring Steroid Sparing Immunosuppressive Therapy, Invest Ophthalmol Vis Sci, 54, E-Abstract 5929, 2013.
Lowe, et al., Aggregation, Stability, and Formulation of Human Antibody Therapeutics, Advances in Protein Chemistry and Structural Biology, 84, 41-61, 2011.
Lubberts, Th17 cytokines and arthritis, Semin Immunopathol, 32, 43-53, Feb. 4, 2010.
Machado, et al., New developments in the diagnosis and treatment of axial spondyloartritis, Clinical Investigation, 3(2), 153-171, 2013.
Machold, et al., Very recent onset rheumatoid arthritis: clinical and serological patient characteristics associated with radiographic progression over the first years of disease, Rheumatology, 46, 342-349, 2007.
Madej, et al., Cytokine Profiles in Axial Spondyloarthritis, Reumatologia, 53(1), 9-13, 2015.
Maksymowych, et al., OP0114 Secukinumab for the Treatment of Ankylosing Spondylitis: Comparative Effectiveness Results versus Adalimumab Using a Matching-Adjusted Indirect Comparison, Annals of Rheumatic Diseases, Jun. 10, 2016.
Malarone, prescribing information, revised Jun. 2013, 22 pages.
Maldonado-Ficco, et al., Secukinumab: a promising therapeutic option in spondyloarthritis, Clinical Rheumatology, 35, 2151-2161, 2016.
Mantravadi, et al., Tumor necrosis factor inhibitors in psoriatic arthritis, Expert Review of Clinical Pharmacology, 10(8), 899-910, May 22, 2017.
Martinez, et al., Comparability of a Three-Dimensional Structure in Biopharmaceuticals Using Spectroscopic Methods, Journal of Analytical Methods in Chemistry, 950598, May 22, 2014.
Marzo-Ortega, et al., Secukinumab provides sustained improvements in the signs and symptoms of active ankylosing spondylitis:

(56) References Cited

OTHER PUBLICATIONS 2-year results from a phase 3 trial with subcutaneous loading and maintenance dosing (measure 2), Annals of Rheumatic Diseases, 75(2), 812-813, 2016.
Mayo Clinic_Apr. 30, 2020_Diagnosis and treatment of Uveitis https://www.mayoclinic.org/diseasesconditions/uveitis/diagnosis-treatment/drc-20378739?p=1.
McGoff, et al., Solution Formulation of Proteins/Peptides, Informa Healthcare, 133-151, 2008.
McInnes, et al., Anti-Interleukin 17A Monoclonal Antibody Secukinumab Reduces Signs and Symptoms of Psoriatic Arthritis in a 24-Week Multicenter, Double-Blind, Randomized, Placebo-Controlled Trial, Arthritis and Rheumatism, 63(10), S306, Oct. 2011.
McInnes, et al., Anti-Interleukin 17A Monoclonal Antibody Secukinumab Reduces Signs and Symptoms of Psoriatic Arthritis in a 24-Week Multicenter; Double_-blind, Randomized, Placebo-Controlled Trial, Arthritis and Rheumatism, 63, Nov. 2011.
McInnes, et al., Secukinumab, a human anti-interleukin-17A monoclonal antibody, in patients with psoriatic arthritis (FUTURE 2): a randomised, double-blind, placebo-controlled, phase 3 trial, Lancet, 386, 1137-1146, Sep. 19, 2015.
McKee, Novartis' Cosentyx shown to inhibit joint damage in PsA, Pharma Times, Nov. 7, 2017.
Mease, et al., Brodalumab, an Anti-IL17RA Monoclonal Antibody, in Psoriatic Arthritis, N Engl J Med., 370(24), 2295-2306, Jun. 12, 2014.
Mease, et al., Managing Patients with Psoriatic Disease: The Diagnosis and Pharmacologic Treatment of Psoriatic Arthritis in Patients with Psoriasis, Drugs, 74, 423-441, Feb. 25, 2014.
Mease, et al., Psoriatic arthritis assessment tools in clinical trials, Annals of Rheumatic Diseases, 64, ii49-ii54, 2005.
Mease, et al., Secukinumab: A New Treatment Option for Psoriatic Arthritis, Rheumatology Therapy, 3, 5-29, 2016.
Mease, et al., Subcutaneous Secukinumab Inhibits Radiographic Progression in Psoriatic Arthritis: Primary Results from a Large Randomized, Controlled, Double-Blind Phase 3 Study, ACR/ARHP Annual Meeting, Oct. 19, 2017.
Mease, Non anti-TNF biologics on SpA and PsA, Annals of Rheumatic Diseases, abstract SP0147, Jun. 8, 2012.
Meibohm, The Role of Pharmacokinetics and Pharmacodynamics in the Development of Biotech Drugs, Pharmacokinetics and Pharmacodynamics of Biotech Drugs: Principles and Case Studies in Drug Development, part 1, 3-13, 2006.
Melis, et al., Systemic levels of IL-23 are strongly associated with disease activity in rheumatoid arthritis but not spondyloarthritis, Annals of Rheumatic Diseases, 69, 618-623, 2010.
Menter, et al., Guidelines of care for the management of psoriasis and psoriatic arthritis, Journal of the American Academy of Dermatology, 65(1), 137-174, Jul. 2011.
Methods of Treating Rheumatoid Arthritis Using IL-17 Antagonists, 99 pages.
Mitragotri et al, Overcoming the challenges in administering biopharmaceuticals: formulation and delivery strategies, Nature Reviews: Drug Discovery, 13, 655-672, Sep. 2014.
Mok, et al., Drug levels, anti-drug antibodies, and clinical efficacy of the anti-TNFalpha biologics in rheumatic diseases, Clinical Rheumatology, 32, 1429-1435, 2013.
Mould, et al., Pharmacokinetics and Pharmacodynamics of Monoclonal Antibodies, BioDrugs, 24(1), 23-39, 2010.
Mrowietz, et al., Definition of treatment goals for moderate to severe psoriasis: a European consensus, Archives for Dermatological Research, 303, 1-10, Jan. 2011.
Narasimhan, et al., High-dose monoclonal antibodies via the subcutaneous route: challenges and technical solutions, an industry perspective, Therapeutic Delivery, 3(7), 889-900, 2012.
Nash, et al., Secukinumab for Ankylosing Spondylitis: comparative effectiveness results versus adalimumab using a matching-adjusted indirect comparison, International Journal of Rheumatic Diseases, 19(Suppl. 2), 244-245, 2016.
Nash, et al., Secukinumab for psoriatic arthritis: comparative effectiveness results versus etanercept up to 24 weeks using a matching-adjusted indirect comparison, International Journal of Rheumatic Diseases, 19(2), 163, 2016.
Nash, et al., Secukinumab for the treatment of psoriatic arthritis: comparative effectiveness results versus adalimumab up to 48 weeks using a matching-adjusted indirect comparison, Annals of Rheumatic Diseases, 75(2), 353, 2016.
Ness, Surveying the pipeline of biologics to treat inflammatory conditions, PharmD, Sep. 12, 2011.
Newsome, et al., The clinical pharmacology of therapeutic monoclonal antibodies in the treatment of malignancy; have the magic bullets arrived?, British Journal of Clinical Pharmacology, 66(1), 6-19, May 22, 2008.
NHSC Publication, May 2010, AIN-457 for posterior uveitis, 5 pages.
Novartis announces result of Prevent Study, dated Nov. 12, 2019, downloaded Dec. 11, 2019.
Novartis Media Release, Novartis announces new one-year results demonstrating sustained secukinumab efficacy in ankylosing spondylitis patients, Jun. 10, 2015.
Novartis Media Release, Study: Drug helps with psoriasis symptoms, Fox News, Oct. 24, 2011.
Novartis, Clinical Trial Results, Protocol No. CAIN457F2304, study completion date Nov. 2020.
Ogura, et al., Interleukin-17 promotes autoimmunity by triggering a positive-feedback loop via Interleukin-6 induction, Immunity, 29, 628-636, Oct. 17, 2008.
Olivieri, et al., Emerging drugs for psoriatic arthritis, Expert Opin. Emerging Drugs, 15(3), 399-414, Jun. 9, 2010.
Online publication, Arthritis & Rheumatism, Sep. 27, 2011.
Online publication, Arthritis & Rheumatism, Dec. 9, 2011.
Pan, et al., Comparative Oxidation Studies of Methionine Residues Reflect a Structural Effect on Chemical Kinetics in rhG-CSF, Biochemistry, 45(51), 15430-15443, 2006.
Patel, et al., Effect of IL-17A blockade with secukinumab in autoimmune diseases, Annals of Rheumatic Diseases, 72, 116-123, 2013.
Pavelka, et al., Efficacy, safety, and tolerability of secukinumab in patients with active ankylosing spondylitis: a randomized, doubleblind phase 3 study, MEASURE 3, Arthritis Research and Therapy, 19(285), 27 pages, Dec. 22, 2017.
Poddubnyy, Axial spondyloarthritis: is there a treatment of choice, Therapeutic Advances in Musculoskeletal Disease, 5(1), 45-54, 2013.
Poddubnyy, et al., Adalimumab for the treatment of ankylosing spondylitis and nonradiographic axial spondyloarthritis—a five-year update, Expert Opinion on Biological Therapy, 13(11), 1599-1611, 2013.
Poddubnyy, et al., Spontaneous, drug-induced, and drug-free remission in peripheral and axial spondyloarthritis, Best Practice & Research Clinical Rheumatology, 28, 807-818, 2014.
Porter, et al., Lymphatic transport of proteins after s.c. injection: implications of animal model selection, Advanced Drug Delivery Reviews, 50, 157-171, 2001.
Porter, et al., Lymphatic Transport of Proteins After Subcutaneous Administration, Journal of Pharmaceutical Sciences, 89(3), 297-310, Mar. 2000.
Potter, et al., Association of rheumatoid factor and anti-cyclic citrullinated peptide positivity, but not carriage of shared epitope or PTPN22 susceptibility variants, with anti-tumour necrosis factor response in rheumatoid arthritis, Annals of Rheumatic Diseases, 68, 69-74, 2009.
Produfoot (Updated by John Collett), Dosage Regimens, Pharmaceutics: The Science of Dosage Form Design, chapter 19, 275-288, 2001.
Proprietor's letter to the Examining Division, Feb. 15, 2018.
Psoriatic Arthritis (PsA): A distinct, complex disease, retrieved from www.discoverpsa.com, on Feb. 2, 2016.
Quinti, et al., Polyvalent immunoglobulins: challenges and perspectives, Blood Transfusion, 11, 40-44, 2013.
Recker, et al., Insufficiently dosed intravenous ibandronate injections are associated with suboptimal antifracture efficacy in postmenopausal osteoporosis, Bone, 34, 890-899, 2004.

(56) References Cited

OTHER PUBLICATIONS

Reichert, Antibody-based therapeutics to watch in 2011, mAbs, 3(1), 76-99, Jan. 1, 2011.
Remicade (Infliximab) prescribing information, revised Oct. 2015, 57 pages.
Remicade (Infliximab), Aug. 12, 1998, 12 pages.
Rheumatologists chose ACR50, ACR70 over ACR20 as endpoints when prescribing psoriatic arthritis drugs, One Minute Read, retrieved from www.healio.com, on Sep. 1, 2020.
Richter, et al., Mechanistic Determinants of Biotherapeutics Absorption Following SC Administration, The AAPS Journal, 14(3), 559-570, Sep. 2012.
Robotham, et al., Detection and quantification of free sulfhydryls in monoclonal antibodies using maleimide labeling and mass spectrometry, mAbs, 11(4), 757-766, 2019.
Rodriguez, et al., Old and new treatment targets in axial spondyloarthritis, RMD Open, 1, Apr. 5, 2015.
Romao, et al., Old drugs, old problems: where do we stand in prediction of rheumatoid arthritis responsiveness to methotrexate and other synthetic DMARDs?, BMC Medicine, 11(17), 24 pages, 2013.
Rouet, et al., Stability engineering of the human antibody repertoire, FEBS Letters, 588, 269-277, Nov. 28, 2013.
Rudwaleit, et al., The development of Assessment of Spondyloarthritis international Society classification criterai for axial spondyloarthritis (part I): classification of paper patients by expert opinion including uncertainty appraisal, Extended Report, Mar. 17, 2009.
Saber, et al., Remission in Psoriatic Arthritis: is it Possible and How Can it Be Predicted?, Arthritis Research and Therapy, 12, 2010.
Sacks, et al., Scientific and Regulatory Reasons for Delay and Denial of FDA Approval of Initial Applications for New Drugs, 2000-2012, JAMA, 311(4), 378-384, 2014.
Salvana, et al., Infectious Complications Associated with Monoclonal Antibodies and Related Small Molecules, Clinical Microbiology Reviews, 22(2), 274-290, Apr. 2009.
Samson, et al., An Open-Label Proof-Of Concept Study to Assess the Efficacy of AIN457 in Patients With Noninfectious Uveitis, ARVO Annual Meeting Abstract, 51, Abstract 2917, Apr. 2010.
Schauenstein, et al., Labile Disulfide Bonds and Free Thiol Groups in Human IgG, Int. Archs Allergy appl. Immun., 80, 174-179, 1986.
Scott, et al., Rheumatoid arthritis, Lancet, 376, 1094-1108, 2010.
Scott, Formulation Development: Making the Medicine, BioProcess International, 4, 42-56, Mar. 2006.
Shire, et al., Challenges in the Development of High Protein Concentration Formulations, Journal of Pharmaceutical Sciences, 93(6), 1390-1402, Jun. 2004.
Shire, Formulation and manufacturability of biologics, Current Opinion in Biotechnology, 20, 1-7, 2009.
Shostak, et al., Back pain of inflammatory genesis: seronegative spondyloarthropathy—the main approaches to diagnosis and therapy, The Clinician, 5, Jan. 2011.
Sieper, et al., Assessment of short-term symptomatic efficacy of tocilizumab in ankylosing spondylitis: results of randomised, placebo-controlled trials, Annals of Rheumatic Diseases, 73, 95-100, 2014.
Sieper, et al., Early response to adalimumab predicts long-term remission through 5 years of treatment in patients with ankylosing spondylitis, Annals of Rheumatic Diseases, 2011.
Sieper, et al., Efficacy and safety of adalimumab in patients with non-radiographic axial spondyloarthritis: results of a randomised placebo-controlled trial (ABILITY-1), Clinical and epidemiological research, 815-822, Jul. 7, 2012.
Sieper, et al., Sarilumab for the treatment of ankylosing spondylitis: results of a Phase II, randomised, double-blind, placebo-controlled study (ALIGN), Annals of Rheumatic Diseases, 74, 1051-1057, 2015.
Sieper, et al., Secukinumab efficacy in anti-TNF-naive and anti-TNF-experienced subjects with active ankylosing spondylitis: results from the MEASURE 2 Study, Annals of Rheumatic Diseases, 76, 571-575, 2017.
Sieper, et al., Secukinumab efficacy in anti-TNF-naive and anti-TNF-experienced subjects with active ankylosing spondylitis: results from the MEASURE 2 Study, Annals of Rheumatic Diseases, Aug. 31, 2016.
Sieper, et al., Secukinumab, a Monoclonal Antibody to Interleukin-17A, Significantly Improves Signs and Symptoms of Active Ankylosing Spondylitis: Results of a Phase 3, Randomized, Placebo-Controlled Trial with Subcutaneous Loading and Maintenance Dosing, ACR/ARHP Annual Meeting, abstract 536, 2014.
Singh, et al., Protein and DNA destabilization by osmolytes: The other side of the coin, Life Sciences, 88, 117-125, Nov. 1, 2010.
Smolen, et al., EULAR recommendations for the management of rheumatoid arthritis with synthetic and biological disease-modifying antirheumatic drugs, Annals of Rheumatic Diseases, May 5, 2010.
Song, et al., Consistently Good Clinical Response in Patients with early Axial Spondyloartritis after 3 Years of continuous Treatment with Etanercept: Longterm Data of the ESTHER Trial, The Journal of Rheumatology, 41(10), 2034-2040, 2014.
Song, et al., Different Response to Rituximab in Tumor Necrosis Factor Blocker-Naive Patients With Active Ankylosing Spondylitis and in Patients in Whom Tumor Necrosis Factor Blockers Have Failed, Arthritis and Rheumatism, 62(5), 1290-1297, May 2010.
Song, et al., Treatment of active ankylosing spondylitis with abatacept: an open-label, 24-week pilot study, Annals of Rheumatic Diseases, 70, 1108-1110, 2011.
Stelara Highlights of Prescribing Information, revised Sep. 2016.
Strand, et al., Secukinumab for the treatment of psoriatic arthritis: comparative effectiveness versus infliximab using a matching-adjusted indirect comparison, ACR/ARHP Annual Meeting, abstract 1729, Sep. 28, 2016.
Supreme People's Court of People's Republic of China, Administrative Judgment, Entresto Combo, 2019.
Tak, et al., A1N457 Shows a Good Safety Profile and Clinical Benefit in Patients with Active Rheumatoid Arthritis (RA) Despite Methotrexate Therapy: 16-Weeks Results From a Randomized Proof-of-Concept Trial, ACR/ARHP Scientific Meeting, presentation No. 1922, Oct. 20, 2009.
Taltz prescribing information, revised Aug. 2019, 1 page.
Tamiflu prescribing information, revised Jan. 17, 2008, 29 pages.
Tang, et al., Pharmacokinetic Aspects of Biotechnology Products, Journal of Pharmaceutical Sciences, 93(9), 2184-2204, Sep. 2004.
Uchiyama, Liquid formulation for antibody drugs, Biochimica et Biophysica Acta, 1844, 2041-2052, Aug. 13, 2014.
Urano, Diagnosis of spondyloarthritis: from ankylosing spondylitis to axial spondyloarthritis, Inflammation and Immunity, 21(1), 79-85, 2013.
U.S. Appl. No. 61/410,533, filed Nov. 5, 2010.
Van Der Heijde, et al., Adalimumab effectiveness for the treatment of ankylosing spondylitis is maintained for up to 2 years: long-term results from the ATLAS trial, Annals of Rheumatic Diseases, 68, 922-929, 2009.
Van Der Heijde, et al., Effect of different imputation approaches on the evaluation of radiographic progression in patients with psoriatic arthritis: results of the RAPID-PsA 24-week phase III double-blind randomised placebo-controlled study of certolizumab pegol, Annals of Rheumatic Diseases, 73, 233-237, 2014.
Van Der Heijde, et al., Efficacy and Safety of Adalimumab in Patients With Ankylosing Spondylitis, Arthritis and Rheumatism, 54(7), 2136-2146, Jul. 2006.
Van Der Heijde, et al., Efficacy and Safety of Infliximab in Patients With Ankylosing Spondylitis, Arthritis and Rheumatism, 52(2), 582-591, Feb. 2005.
Van Der Heijde, et al., Psoriatic arthritis imaging: a review of scoring methods, Annals of Rheumatic Diseases, 64 (suppl. 2), 61-64, 2005.
Van Der Horst-Bruinsma, et al., A systematic comparison of rheumatoid arthritis and ankylosing spondylitis, Clinical and Experimental Rheumatology, 27(55), S43-S49, 2009.
Vandooren, et al., Absence of a Classically Activated Macrophage Cytokine Signature in Peripheral Spondylarthrites, Including Psoriatic Arthritis, Arthritis and Rheumatism, 60(4), 966-975, Apr. 2009.

(56) References Cited

OTHER PUBLICATIONS

Wang, Advanced protein formulations, Protein Science, 24, 1031-1039, Apr. 9, 2015.
Wang, et al., Antibody Structure, Instability, and Formulation, Journal of Pharmaceutical Sciences, 96(1), 1-26, Jan. 2007.
Wang, et al., Fixed Dosing Versus Body Size-Based Dosing of Monoclonal Antibodies in Adult Clinical Trials, Journal of Clinical Pharmacology, 49(9), 1012-1024, 2009.
Wang, et al., Monoclonal Antibody Pharmacokinetics and Pharmacodynamics, Clinical Pharmacology and Therapeutics, 84(5), 548-558, Nov. 2008.
Wang, et al., Protein aggregation—Pathways and influencing factors, International Journal of Pharmaceutics, 390(2), 89-99, Feb. 24, 2010.
Wang, Instability, stabilization, and formulation of liquid protein pharmaceuticals, International Journal of Pharmaceutics, 185, 129-188, Apr. 28, 1999.
Ward, et al., American College of Rheumatology/Spondylitis Association of America/Spondyloarthritis Research and Treatment Network 2015 Recommendations for the Treatment of Ankylosing Spondylitis and Nonradiographic Axial Spondyloarthritis, Arthritis and Rheumatology, 68(2), 282-298, Feb. 2016.
Wayback Machine, www.rheumatology.org, retrieved from the Internet: URL—https://web.archive.org/web/20101029090319/http:/www.rheumatology.org/, Oct. 29, 2010.
Wei, et al., Development of a rapid reversed-phase liquid chromatographicmethod for total free thiol quantitation in protein therapeutics, Journal of Pharmaceutical and Biomedical Analysis, 189, 113434, Jun. 18, 2020.
Weitz, et al., Ustekinumab: targeting the IL-17 pathway to improve outcomes in psoriatic arthritis, Expert Opinion on Biological Therapy, 14(4), 515-526, 2014.
Welch, et al., Facile quantitation of free thiols in a recombinant monoclonal antibody by reversed-phase high performance liquid chromatography with hydrophobicity-tailored thiol derivatization, Journal of Chromatography B, 1092, 158-167, Jun. 2, 2018.
Weselman, Psoriatic Arthritis, American College of Rheumatology, 2017.
Wiley: "Publication Date of D2", Dec. 9, 2021 (Dec. 9, 2021), pp. 1-2, XP55871165, [retrieved on Dec. 9, 2021].
Wolbink, et al., Dealing with immunogenicity of biologicals: assessment and clinical relevance, Current Opinion in Rheumatology, 21, 211-215, 2009.
Wuchner, et al., Industry perspective on a holistic container closure integrity approach to parenteral combination products, European Journal of Pharmaceutics and Biopharmaceutics, 194, 20-35, 2024.
Yang, et al., Crystalline monoclonal antibodies for subcutaneous delivery, PNAS, 100(12), 6934-6939, Jun. 10, 2003.
Yang, et al., Secukinumab in the treatment of psoriasis: patient selection and perspectives, Psoriasis: Targets and Therapy, 8, 75-82, 2018.
Yildirim, et al., Associations between Acute Phase Reactant Levels and Disease Activity Score (DAS28) in Patients with Rheumatoid Arthritis, Annals of Clinical & Laboratory Science, 34(4), 423-426, 2004.
Yin, et al., Effects of Antioxidants on the Hydrogen Peroxide-Mediated Oxidation of Methionine Residues in Granulocyte Colony-Stimulating Factor and Human Parathyroid Hormone Fragment 13-34, Pharmaceutical Research, 21(12), 2377-2383, Dec. 2004.
Yingjin, et al., Modern Pharmaceutical Technology, 16 pages, 2004.
Yoshida, et al., Methotrexate Suppresses Inflammatory Agonist Induced Interleukin 6 Synthesis in Osteoblasts, The Journal of Rheumatology, 32(5), 787-795, 2005.
Zbacnik, et al., Role of Buffers in Protein Formulations, Journal of Pharmaceutical Sciences, 106, 713-733, Nov. 26, 2016.
Zhao, et al., Clinical pharmacology considerations in biologics development, Acta Pharmacologica Sinica, 33, 1339-1347, 2012.
Zhao, et al., The Antibody Drug Absorption Following Subcutaneous or Intramuscular Administration and Its Mathematical Description by Coupling Physiologically Based Absorption Process with the Conventional Compartment Pharmacokinetic Model, The Journal of Clinical Pharmacology, 53(3), 314-325, 2013.
Zuidema, et al., Release and absorption rates of intramuscularly and subcutaneously injected pharmaceuticals (II), International Journal of Pharmaceutics, 105, 189-207, 1994.
Zhou et all, Journal of Pharmaceutical Sciences (2010) 99:4239-4250.
Pipes et al., Journal of Pharmaceutical Sciences (2010) 99:4469-4476.
Lam et al., Journal of Pharmaceutical Sciences (1997) 86:1250-1255.
Li et al., Biochemistry (1995) 5762-5772.
Lu et al., Archives of Biochemistry and Biophysics (1999) 362:1-11.
Li et al., Biotechnology and Bioengineering (1995) 48:490-500.
Liu et al., Biochemistry (2008) 47:5088-5100.
Hovorka & Schöneich, Journal of Pharmaceutical Sciences (2001) 90:253-269.

\* cited by examiner

SEQUENCE LISTING

```
Sequence total quantity: 15
SEQ ID NO: 1                  moltype = AA  length = 5
FEATURE                       Location/Qualifiers
REGION                        1..5
                              note = CDR1 = hypervariable region 1 of heavy chain of
                              AIN457
source                        1..5
                              mol_type = protein
                              organism = synthetic construct
SEQUENCE: 1
NYWMN                                                                            5

SEQ ID NO: 2                  moltype = AA  length = 17
FEATURE                       Location/Qualifiers
REGION                        1..17
                              note = CDR2 = hypervariable region 2 of heavy chain of
                              AIN457
source                        1..17
                              mol_type = protein
                              organism = synthetic construct
SEQUENCE: 2
AINQDGSEKY YVGSVKG                                                               17

SEQ ID NO: 3                  moltype = AA  length = 18
FEATURE                       Location/Qualifiers
REGION                        1..18
                              note = CDR3 = hypervariable region 3 of heavy chain of
                              AIN457
source                        1..18
                              mol_type = protein
                              organism = synthetic construct
SEQUENCE: 3
DYYDILTDYY IHYWYFDL                                                              18

SEQ ID NO: 4                  moltype = AA  length = 12
FEATURE                       Location/Qualifiers
REGION                        1..12
                              note = CDR1' = hypervariable region 1 of light chain of
                              AIN457
source                        1..12
                              mol_type = protein
                              organism = synthetic construct
SEQUENCE: 4
RASQSVSSSY LA                                                                    12

SEQ ID NO: 5                  moltype = AA  length = 7
FEATURE                       Location/Qualifiers
REGION                        1..7
```

```
                        note = CDR2' = hypervariable region 2 of light chain AIN457
source                  1..7
                        mol_type = protein
                        organism = synthetic construct
SEQUENCE: 5
GASSRAT                                                                               7

SEQ ID NO: 6            moltype = AA  length = 9
FEATURE                 Location/Qualifiers
REGION                  1..9
                        note = CDR3' = hypervariable region 3 of light chain AIN457
source                  1..9
                        mol_type = protein
                        organism = synthetic construct
SEQUENCE: 6
QQYGSSPCT                                                                             9

SEQ ID NO: 7            moltype = DNA  length = 381
FEATURE                 Location/Qualifiers
source                  1..381
                        mol_type = other DNA
                        organism = Homo sapiens
CDS                     1..381
SEQUENCE: 7
gaggtgcagt tggtggagtc tgggggaggc ttggtccagc ctggggggtc cctgagactc      60
tcctgtgcag cctctggatt cacctttagt aactattgga tgaactgggt ccgccaggct    120
ccagggaaag gctggagtg ggtgccgcc ataaaccaag atggaagtga aaatactat       180
gtgggctctg tgaagggccg attcaccatc tccagagaca cgccaagaa ctcactgtat     240
ctgcaaatga acagcctgag agtcgaggac acggctgtgt attactgtgt gagggactat   300
tacgatattt tgaccgatta ttacatccac tattggtact tcgatctctg gggccgtggc   360
accctggtca ctgtctcctc a                                              381

SEQ ID NO: 8            moltype = AA  length = 127
FEATURE                 Location/Qualifiers
source                  1..127
                        mol_type = protein
                        organism = Homo sapiens
SEQUENCE: 8
EVQLVESGGG LVQPGGSLRL SCAASGFTFS NYWMNWVRQA PGKGLEWVAA INQDGSEKYY     60
VGSVKGRFTI SRDNAKNSLY LQMNSLRVED TAVYYCVRDY YDILTDYYIH YWYFDLWGRG   120
TLVTVSS                                                              127

SEQ ID NO: 9            moltype = DNA  length = 327
FEATURE                 Location/Qualifiers
source                  1..327
                        mol_type = other DNA
                        organism = Homo sapiens
CDS                     1..327
SEQUENCE: 9
gaaattgtgt tgacgcagtc tccaggcacc ctgtctttgt ctccagggga aagagccacc     60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcaccgtg caccttcggc   300
caaggggaca cgactggaga taaacga                                        327

SEQ ID NO: 10           moltype = AA  length = 109
FEATURE                 Location/Qualifiers
source                  1..109
                        mol_type = protein
                        organism = Homo sapiens
SEQUENCE: 10
EIVLTQSPGT LSLSPGERAT LSCRASQSVS SSYLAWYQQK PGQAPRLLIY GASSRATGIP     60
DRFSGSGSGT DFTLTISRLE PEDFAVYYCQ QYGSSPCTFG QGTRLEIKR                109

SEQ ID NO: 11           moltype = AA  length = 10
FEATURE                 Location/Qualifiers
REGION                  1..10
                        note = CDR1-x = hypervariable domain x of heavy chain of
                        AIN457
source                  1..10
                        mol_type = protein
                        organism = synthetic construct
SEQUENCE: 11
GFTFSNYWMN                                                                           10

SEQ ID NO: 12           moltype = AA  length = 11
FEATURE                 Location/Qualifiers
REGION                  1..11
```

```
                        note = CDR2-x = hypervariable domain of heavy chain x of
                        AIN457
source                  1..11
                        mol_type = protein
                        organism = synthetic construct
SEQUENCE: 12
AINQDGSEKY Y                                                              11

SEQ ID NO: 13           moltype = AA  length = 23
FEATURE                 Location/Qualifiers
REGION                  1..23
                        note = CDR3-x = hypervariable domain x of heavy chain AIN457
source                  1..23
                        mol_type = protein
                        organism = synthetic construct
SEQUENCE: 13
CVRDYYDILT DYYIHYWYFD LWG                                                 23

SEQ ID NO: 14           moltype = AA  length = 215
FEATURE                 Location/Qualifiers
source                  1..215
                        mol_type = protein
                        organism = Homo sapiens
SEQUENCE: 14
EIVLTQSPGT LSLSPGERAT LSCRASQSVS SSYLAWYQQK PGQAPRLLIY GASSRATGIP          60
DRFSGSGSGT DFTLTISRLE PEDFAVYYCQ QYGSSPCTFG QGTRLEIKRT VAAPSVFIFP         120
PSDEQLKSGT ASVVCLLNNF YPREAKVQWK VDNALQSGNS QESVTEQDSK DSTYSLSSTL         180
TLSKADYEKH KVYACEVTHQ GLSSPVTKSF NRGEC                                   215

SEQ ID NO: 15           moltype = AA  length = 457
FEATURE                 Location/Qualifiers
source                  1..457
                        mol_type = protein
                        organism = Homo sapiens
SEQUENCE: 15
EVQLVESGGG LVQPGGSLRL SCAASGFTFS NYWMNWVRQA PGKGLEWVAA INQDGSEKYY          60
VGSVKGRFTI SRDNAKNSLY LQMNSLRVED TAVYYCVRDY YDILTDYYIH YWYFDLWGRG         120
TLVTVSSAST KGPSVFPLAP SSKSTSGGTA ALGCLVKDYF PEPVTVSWNS GALTSGVHTF         180
PAVLQSSGLY SLSSVVTVPS SSLGTQTYIC NVNHKPSNTK VDKRVEPKSC DKTHTCPPCP         240
APELLGGPSV FLFPPKPKDT LMISRTPEVT CVVVDVSHED PEVKFNWYVD GVEVHNAKTK         300
PREEQYNSTY RVVSVLTVLH QDWLNGKEYK CKVSNKALPA PIEKTISKAK GQPREPQVYT         360
LPPSREEMTK NQVSLTCLVK GFYPSDIAVE WESNGQPENN YKTTPPVLDS DGSFFLYSKL         420
TVDKSRWQQG NVFSCSVMHE ALHNHYTQKS LSLSPGK                                 457
```

PHARMACEUTICAL PRODUCTS AND STABLE LIQUID COMPOSITIONS OF IL-17 ANTIBODIES

RELATED APPLICATIONS

This application is a continuation of U.S. application Ser. No. 18/481,213, filed Oct. 4, 2023, which is a divisional of U.S. application Ser. No. 15/538,257, filed Jun. 21, 2017, which is a 371 Application of PCT Application PCT/IB2015/059836, filed Dec. 21, 2015, which claims priority to U.S. Provisional Patent Application No. 62/095,210, filed on Dec. 22, 2014, which is incorporated by reference herein in its entirety.

SEQUENCE LISTING

The instant application contains a Sequence Listing which has been submitted electronically in XML file format and is hereby incorporated by reference in its entirety. Said XML copy, created on Feb. 14, 2024, is named PAT056417-US-CNT_SL.xml and is 19,601 bytes in size.

TECHNICAL FIELD

The disclosure is directed to pharmaceutical products comprising stable liquid pharmaceutical compositions of IL-17 antibodies and antigen-binding fragments thereof, e.g., AIN457 (secukinumab), and processes of making such pharmaceutical products and liquid pharmaceutical compositions.

BACKGROUND OF THE DISCLOSURE

IL-17A is the central lymphokine of a newly defined subset of inflammatory T cells, the Th17 cells, which are pivotal in several autoimmune and inflammatory processes. IL-17A neutralization is expected to treat the underlying pathophysiology of immune mediated disease, and as a consequence provide relief of symptoms. Secukinumab (AIN457) is a high-affinity fully human monoclonal anti-human antibody that inhibits IL-17A activity, which has emerged as a potential treatment for patients with various autoimmune diseases, e.g., rheumatoid arthritis, ankylosing spondylitis, psoriatic arthritis, diabetes, asthma, chronic plaque-type psoriasis, and multiple sclerosis. Several Phase II and III studies have shown that secukinumab is superior to placebo in achievement of PASI 75 in treating chronic plaque-type psoriasis (e.g., secukinumab 3×150 mg and 3×75 mg were both superior to placebo in achievement of PASI 75 at Week 12 (81.5% and 57.1%, respectively, vs. 9.1%) in study CAIN457A2220. Secukinumab is currently used in global Phase III studies for the treatment of chronic plaque-type psoriasis, and has again shown superiority over placebo, and newly also over etanercept.

International Patent Application PCT/EP2011/069476 provides sucrose-based lyophilized compositions of secukinumab, which are reconstituted with 1 mL water immediately prior to use. However, PCT/EP2011/069476 provides no disclosure of a ready-to-use pharmaceutical product or liquid pharmaceutical composition of secukinumab having long-term stability. Indeed, the marginal stability of proteins in liquid compositions often prevents long-term storage at room temperature or refrigerated conditions. In addition, various physical and chemical reactions can occur in solution (aggregation [covalent and non-covalent], deamidation, oxidation, clipping, isomerization, denaturation), leading to an increase in degradation product levels and/or loss of bioactivity. A commercial ready-to-use liquid antibody composition should provide sufficient physical and chemical stability of the antibody during shipping and handling to ensure that the dosage and product safety claims are met when the molecule is administered to a patient. Specifically, an acceptable liquid antibody composition must enhance stability and minimize protein degradation, especially protein aggregation, in order to avoid serious immunogenic reactions. Moreover, the composition must also be of acceptable osmolality and pH value for subcutaneous application and have low viscosity as a prerequisite for manufacturing (compounding, filtration, filling) and syringeability. Balancing these myriad requirements is difficult, making the production of a commercially viable aqueous biopharmaceutical composition a technical challenge.

Regardless of the technical challenges outlined above, we have now successfully developed novel and beneficial ready-to-use pharmaceutical products and liquid pharmaceutical compositions of the IL-17 antibodies and antigen binding fragments disclosed herein, e.g., secukinumab.

BRIEF SUMMARY OF THE DISCLOSURE

The disclosure provides pharmaceutical products that include a container (e.g., pen, syringe, vial, autoinjector) having a headspace with less than about 12% oxygen (e.g., less than about 10% oxygen, less than about 8% oxygen, less than about 6% oxygen, etc.), and a liquid composition disposed within the container. The liquid composition is not reconstituted from a lyophilisate, but rather is a ready-to-use liquid composition and broadly includes at least one of the disclosed IL-17 antibodies or antigen binding fragments thereof (e.g., secukinumab), a buffer, a surfactant, methionine, and a stabilizer, as well as subcombinations thereof. We have determined that the combined use of particular stabilizers with a low oxygen level in the headspace of the container contributes significantly to long-term stability of the liquid pharmaceutical product, and prevents oxidation of the IL-17 antibody (e.g., secukinumab) included in the composition. These liquid compositions have excellent properties, e.g.:

after 13 months storage at 25° C., aggregate formation as measured by SEC of ≤3.5% for 2.5 mM methionine, ≤3.0% for 5 mM; and ≤2.2% for 20 mM methionine-containing compositions; and after 13 months storage at 25° C., degradation products by RP-HPLC (sum of variants before the main peak) of ≤39.4% for 2.5 mM, ≤37.8% for 5.0 mM, and ≤34.5% for 20 mM methionine-containing compositions.

Accordingly, disclosed herein are pharmaceutical products comprising: a container having a headspace, wherein the oxygen content in the headspace is less than about 12%, and a liquid pharmaceutical composition having a pH of about 5.2 to about 6.2 disposed within said container, said composition comprising: about 20 mg/ml to about 175 mg/ml secukinumab; and about 2.5 to about 20 mM L-methionine, wherein the liquid pharmaceutical composition is not reconstituted from a lyophilisate.

Also disclosed herein are pharmaceutical products comprising: a container having a headspace, wherein the oxygen content in the headspace is less than about 6%; and a liquid pharmaceutical composition disposed within said container, said composition comprising about 25 mg/mL to about 150 mg/mL of an IL-17 antibody disclosed herein (e.g., secukinumab), about 10 mM to about 30 mM histidine pH 5.8, about 200 mM to about 225 mM trehalose, about 0.02% polysorbate 80, and about 2.5 mM to about 20 mM methionine, wherein the liquid pharmaceutical composition is not reconstituted from a lyophilisate.

Also disclosed herein are processes for reducing the oxidation of secukinumab, comprising: preparing a liquid composition having a pH of about 5.2 to about 6.2 and comprising: about 25 mg/ml to about 150 mg/ml of an IL-17 antibody disclosed herein (e.g., secukinumab); and about 2.5 mM to about 20 mM methionine; disposing said liquid composition in a container having a headspace; and adjusting the oxygen content in the headspace to less than or equal to about 12%.

Also disclosed herein are stable liquid pharmaceutical compositions comprising about 25 mg/mL to about 150 mg/mL of an IL-17 antibody disclosed herein (e.g., secukinumab), about 10 mM to about 30 mM buffer (e.g., histidine) pH 5.8, about 200 mM to about 225 mM stabilizer (e.g., trehalose), about 0.02% surfactant (e.g., polysorbate 80), and about 2.5 mM to about 20 mM methionine.

The disclosure is also directed to the use of these pharmaceutical products and stable liquid compositions for the treatment of various IL-17-mediated disorders (e.g., autoimmune disorders, such as psoriasis, ankylosing spondylitis, psoriatic arthritis, and rheumatoid arthritis) and to kits containing these pharmaceutical products and stable liquid compositions.

Additional compositions, products, methods, regimens, uses, and kits are provided in the following description and appended claims. Further features, advantages and aspects of the present disclosure will become apparent to those skilled in the art from the following description and appended claims.

DETAILED DESCRIPTION OF THE DISCLOSURE

Figure 1A:
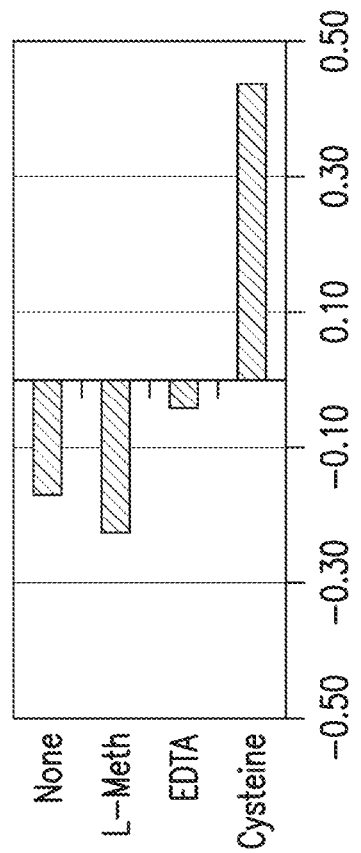
FIG. 1A-D show the impact of different anti-oxidative stabilizers on 150 mg/ml secukinumab liquid in syringe stability: parameter estimates for sub-visible particles 1 μm by light obscuration (particles/ml) after 8 weeks at 5° C. (A) pre-main peak species by RP-HPLC (%) after 8 weeks at 25° C. (B) DP-SEC (%) after 8 weeks at 40° C. (C.) AP-SEC (%) after 8 weeks at 40° C. (D).
Figure 1B:
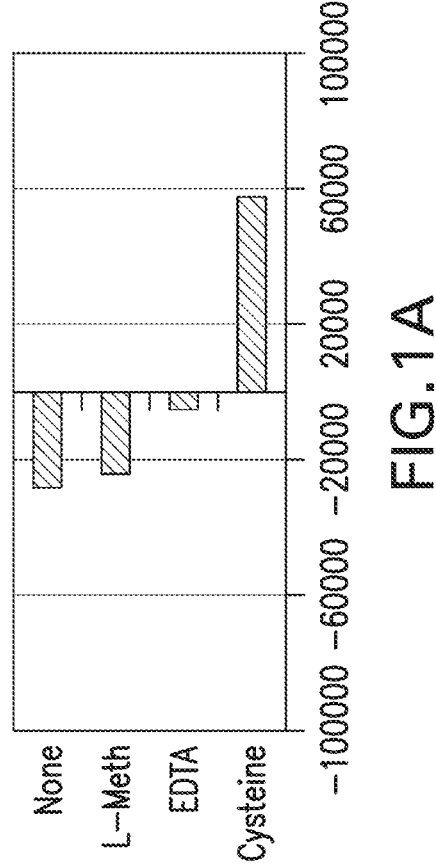
Figure 1C:
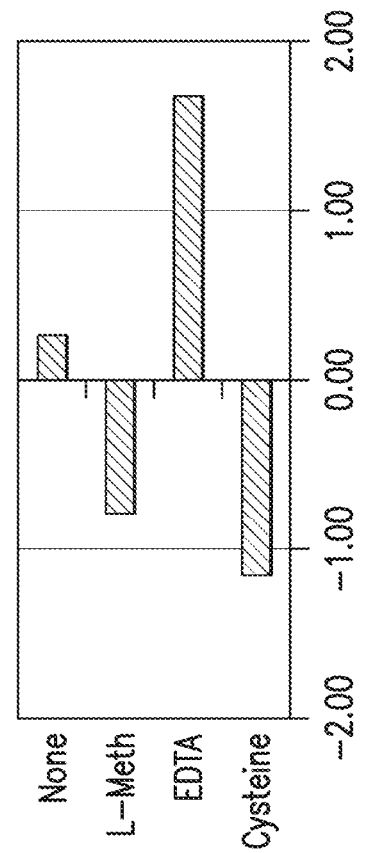
Figure 1D:
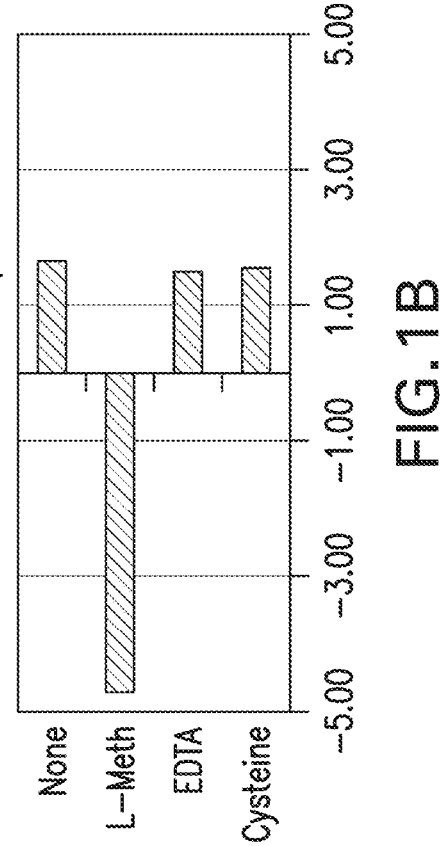

The term "comprising" encompasses "including" as well as "consisting," e.g. a composition "comprising" X may consist exclusively of X or may include something additional, e.g., X+Y.

The term "about" in relation to a numerical value x means +/−10% unless the context dictates otherwise.

By "monthly" is meant about every 4 weeks (e.g., every 4 weeks), which is about every 28 days (e.g., every 28 days).

The term "antibody" as referred to herein includes whole antibodies and any antigen-binding fragment or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed hypervariable regions or complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. In some embodiments of the disclosed methods, regimens, kits, processes, uses and compositions, an antibody to IL-17 or the IL-17 receptor is employed, preferably an antibody to IL-17, e.g., secukinumab.

An "isolated antibody", as used herein, refers to an antibody that is substantially free of other antibodies having different antigenic specificities (e.g., an isolated antibody that specifically binds IL-17 is substantially free of antibodies that specifically bind antigens other than IL-17). The term "monoclonal antibody" or "monoclonal antibody composition" as used herein refer to a preparation of antibody molecules of single molecular composition. The term "human antibody," as used herein, is intended to include antibodies having variable regions in which both the framework and CDR regions are derived from sequences of human origin. A "human antibody" need not be produced by a human, human tissue or human cell. The human antibodies of the disclosure may include amino acid residues not encoded by human sequences (e.g., mutations introduced by random or site-specific mutagenesis in vitro, by N-nucleotide addition at junctions in vivo during recombination of antibody genes, or by somatic mutation in vivo). In some embodiments of the disclosed methods, regimens, kits, processes, uses and compositions, the IL-17 antibody is a human antibody, an isolated antibody, and/or a monoclonal antibody.

The term "antigen-binding fragment" of an antibody as used herein, refers to fragments of an antibody that retain the ability to specifically bind to an antigen (e.g., IL-17). It has been shown that the antigen-binding function of an antibody can be performed by fragments of a full-length antibody. Examples of binding fragments encompassed within the term "antigen-binding fragment" of an antibody include a Fab fragment, a monovalent fragment consisting of the $V_L$, $V_H$, CL and CH1 domains; a F(ab)2 fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated CDR. Exemplary antigen binding sites include the CDRs of secukinumab as set forth in SEQ ID NOs: 1-6 and 11-13 (Table 1), preferably the heavy chain CDR3. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies are also intended to be encompassed within the term "antibody". Single chain antibodies and antigen-binding fragments are obtained using conventional techniques known to those of skill in the art. In some embodiments of the disclosed methods, regimens, kits, processes, uses and compositions, a single chain antibody or an antigen-binding fragment of an antibody against IL-17 (e.g., secukinumab) or the IL-17 receptor is employed.

The term "pharmaceutical product" means a container (e.g., pen, syringe, bag, pump, etc.) having a pharmaceutical composition disposed within said container. By "container" is meant any means for holding a liquid pharmaceutical composition, e.g., a pen, syringe, vial, autoinjector, patch, etc. Each container has a "headspace", i.e., an area within the container that does not contain the liquid pharmaceutical composition. This headspace contains gas, e.g., a mixture of oxygen and other gases normally found in air. The level of oxygen in the headspace may be regulated, e.g., by introducing an inert gas (e.g., nitrogen, argon, etc.) into the headspace in place of oxygen. This may be achieved actively, e.g., by purging, or passively, e.g., by placing a container in a system and removing the oxygen (e.g., by vacuum, etc.). Purging, e.g., using an inert gas, preferably nitrogen, may occur prior to filling of the composition into the container, during filling, or prior and during stopper placement. As used herein, the term "oxygen content in the headspace" refers to the percent oxygen found in the headspace of a given container.

A "stable" composition is one in which the protein therein essentially retains its stability, (e.g., physical, chemical and/or biological activity) upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993). Stability can be measured at a selected temperature for a selected time period. A "stable" liquid antibody composition is a liquid antibody composition with no significant changes observed at a refrigerated temperature (2-8° C.) for at least 6 months, 12 months, preferably 2 years, and more preferably 3 years; or at room temperature (23-27° C.) for at least 3 months, preferably 6 months, and more preferably 1 year, or at stressed conditions (~40° C.) for at least 1 month, preferably 3 months, and more preferably 6 months. Various stability criteria may be used, e.g., no more than 10%, preferably 5%, of antibody monomer is degraded (e.g., as measured by SEC Purity, RP-HPLC Purity, CEX Purity, CE-SDS Purity (non-reducing), etc.). Alternatively, stability may be shown if the solution remains clear to slightly opalescent by visual analysis or by using nephelometry. Alternatively, stability may be shown if concentration, pH and osmolality of the composition have no more than +/−10% variation over a given time period, e.g., at least 3 months, preferably 6 months, and more preferably 1 year Alternatively, stability may be shown if potency (e.g., as measured by biological activity in an inhibition or CEX assay, etc.) is within 70-130% (e.g., at least 70%, at least 75%, at least 76%, at least 80%, at least 90%, at least 91%, at least 95%), preferably 80-120% of a control over a given time period, e.g., at least 3 months, preferably 6 months, and more preferably 1 year. Alternatively, stability may be shown if no more than 10%, preferably 5% of clipping of the antibody is observed (e.g., as measured by DP-SEC, etc.) over a given time period, e.g., at least 3 months, preferably 6 months, and more preferably 1 year. Alternatively, stability may be shown if less than 10%, preferably less than 5% aggregates are formed (e.g., as measured by AP-SEC, etc.) over a given time period, e.g., at least 3 months, preferably 6 months, and more preferably 1 year Alternatively, stability may be shown if, after 13 months storage at 25° C., aggregate formation as measured by SEC is ≤ about 3.5%, ≤ about 3.0%; or ≤ about 2.2%. Alternatively, stability may be shown if, after 13 months storage at 25° C., degradation product formation (as measured by RP-HPLC (pre-main peak species)) is ≤ about 39.4%, ≤ about 37.8%, or ≤ about 34.5%.

An antibody retains its physical stability in a pharmaceutical composition if it shows no significant increase of aggregation, precipitation and/or denaturation upon visual examination of color and/or clarity (turbidity), or as measured by UV light scattering, size exclusion chromatography (SEC) and dynamic light scattering (DLS). In addition, the protein conformation should not be significantly altered, e.g., as evaluated by fluorescence spectroscopy (determines the protein tertiary structure) or by FTIR spectroscopy (determines the protein secondary structure).

An antibody retains its chemical stability in a pharmaceutical composition if it shows no significant chemical alteration. Chemical stability can be assessed by detecting and quantifying chemically altered forms of the protein. Degradation processes that often alter the protein chemical structure include hydrolysis or clipping (evaluated by methods such as size exclusion chromatography [SEC] and SDS-PAGE), oxidation (evaluated by methods such as by peptide mapping in conjunction with mass spectroscopy or MALDI/TOF/MS), deamidation (evaluated by methods such as cation-exchange chromatography (CEX), capillary isoelectric focusing, peptide mapping, isoaspartic acid measurement), and isomerization (evaluated by measuring the isoaspartic acid content, peptide mapping, etc.).

An antibody retains its biological activity in a pharmaceutical composition, if the biological activity of the protein/antibody at a given time is within a predetermined range of the biological activity exhibited at the time the pharmaceutical composition was prepared. The biological activity of an antibody can be determined, for example, by an antigen binding ELISA assay, potency assay (e.g., evaluating the ability of an IL-17 antibody (e.g., secukinumab) to bind IL-17 and inhibit IL-6 release from chondrocytes), or cysteamine-CEX derivitization.

As used herein, "purity by RP-HPLC" refers to the percentage of main peak in RP-HPLC and can be used to assess the stability of secukinumab. RP-HPLC is used to separate secukinumab and its variants according to their hydrophobicity. Pre-main peak species by RP-HPLC is the percentage sum of the peaks eluting prior to the main peak, which may contain fragmented, isomerized, and oxidized species of the antibody.

As used herein, "purity by CEX" refers to the percentage of main peak in CEX and can be used to assess the stability of secukinumab antibody. CEX is used to evaluate the charge heterogeneity of secukinumab by measuring the percentage of acidic and basic variants.

As used herein, "purity by SEC" refers to the percentage of monomer in SEC and can be used to assess the stability of secukinumab. SEC is used to separate monomeric secukinumab from aggregates and fragments according to their size under non-denaturing conditions. The sum of peaks eluting prior the main peak are reported as percentage of aggregation products (AP-SEC), the sum of peaks eluting after the main peak as percentage of degradation products (DP-SEC)

As used herein, "purity by CE-SDS" refers to the percentage of intact antibody in CE-SDS and can be used to assess the stability of secukinumab. CE-SDS is used to separate by- and degradation products from intact secukinumab according to their molecular size under non-reducing conditions. The sum of peaks separated from the main peak is reported as percentage of impurities.

The phrase "liquid pharmaceutical composition" as used herein refers to an aqueous composition that is not reconstituted from a lyophilisate and that contains at least one IL-17 antibody or antigen binding fragment thereof (e.g., secukinumab) and at least one additional excipient (e.g., a buffer). The liquid pharmaceutical composition may include additional excipients (stabilizers, surfactants) and additional active ingredients. This type of formulation is also referred to as a "ready-to-use" formulation.

As used herein, the term "lyophilisate" refers to dried (e.g., freeze dried) pharmaceutical compositions largely devoid of water. Techniques for lyophilisation of antibodies are well known in the art, e.g., see Rey & May (2004) Freeze-Drying/Lyophilization of Pharmaceutical & Biological Products ISBN 0824748689. Lyophilisates are reconstituted to give aqueous compositions—usually for immediate use (e.g., within 1-10 days)—as reconstituted lyophilisates tend to have a limited shelf lives.

The term "high concentration" refers to a composition containing greater than 50 mg/ml antibody or antigen binding fragment thereof. In preferred embodiments, a high concentration liquid composition contains ≥ about 50 mg/ml, ≥ about 75 mg/ml, ≥ about 100 mg/ml, ≥ about 125 mg/ml, ≥ about 150 mg/ml, ≥ about 175 mg/ml, ≥ about 200 mg/ml, or ≥ about 225 mg/ml.

The term "IL-17" refers to IL-17A, formerly known as CTLA8, and includes wild-type IL-17A from various species (e.g., human, mouse, and monkey), polymorphic variants of IL-17A, and functional equivalents of IL-17A. Functional equivalents of IL-17A according to the present disclosure preferably have at least about 65%, 75%, 85%, 95%, 96%, 97%, 98%, or even 99% overall sequence identity with a wild-type IL-17A (e.g., human IL-17A), and substantially retain the ability to induce IL-6 production by human dermal fibroblasts.

The term "$K_D$" is intended to refer to the dissociation rate of a particular antibody-antigen interaction. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system. In some embodiments, the IL-17 antibody or antigen binding fragment thereof binds human IL-17 with a $K_D$ of about 100-250 pM (as measured by Biacore®).

The term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. Standard assays to evaluate the binding affinity of the antibodies toward IL-17 of various species are known in the art, including for example, ELISAs, western blots and RIAs. The binding kinetics (e.g., binding affinity) of the antibodies also can be assessed by standard assays known in the art, such as by Biacore® analysis.

As used herein, the terms "subject" and "patient" include any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

An antibody that "inhibits" one or more of these IL-17 functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (or when a control antibody of irrelevant specificity is present). An antibody that inhibits IL-17 activity affects a statistically significant decrease, e.g., by at least about 10% of the measured parameter, by at least 50%, 80% or 90%, and in certain embodiments of the disclosed methods, uses, processes, kits and compositions, the IL-17 antibody used may inhibit greater than 95%, 98% or 99% of IL-17 functional activity.

"Inhibit IL-6" as used herein refers to the ability of an IL-17 antibody (e.g., secukinumab) to decrease IL-6 production from chondrocytes. The biological activity of the IL-17 antibody or antigen binding fragment thereof, e.g., secukinumab, may be measured based on its capacity to inhibit the IL-17-induced release of IL-6 from an immortalized human chondrocyte cell line, e.g., C-20/A4. In brief, on the first day of the assay, C-20/A4 cells are seeded into 96-well plates, are allowed to attach, and are then incubated overnight in the presence of a fixed, sub-maximal concentration of IL-17 (e.g., at about 20-200 ng/mL, e.g., about 80 ng/mL, in the culture medium) and various concentrations of antibody (e.g., at about 0.01 ug/mL-about 4 ug/mL, e.g., about 0.5 µg/mL-about 2 µg/mL, in the assay plate). TNFalfa, which facilitates IL-17-induced IL-6 production, is included (e.g., at about 0.01 ng/ml-about 1 ng/mL, e.g., about 0.5 ng/mL, in the culture medium) to increase the dynamic range of the assay. On the second day, the concentration of IL-6 in the cell supernatants is quantified by ELISA. The amount of IL-6 in the cell supernatants is inversely proportional to the activity of the IL-17 antibody present in the sample. The biological activity of an antibody test sample is quantified by comparing its ability to inhibit IL-17-dependent release of IL-6 to that of an antibody reference standard. The samples and standard are normalized on the basis of protein content. Relative potency is calculated using a parallel line assay according to the European Pharmacopoeia. The final result is expressed as relative potency (in percent) of a sample compared to the reference standard.

The term "derivative", unless otherwise indicated, is used to define amino acid sequence variants, and covalent modifications (e.g., pegylation, deamidation, hydroxylation, phosphorylation, methylation, etc.) of an IL-17 antibody or antigen binding fragment thereof, e.g., secukinumab, according to the present disclosure, e.g., of a specified sequence (e.g., a variable domain). A "functional derivative" includes a molecule having a qualitative biological activity in common with the disclosed IL-17 antibodies or antigen binding fragments thereof. A functional derivative includes fragments and peptide analogs of an IL-17 antibody or antigen binding fragment thereof as disclosed herein. Fragments comprise regions within the sequence of a polypeptide according to the present disclosure, e.g., of a specified sequence. Functional derivatives of the IL-17 antibodies or antigen binding fragments thereof disclosed herein (e.g., functional derivatives of secukinumab) preferably comprise $V_H$ and/or $V_L$ domains that have at least about 65%, 75%, 85%, 95%, 96%, 97%, 98%, or even 99% overall sequence identity with the $V_H$ and/or $V_L$ sequences of the IL-17 binding molecules disclosed herein (e.g., the $V_H$ and/or $V_L$ sequences of Table 1), and substantially retain the ability to bind human IL-17 or, e.g., inhibit IL-6 production of IL-17 induced human dermal fibroblasts.

The phrase "substantially identical" means that the relevant amino acid or nucleotide sequence (e.g., $V_H$ or $V_L$, domain) will be identical to or have insubstantial differences (e.g., through conserved amino acid substitutions) in comparison to a particular reference sequence. Insubstantial differences include minor amino acid changes, such as 1 or 2 substitutions in a 5 amino acid sequence of a specified region (e.g., $V_H$ or $V_L$ domain). In the case of antibodies, the second antibody bas the same specificity and has at least 50% of the affinity of the same. Sequences substantially identical (e.g., at least about 85% sequence identity) to the sequences disclosed herein are also part of this application. In some embodiments, the sequence identity of a derivative IL-17 antibody (e.g., a derivative of secukinumab, e.g., a secukinumab biosimilar antibody) can be about 90% or greater, e.g., 90%, 91%, 92%, 93%, 94%, 95%, 96%, 97%, 98%, 99% or higher relative to the disclosed sequences.

"Identity" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent identity, and not considering any conservative substitutions as part of the sequence identity. Neither N- or C-terminal extensions nor insertions shall be construed as reducing identity. Methods and computer programs for the alignment are well known. The percent identity can be determined by standard alignment algorithms, for example, the Basic Local Alignment Search Tool (BLAST) described by Altshul et al. ((1990) J. Mol. Biol., 215:403 410); the algorithm of Needleman et al. ((1970) J. Mol. Biol., 48:444 453); or the algorithm of Meyers et al. ((1988) Comput. Appl. Biosci., 4:11 17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller ((1989) CABIOS, 4:11-17) which has been incorporated into the ALIGN program (version 2.0), using a PAM 120 weight residue table, a gap length penalty of 12 and a gap penalty of 4.

"Amino acid(s)" refer to all naturally occurring L-α-amino acids, e.g., and include D-amino acids. The phrase "amino acid sequence variant" refers to molecules with some differences in their amino acid sequences as compared to the sequences according to the present disclosure. Amino acid sequence variants of a polypeptide according to the present disclosure, e.g., of a specified sequence, still have the ability to bind the human IL-17 or, e.g., inhibit IL-6 production of IL-17 induced human dermal fibroblasts. Amino acid sequence variants include substitutional variants (those that have at least one amino acid residue removed and a different amino acid inserted in its place at the same position in a polypeptide according to the present disclosure), insertional variants (those with one or more amino acids inserted immediately adjacent to an amino acid at a particular position in a polypeptide according to the present disclosure) and deletional variants (those with one or more amino acids removed in a polypeptide according to the present disclosure).

The term "pharmaceutically acceptable" means a non-toxic material that does not interfere with the effectiveness of the biological activity of the active ingredient(s).

The term "administering" in relation to a compound, e.g., an IL-17 binding molecule or another agent, is used to refer to delivery of that compound to a patient by any route.

As used herein, a "therapeutically effective amount" refers to an amount of an IL-17 antibody or antigen binding fragment thereof, e.g., secukinumab, that is effective, upon single or multiple dose administration to a patient (such as a human) for treating, preventing, preventing the onset of, curing, delaying, reducing the severity of, ameliorating at least one symptom of a disorder or recurring disorder, or prolonging the survival of the patient beyond that expected in the absence of such treatment. When applied to an individual active ingredient (e.g., an IL-17 antibody, e.g., secukinumab) administered alone, the term refers to that ingredient alone. When applied to a combination, the term refers to combined amounts of the active ingredients that result in the therapeutic effect, whether administered in combination, serially or simultaneously.

The term "treatment" or "treat" refer to both prophylactic or preventative treatment as well as curative or disease modifying treatment, including treatment of a patient at risk of contracting the disease or suspected to have contracted the disease as well as patients who are ill or have been diagnosed as suffering from a disease or medical condition, and includes suppression of clinical relapse. The treatment may be administered to a patient having a medical disorder or who ultimately may acquire the disorder, in order to prevent, cure, delay the onset of, reduce the severity of, or ameliorate one or more symptoms of a disorder or recurring disorder, or in order to prolong the survival of a patient beyond that expected in the absence of such treatment.

The phrase "means for administering" is used to indicate any available implement for systemically administering a drug to a patient, including, but not limited to, a pre-filled syringe, a vial and syringe, an injection pen, an autoinjector, an i.v. drip and bag, a pump, a patch pump, etc. With such items, a patient may self-administer the drug (i.e., administer the drug on their own behalf) or a physician may administer the drug. Typically, dosages given in "mg/kg" are administered via an i.v. route, and doses given in "mg" are administered via i.m. or s.c. injections. In some embodiments of the disclosed methods, kits, regimens and uses, the IL-17 antibody or antigen binding fragment thereof, e.g., secukinumab, is delivered to the patient via the i.v. route. In some embodiments of the disclosed methods, kits, regimens and uses, the IL-17 antibody or antigen binding fragment thereof, e.g., secukinumab, is delivered to the patient via the s.c. route.

IL-17 Antibodies and Antigen Binding Fragments Thereof

The disclosed pharmaceutical products, compositions, liquid compositions, regimens, processes, uses, methods and kits contain or utilize an IL-17 antibody or antigen binding fragment thereof.

In one embodiment, the IL-17 antibody or antigen binding fragment thereof, e.g., secukinumab, comprises at least one immunoglobulin heavy chain variable domain ($V_H$) comprising hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3. In one embodiment, the IL-17 antibody or antigen binding fragment thereof, e.g., secukinumab, comprises at least one immunoglobulin light chain variable domain ($V_L$) comprising hypervariable regions CDR1', CDR2' and CDR3', said CDR1' having the amino acid sequence SEQ ID NO:4, said CDR2' having the amino acid sequence SEQ ID NO:5 and said CDR3' having the amino acid sequence SEQ ID NO:6. In one embodiment, the IL-17 antibody or antigen binding fragment thereof, e.g., secukinumab, comprises at least one immunoglobulin heavy chain variable domain ($V_H$) comprising hypervariable regions CDR1-x, CDR2-x and CDR3-x, said CDR1-x having the amino acid sequence SEQ ID NO:11, said CDR2-x having the amino acid sequence SEQ ID NO: 12, and said CDR3-x having the amino acid sequence SEQ ID NO: 13.

In one embodiment, the IL-17 antibody or antigen binding fragment thereof, e.g., secukinumab, comprises at least one immunoglobulin $V_H$ domain and at least one immunoglobulin $V_L$ domain, wherein: a) the immunoglobulin $V_H$ domain comprises (e.g., in sequence): i) hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3; or ii) hypervariable regions CDR1-x, CDR2-x and CDR3-x, said CDR1-x having the amino acid sequence SEQ ID NO:11, said CDR2-x having the amino acid sequence SEQ ID NO: 12, and said CDR3-x having the amino acid sequence SEQ ID NO:13; and b) the immunoglobulin $V_L$ domain comprises (e.g., in sequence) hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6.

In one embodiment, the IL-17 antibody or antigen binding fragment thereof, e.g., secukinumab, comprises: a) an immunoglobulin heavy chain variable domain ($V_H$) comprising the amino acid sequence set forth as SEQ ID NO:8; b) an immunoglobulin light chain variable domain ($V_L$) comprising the amino acid sequence set forth as SEQ ID NO:10; c) an immunoglobulin $V_H$ domain comprising the amino acid sequence set forth as SEQ ID NO:8 and an immunoglobulin $V_L$ domain comprising the amino acid sequence set forth as SEQ ID NO:10; d) an immunoglobulin $V_H$ domain comprising the hypervariable regions set forth as SEQ ID NO: 1, SEQ ID NO:2, and SEQ ID NO:3; e) an immunoglobulin $V_L$ domain comprising the hypervariable regions set forth as SEQ ID NO:4, SEQ ID NO:5 and SEQ ID NO:6; f) an immunoglobulin $V_H$ domain comprising the hypervariable regions set forth as SEQ ID NO:11, SEQ ID NO:12 and SEQ ID NO:13; g) an immunoglobulin $V_H$ domain comprising the hypervariable regions set forth as SEQ ID NO: 1, SEQ ID NO: 2, and SEQ ID NO:3 and an immunoglobulin $V_L$ domain comprising the hypervariable regions set forth as SEQ ID NO:4, SEQ ID NO:5 and SEQ ID NO:6; or h) an immunoglobulin $V_H$ domain comprising the hypervariable regions set forth as SEQ ID NO: 11, SEQ ID NO: 12 and SEQ ID NO: 13 and an immunoglobulin $V_L$ domain comprising the hypervariable regions set forth as SEQ ID NO:4, SEQ ID NO:5 and SEQ ID NO:6.

For ease of reference the amino acid sequences of the hypervariable regions of the secukinumab monoclonal antibody, based on the Kabat definition and as determined by the X-ray analysis and using the approach of Chothia and coworkers, is provided in Table 1, below.

TABLE 1

Amino acid sequences of the hypervariable regions of the secukinumab monoclonal antibodies.

| | | Light-Chain |
|---|---|---|
| CDR1' | Kabat | R-A-S-Q-S-V-S-S-S-Y-L-A (SEQ ID NO: 4) |
| | Chothia | R-A-S-Q-S-V-S-S-S-Y-L-A (SEQ ID NO: 4) |
| CDR2' | Kabat | G-A-S-S-R-A-T (SEQ ID NO: 5) |
| | Chothia | G-A-S-S-R-A-T (SEQ ID NO: 5) |

TABLE 1-continued

Amino acid sequences of the hypervariable regions of the secukinumab monoclonal antibodies.

| | | |
|---|---|---|
| CDR2' | Kabat | Q-Q-Y-G-S-S-P-C-T (SEQ ID NO: 6) |
| | Chothia | Q-Q-Y-G-S-S-P-C-T (SEQ ID NO: 6) |

Heavy-Chain

| | | |
|---|---|---|
| CDR1 | Kabat | N-Y-W-M-N (SEQ ID NO: 1) |
| CDR1-x | Chothia | G-F-T-F-S-N-Y-W-M-N (SEQ ID NO: 11) |
| CDR2 | Kabat | A-I-N-Q-D-G-S-E-K-Y-Y-V-G-S-V-K-G (SEQ ID NO: 2) |
| CDR2-x | Chothia | A-I-N-Q-D-G-S-E-K-Y-Y (SEQ ID NO: 12) |
| CDR3 | Kabat | D-Y-Y-D-I-L-T-D-Y-Y-I-H-Y-W-Y-F-D-L (SEQ ID NO: 3) |
| CDR3-x | Chothia | C-V-R-D-Y-Y-D-I-L-T-D-Y-Y-I-H-Y-W-Y-F-D-L-W-G (SEQ ID NO: 13) |

In preferred embodiments, the constant region domains preferably also comprise suitable human constant region domains, for instance as described in "Sequences of Proteins of Immunological Interest", Kabat E. A. et al, US Department of Health and Human Services, Public Health Service, National Institute of Health. The DNA encoding the VL of secukinumab is set forth in SEQ ID NO:9. The DNA encoding the VH of secukinumab is set forth in SEQ ID NO: 7.

In some embodiments, the IL-17 antibody or antigen binding fragment thereof, e.g., secukinumab, comprises the three CDRs of SEQ ID NO: 10. In other embodiments, the IL-17 antibody comprises the three CDRs of SEQ ID NO:8. In other embodiments, the IL-17 antibody comprises the three CDRs of SEQ ID NO: 10 and the three CDRs of SEQ ID NO:8. CDRs of SEQ ID NO:8 and SEQ ID NO:10, according to both the Chothia and Kabat definition, may be found in Table 1.

In some embodiments, the IL-17 antibody or antigen binding fragment thereof, e.g., secukinumab, comprises the light chain of SEQ ID NO:14. In other embodiments, the IL-17 antibody or antigen binding fragment thereof, e.g., secukinumab, comprises the heavy chain of SEQ ID NO:15. In other embodiments, the IL-17 antibody or antigen binding fragment thereof, e.g., secukinumab, comprises the light chain of SEQ ID NO: 14 and the heavy chain of SEQ ID NO:15. In some embodiments, the IL-17 antibody or antigen binding fragment thereof, e.g., secukinumab, comprises the three CDRs of SEQ ID NO:14. In other embodiments, the IL-17 antibody or antigen binding fragment thereof, e.g., secukinumab, comprises the three CDRs of SEQ ID NO:15. In other embodiments, the IL-17 antibody or antigen binding fragment thereof, e.g., secukinumab, comprises the three CDRs of SEQ ID NO: 14 and the three CDRs of SEQ ID NO:15. CDRs of SEQ ID NO:15 and SEQ ID NO:17, according to both the Chothia and Kabat definition, may be found in Table 1.

Hypervariable regions may be associated with any kind of framework regions, though preferably are of human origin. Suitable framework regions are described in Kabat E. A. et al, ibid. The preferred heavy chain framework is a human heavy chain framework, for instance that of the secukinumab antibody. It consists in sequence, e.g. of FR1 (amino acid 1 to 30 of SEQ ID NO: 8), FR2 (amino acid 36 to 49 of SEQ ID NO:8), FR3 (amino acid 67 to 98 of SEQ ID NO:8) and FR4 (amino acid 117 to 127 of SEQ ID NO:8) regions. Taking into consideration the determined hypervariable regions of secukinumab by X-ray analysis, another preferred heavy chain framework consists in sequence of FR1-x (amino acid 1 to 25 of SEQ ID NO:8), FR2-x (amino acid 36 to 49 of SEQ ID NO:8), FR3-x (amino acid 61 to 95 of SEQ ID NO:8) and FR4 (amino acid 119 to 127 of SEQ ID NO:8) regions. In a similar manner, the light chain framework consists, in sequence, of FR1' (amino acid 1 to 23 of SEQ ID NO: 10), FR2' (amino acid 36 to 50 of SEQ ID NO:10), FR3' (amino acid 58 to 89 of SEQ ID NO:10) and FR4' (amino acid 99 to 109 of SEQ ID NO:10) regions.

In one embodiment, the IL-17 antibody or antigen binding fragment thereof, e.g., secukinumab, is selected from a human anti IL-17 antibody which comprises at least: a) an immunoglobulin heavy chain or fragment thereof which comprises a variable domain comprising, in sequence, the hypervariable regions CDR1, CDR2 and CDR3 and the constant part or fragment thereof of a human heavy chain; said CDR1 having the amino acid sequence SEQ ID NO:1, said CDR2 having the amino acid sequence SEQ ID NO:2, and said CDR3 having the amino acid sequence SEQ ID NO:3; and b) an immunoglobulin light chain or fragment thereof which comprises a variable domain comprising, in sequence, the hypervariable regions CDR1', CDR2', and CDR3' and the constant part or fragment thereof of a human light chain, said CDR1' having the amino acid sequence SEQ ID NO: 4, said CDR2' having the amino acid sequence SEQ ID NO:5, and said CDR3' having the amino acid sequence SEQ ID NO: 6.

In one embodiment, the IL-17 antibody or antigen binding fragment thereof, e.g., secukinumab, is selected from a single chain binding molecule which comprises an antigen binding site comprising: a) a first domain comprising, in sequence, the hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3; and b) a second domain comprising, in sequence, the hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6; and c) a peptide linker which is bound either to the N-terminal extremity of the first domain and to the C-terminal extremity of the second domain or to the C-terminal extremity of the first domain and to the N-terminal extremity of the second domain.

Alternatively, the IL-17 antibody or antigen binding fragment thereof, e.g., secukinumab, for use in the disclosed methods may comprise a derivative of the molecules set forth herein by sequence (e.g., a pegylated version of secukinumab). Alternatively, the $V_H$ or $V_L$ domain of the IL-17 antibody or antigen binding fragment thereof, e.g., secukinumab, for use in the disclosed methods may have $V_H$ or $V_L$ domains that are substantially identical to the $V_H$ or $V_L$ domains set forth herein (e.g., those set forth in SEQ ID NO:8 and 10). A human IL-17 antibody disclosed herein may comprise a heavy chain that is substantially identical to that set forth as SEQ ID NO:15 and/or a light chain that is substantially identical to that set forth as SEQ ID NO: 14. A human IL-17 antibody disclosed herein may comprise a heavy chain that comprises SEQ ID NO:15 and a light chain that comprises SEQ ID NO:14. A human IL-17 antibody disclosed herein may comprise: a) one heavy chain which comprises a variable domain having an amino acid sequence substantially identical to that shown in SEQ ID NO:8 and the constant part of a human heavy chain; and b) one light chain which comprises a variable domain having an amino acid sequence substantially identical to that shown in SEQ ID NO: 10 and the constant part of a human light chain. Alternatively, the IL-17 antibody or antigen binding fragment thereof, e.g., secukinumab, for use in the disclosed methods may be an amino acid sequence variant of the reference molecules set forth herein. In all such cases of derivative and variants, the IL-17 antibody or antigen binding fragment thereof, e.g., secukinumab, is capable of inhibiting the activity of about 1 nM (=30 ng/ml) human IL-17 at a concentration of about 50 nM or less, about 20 nM or less, about 10 nM or less, about 5 nM or less, about 2 nM or less, or more preferably of about 1 nM or less of said molecule by 50%, said inhibitory activity being measured on IL-6 production induced by hu-IL-17 in human dermal fibroblasts.

The inhibition of the binding of IL-17 to its receptor may be conveniently tested in various assays including such assays as described in WO 2006/013107. By the term "to the same extent" is meant that the reference and the derivative molecules exhibit, on a statistical basis, essentially identical IL-17 inhibitory activity in one of the assays referred to herein (see Example 1 of WO 2006/013107). For example, the IL-17 antibody or antigen binding fragment thereof disclosed herein typically have $IC_{50}$s for the inhibition of human IL-17 on IL-6 production induced by human IL-17 in human dermal fibroblasts which are below about 10 nM, more preferably about 9, 8, 7, 6, 5, 4, 3, 2, or about 1 nM of that of, preferably substantially the same as, the $IC_{50}$ of the corresponding reference molecule when assayed as described in Example 1 of WO 2006/013107. Alternatively, the assay used may be an assay of competitive inhibition of binding of IL-17 by soluble IL-17 receptors (e.g. the human IL-17 R/Fc constructs of Example 1 of WO 2006/013107) and the IL-17 antibodies or antigen binding fragments thereof of the disclosure.

The disclosure also includes IL-17 antibodies or antigen binding fragments thereof, e.g., secukinumab, in which one or more of the amino acid residues of the $V_H$ or $V_L$ domain, typically only a few (e.g., 1-10), are changed relative to the $V_H$ or $V_L$ domain set forth as SEQ ID NO:8 and SEQ ID NO:10; for instance by mutation, e.g., site directed mutagenesis of the corresponding DNA sequences. The disclosure includes the DNA sequences coding for such changed IL-17 antibodies.

The disclosure also includes IL-17 antibodies or antigen binding fragments thereof, e.g., secukinumab, that have binding specificity for human IL-17, in particular IL-17 antibodies capable of inhibiting the binding of IL-17 to its receptor and IL-17 antibodies capable of inhibiting the activity of 1 nM (=30 ng/ml) human IL-17 at a concentration of about 50 nM or less, about 20 nM or less, about 10 nM or less, about 5 nM or less, about 2 nM or less, or more preferably of about 1 nM or less of said molecule by 50% (said inhibitory activity being measured on IL-6 production induced by hu-IL-17 in human dermal fibroblasts).

In some embodiments, the IL-17 antibody, e.g., secukinumab, binds to an epitope of mature human IL-17 comprising Leu74, Tyr85, His86, Met87, Asn88, Val124, Thr125, Pro126, Ile127, Val128, His129. In some embodiments, the IL-17 antibody, e.g., secukinumab, binds to an epitope of mature human IL-17 comprising Tyr43, Tyr44, Arg46, Ala79, Asp80. In some embodiments, the IL-17 antibody, e.g., secukinumab, binds to an epitope of an IL-17 homodimer having two mature human IL-17 chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain. The residue numbering scheme used to define these epitopes is based on residue one being the first amino acid of the mature protein (ie., IL-17A lacking the 23 amino acid N-terminal signal peptide and beginning with Glycine). The sequence for immature IL-17A is set forth in the Swiss-Prot entry Q16552. In some embodiments, the IL-17 antibody has a $K_D$ of about 100-200 pM, e.g., as measured by Biacore®. In some embodiments, the IL-17 antibody has an $IC_{50}$ of about 0.4 nM for in vitro neutralization of the biological activity of about 0.67 nM human IL-17A. In some embodiments, the absolute bioavailability of subcutaneously (s.c.) administered IL-17 antibody has a range of about 60-about 80%, e.g., about 76%. In some embodiments, the IL-17 antibody, such as secukinumab, has an elimination half-life of about 4 weeks (e.g., about 23 to about 35 days, about 23 to about 30 days, e.g., about 30 days). In some embodiments, the IL-17 antibody, such as secukinumab, has a $T_{max}$ of about 7-8 days.

Particularly preferred IL-17 antibodies or antigen binding fragments thereof, e.g., secukinumab, for use in the disclosed methods, uses, kits, etc. are human antibodies, especially secukinumab as described in Examples 1 and 2 of WO 2006/013107 (U.S. Pat. No. 7,807,155, which is incorporated by reference herein in its entirety). Secukinumab is a recombinant high-affinity, fully human monoclonal anti-human interleukin-17A (IL-17A, IL-17) antibody of the IgG1/kappa isotype that is currently in clinical trials for the treatment of immune-mediated inflammatory conditions Secukinumab (see, e.g., WO2006/013107 and WO2007/117749) has a very high affinity for IL-17, i.e., a $K_D$ of about 100-200 pM (e.g., as measured by Biacore®) and an $IC_{50}$ for in vitro neutralization of the biological activity of about 0.67 nM human IL-17A of about 0.4 nM. Thus, secukinumab inhibits antigen at a molar ratio of about 1:1. This high binding affinity makes the secukinumab antibody particularly suitable for therapeutic applications. Furthermore, it has been determined that secukinumab has a very long half-life, i.e., about 4 weeks, which allows for prolonged periods between administration, an exceptional property when treating chronic life-long disorders, such as psoriasis.

Pharmaceutical Products Comprising IL-17 Antibodies or Antigen Binding Fragments The disclosure broadly provides a pharmaceutical product including a container having a headspace with less than about 12% oxygen in the headspace, and a liquid composition disposed within the container, wherein said liquid composition comprises the aforementioned IL-17 antibodies or antigen binding fragments thereof, e.g., secukinumab.

Containers

The pharmaceutical products of the disclosure employ primary packaging, i.e., containers, to store, transport, and maintain the disclosed liquid compositions. Pharmaceutically acceptable containers for use as part of the disclosed pharmaceutical products include syringes (e.g., available from Beckton Dickinson, Nuova Ompi, et al.), stoppered vials, cartridges, autoinjectors, patch pumps and injector pens.

Headspace Oxygen

We have determined that stability of the IL-17 antibody or antigen binding fragment thereof (e.g., secukinumab) in the disclosed liquid composition can be enhanced by including a particular stabilizer (e.g., methionine) while concurrently replacing the oxygen in the container headspace of the pharmaceutical product with an inert gas (e.g., argon, helium, nitrogen), preferably $N_2$. Specifically, we have determined that pharmaceutical products having a container that has been purged of oxygen, i.e., having less than about 12% oxygen in the headspace, have improved stability relative to unpurged products, e.g., as measured by SEC and RP-HPLC.

Modification of the oxygen content in the headspace using a purge (e.g., nitrogen purge) may be achieved during the filling stage or during the stoppering stage (or both). A purge (e.g., nitrogen purge) may be achieved by actively introducing the inert gas (e.g., using a needle) or during stoppering.

In some embodiments, the oxygen content in the headspace is less than about 12% (e.g., less than about 10%, less than about 8%, less than about 6%, etc.). In some embodiments, the oxygen content in the headspace is less than about 6%. The oxygen content in the headspace may be monitored by laser light absorption spectroscopy or fluorescence quenching or gas chromatography. It will be understood that the oxygen content in the headspace of a given container may increase over time, e.g., due to leakage. Thus, as used herein the phrase "the oxygen content in the headspace" refers to the initial level of oxygen in the headspace of a container immediately following closure (e.g., stoppering) of the product.

Liquid Compositions

A liquid composition of the disclosure comprises at least one of the IL-17 antibodies or antigen binding fragments thereof (e.g., secukinumab), which are described supra, and at least one additional excipient, e.g., buffer, surfactant, and stabilizer(s), etc. In some embodiments, the liquid composition comprises at least two additional excipients, e.g., a buffer and a stabilizer. In some embodiments, the liquid composition comprises a buffer, at least one stabilizer, and a surfactant.

In general, a pharmaceutical composition will be formulated with excipients that are compatible with the intended route of administration (e.g., oral compositions generally include an inert diluent or an edible carrier). Examples of routes of administration include parenteral (e.g., intravenous), intradermal, subcutaneous, oral (e.g., by mouth or inhalation), transdermal (topical), transmucosal, and rectal. The liquid antibody compositions of this disclosure are suitable for parenteral administration such as intravenous, intramuscular, intraperitoneal, or subcutaneous injection; particularly suitable for subcutaneous injection.

In some embodiments, a liquid composition of the disclosure maintains at least about 86% purity by RP-HPLC upon storage at 2-8° C. for 6 months, at least about 76% purity by RP-HPLC upon storage at 25° C./60% RH for 6 months (preferably at least about 76%), and/or at least about 60% purity by RP-HPLC upon storage at 30° C./75% RH for 6 months. In some embodiments, a liquid composition of the disclosure maintains at least about 84% purity by RP-HPLC upon storage at 2-8° C. for 24 months.

In some embodiments, a liquid composition of the disclosure maintains at least about 77% purity by CEX upon storage at 2-8° C. for 6 months, at least about 62% purity by CEX upon storage at 25° C./60% RH for 6 months, and/or at least about 50% purity by CEX upon storage at 30° C./75% RH for 6 months. In some embodiments, a liquid composition of the disclosure maintains at least about 73% purity by CEX upon storage at 2-8° C. for 24 months.

In some embodiments, a liquid composition of the disclosure maintains at least about 98% purity by SEC upon storage at 2-8° C. for 6 months, at least about 96% purity by SEC upon storage at 25° C./60% RH for 6 months, and/or at least about 94% purity by SEC upon storage at 30° C./75% RH for 6 months. In some embodiments, a liquid composition of the disclosure maintains at least about 97% purity by SEC upon storage at 2-8° C. for 24 months.

In some embodiments, a liquid composition of the disclosure maintains at least about 97% purity by CE-SDS (non-reducing conditions) upon storage at 2-8° C. for 6 months, at least about 95% purity by CE-SDS (non-reducing conditions) upon storage at 25° C./60% RH for 6 months, and/or at least about 94% (preferably at least about 92%) purity by CE-SDS (non-reducing conditions) upon storage at 30° C./75% RH for 6 months. In some embodiments, a liquid composition of the disclosure maintains at least about 97% purity by CE-SDS (non-reducing conditions) upon storage at 2-8° C. for 24 months.

In some embodiments, a liquid composition of the disclosure maintains less than about 0.57% impurity by CE-SDS (reducing conditions) upon storage at 2-8° C. for 6 months, less than about 1.1% impurity by CE-SDS (reducing conditions) upon storage at 25° C./60% RH for 6 months, and/or less than about 1.9% impurity by CE-SDS (reducing conditions) upon storage at 30° C./75% RH for 6 months. In some embodiments, a liquid composition of the disclosure maintains less than about 0.91% impurity by CE-SDS (non-reducing conditions) upon storage at 2-8° C. for 24 months.

In some embodiments, a liquid composition of the disclosure maintains at least about 88% relative biological activity by inhibition of IL-6 release from C-20/A4 chondrocytes upon storage at 2-8° C. for 24 months, at least about 94% relative biological activity by inhibition of IL-6 release from chondrocytes upon storage at 25° C./60% RH for 6 months, and/or at least about 85% relative biological activity by inhibition of IL-6 release from chondrocytes upon storage at 30° C./75% RH for 6 months.

Antibody Concentration

The IL-17 antibody or antigen binding fragments thereof (e.g., secukinumab) used in the disclosed liquid compositions are described supra. A preferred composition includes secukinumab. We have determined that, at least within the range of about 25 mg/ml to about 150 mg/ml, the concentration of antibody did not have a significant effect on composition stability. Therefore, in some embodiments, the antibody in the liquid composition is present at concentration of at least 25 mg/ml (e.g., about 25 mg/ml to about 150 mg/ml). In some embodiments, the concentration of the antibody in the liquid composition is a high concentration of at least about 25 mg/mL, at least about 50 mg/ml, at least about 75 mg/ml, at least about 100 mg/mL, or at least about 150 mg/ml. In some embodiments, the concentration of the antibody in the liquid composition is a high concentration of about 25 mg/mL-about 150 mg//mL. In one embodiment, the concentration of secukinumab in the liquid composition is about 25 mg/ml. In one embodiment, the concentration of secukinumab in the liquid composition is about 150 mg/ml.

Buffers and pH

Suitable buffering agents for use with the disclosed liquid compositions include, but are not limited to, a gluconate buffer, histidine buffer, a citrate buffer, a phosphate [e.g., sodium or potassium] buffer, a succinate [e.g., sodium] buffer, an acetate buffer, a Tris buffer, glycine, arginine and combinations thereof. We have determined that there was no beneficial impact of succinate or acetate buffer on the stability of liquid compositions of secukinumab. Citrate buffer was assessed as beneficial in the compositions with regard to degradation products by SEC, CEX-acidic and aggregation products by RP HPLC. Overall, histidine buffer showed advantages in aggregation and degradation products by SEC, CEX acidic and RP-B. Thus, histidine buffer is a preferred buffer for the disclosed stable liquid compositions of secukinumab.

A histidine buffer (e.g., at a concentration of about 5 mM to about 50 mM, e.g., about 20 mM to about 50 mM, about 5 mM, about 10 mM, about 15 mM, about 20 mM, about 25 mM, about 30 mM, about 35 mM, about 40 mM, about 45 mM, about 50 mM) is particularly useful. In one embodiment, the stable liquid composition comprises about 20 mM to about 50 mM histidine buffer. The pH of the liquid composition may be in the range 4.0-8.0, which a pH in the range about 5.5-about 7.4 being typical, e.g., about 5.2 to about 6.2, about 5.2 to about 5.8, e.g., about 5.2, about 5.3, about 5.4, about 5.5, about 5.6, about 5.7, about 5.8, about 5.9, about 6, about 6.2, about 6.4, about 6.6, about 6.7, about 6.8, about 6.9, about 7.0, about 7.1, about 7.2, about 7.3, about 7.4. We have determined that with increasing the pH from 5.2 to 5.8, a positive trend in stability was observed (SEC-AP, DLS, SEC-DP, ALP-DP, CEX basic, RP-HPLC). Overall testing indicated that the ideal composition pH of the disclosed liquid compositions is 5.8. Thus, in one embodiment, the pH of the stable liquid antibody composition is about 5.8.

Surfactants

Suitable surfactants for use with the disclosed liquid compositions include, but are not limited to, non-ionic surfactants, ionic surfactants, zwitterionic surfactants and combinations thereof. Typical surfactants for use with the invention include, but are not limited to, sorbitan fatty acid esters (e.g., sorbitan monocaprylate, sorbitan monolaurate, sorbitan monopalmitate), sorbitan trioleate, glycerine fatty acid esters (e.g., glycerine monocaprylate, glycerine monomyristate, glycerine monostearate), polyglycerine fatty acid esters (e.g., decaglyceryl monostearate, decaglyceryl distearate, decaglyceryl monolinoleate), polyoxyethylene sorbitan fatty acid esters (e.g., polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate), polyoxyethylene sorbitol fatty acid esters (e.g., polyoxyethylene sorbitol tetrastearate, polyoxyethylene sorbitol tetraoleate), polyoxyethylene glycerine fatty acid esters (e.g., polyoxyethylene glyceryl monostearate), polyethylene glycol fatty acid esters (e.g., polyethylene glycol distearate), polyoxyethylene alkyl ethers (e.g., polyoxyethylene lauryl ether), polyoxyethylene polyoxypropylene alkyl ethers (e.g., polyoxyethylene polyoxypropylene glycol, polyoxyethylene polyoxypropylene propyl ether, polyoxyethylene polyoxypropylene cetyl ether), polyoxyethylene alkylphenyl ethers (e.g., polyoxyethylene nonylphenyl ether), polyoxyethylene hydrogenated castor oils (e.g. polyoxyethylene castor oil, polyoxyethylene hydrogenated castor oil), polyoxyethylene beeswax derivatives (e.g., polyoxyethylene sorbitol beeswax), polyoxyethylene lanolin derivatives (e.g., polyoxyethylene lanolin), and polyoxyethylene fatty acid amides (e.g., polyoxyethylene stearic acid amide); C10-C18 alkyl sulfates (e.g., sodium cetyl sulfate, sodium lauryl sulfate, sodium oleyl sulfate), polyoxyethylene C10-C18 alkyl ether sulfate with an average of 2 to 4 moles of ethylene oxide units added (e.g., sodium polyoxyethylene lauryl sulfate), and C1-C18 alkyl sulfosuccinate ester salts (e.g., sodium lauryl sulfosuccinate ester); and natural surfactants such as lecithin, glycerophospholipid, sphingophospholipids (e.g., sphingomyelin), and sucrose esters of C12-C18 fatty acids. A composition may include one or more of these surfactants. Preferred surfactants are poloxamer (e.g., poloxamer 188) or polyoxyethylene sorbitan fatty acid esters, e.g. polysorbate 20, 40, 60 or 80. Polysorbate 80 (Tween 80) (e.g., at a concentration of about 0.01%-about 0.1% (w/v), e.g., about 0.01% to about 0.04% (w/v), e.g., about 0.01%, about 0.02%, about 0.04%, about 0.06%, about 0.08%, about 0.1%) is particularly useful. In one embodiment, the stable liquid composition comprises about 0.02% (w/v) polysorbate 80. In one embodiment, the stable liquid composition comprises about 0.02% (w/v) polysorbate 20.

We have determined that there is a significant increase in turbidity, as well as an increase in the amount of visible particles, in liquid compositions lacking a surfactant. However, no advantage of Poloxamer 188 was detected compared to Polysorbate 20 and 80, except for an increase in ALP-DP and RP. Polysorbate 20 and 80 showed comparable efficiency in preventing an increase in turbidity, subvisible and visible particles. Thus, polysorbate 20 and 80 are preferred surfactants for use in the disclosed stable liquid compositions.

Stabilizers

Stabilizers assist in preventing oxidation and aggregation of proteins in pharmaceutical compositions, particularly liquid pharmaceutical compositions, which have a shorter shelf life due to tendency of proteins to oxidize and/or aggregate while in aqueous solutions. Various analytical methods may be used to assess the stability of a given composition, e.g., RP-HPLC may be used to assay the level of oxidation products (pre-main peaks) in the liquid compositions disclosed herein, while SEC may be used to assay the level of aggregation in the liquid compositions disclosed herein.

Suitable stabilizers for use in the disclosed liquid compositions include ionic and non-ionic stabilizers (and combinations thereof), e.g., sugars, glycine, sodium chloride, arginine, EDTA, sodium ascorbate, cysteine, sodium bisulfate, sodium citrate, methionine, and benzyl alcohol. In some embodiments, the liquid pharmaceutical composition will contain at least one stabilizer from group 1 (e.g., sugars [e.g., trehalose, mannitol], amino acids [e.g., glycine, arginine], and sodium chloride). In some embodiments, the liquid pharmaceutical composition will contain at least one stabilizer from group 2 (EDTA, sodium ascorbate, cysteine, sodium bisulfate, sodium citrate, methionine, and benzyl alcohol). Group 2 stabilizers tend to have anti-oxidant properties, which may reduce oxidation of residues in the IL-17 antibodies. In preferred embodiments, a liquid pharmaceutical composition will contain two stabilizers-one from group 1 and one from group 2.

For a group 1 stabilizer, non-ionic stabilizers are preferred. Suitable non-ionic stabilizers include monosaccharides, disaccharides and trisaccharides, e.g., trehalose, raffinose, maltose, sorbitol or mannitol. The sugar may be a sugar alcohol or an amino sugar. The concentration of the group 1 stabilizer may be about 175 mM to about 350 mM, e.g., about 200 mM to about 300 mM, e.g., about 250 mM to about 270 mM, e.g., about 180 to about 300 mM, about 200 mM to about 225 mM, about 175 mM, about 180 mM, about 185 mM, about 190 mM, about 195 mM, about 200 mM, about 225 mM, about 250 mM, about 270 mM, 275 mM, about 300 mM. Mannitol at a concentration of about 200 mM to about 300 mM (e.g., about 250 mM to about 270 mM), trehalose at a concentration of about 180 mM to about 300 mM, e.g., about 200 mM to about 225 mM, sodium chloride at a concentration of about 130 mM to about 150 mM, arginine at a concentration of about 160 mM, glycine at a concentration of about 270 mM are particularly useful.

We have determined that glycine as stabilizer (group 1) was slightly advantageous regarding SEC-AP and DLS, but an increase in almost all degradation products was observed. NaCl as stabilizer (group 1) led to an increase in degradation and aggregation products by SEC and CEX basic variants. Trehalose and mannitol acted as comparable beneficial stabilizer, confirmed with almost all analytics, but mannitol showed a slightly inferior effect (SEC-AP, DLS), plus lower aqueous solubility compared to Trehalose. Thus, trehalose is the preferred stabilizer group 1 due to positive effects on degradation products. In one embodiment, the liquid composition comprises about 200 mM to about 225 mM trehalose. In one embodiment, the liquid composition comprises about 200 mM trehalose. In one embodiment, the liquid composition comprises about 225 mM trehalose.

We have determined that there is a significant impact of the group 2 on the stability of liquid compositions of secukinumab. Our experiments showed that the use of no group 2 stabilizer was inferior (SEC-AP, DLS, turbidity, RP-B), compared to the compositions containing a group 2 stabilizer. Tetrasodium EDTA and cysteine showed an increase in aggregation and degradation product in the respective analytical methods. The addition of cysteine as group 2 stabilizer resulted in turbid compositions after freeze-thaw stress and precipitation within 4 weeks at 40° C. storage. However, we determined that methionine is advantageous in all compositions regarding the analytics. Therefore, for a group 2 stabilizer, methionine, which also has anti-oxidant properties, is preferred. The concentration of the group 2 stabilizer (e.g., methionine) may be at least about 2.5 mM, e.g., about 2.5 to about 20 mM, e.g., at least about 2.5 mM, at least about 5 mM, at least about 10 mM or at least about 20 mM (e.g., about 2.5 mM, about 5 mM, about 10 mM or about 20 mM). In preferred embodiments, a liquid pharmaceutical composition will contain and at least one stabilizer from group 1 and methionine. In some embodiments, the disclosed liquid compositions include about 5 mM methionine.

Other Excipients

The liquid antibody compositions of the disclosure may include further excipients, e.g., additional buffers, salts (e.g., sodium chloride, sodium succinate, sodium sulfate, potassium chloride, magnesium chloride, magnesium sulfate, and calcium chloride), additional stabilizing agents, tonicity modifier (e.g., salts and amino acids [e.g., proline, alanine, L-arginine, asparagine, L-aspartic acid, glycine, serine, lysine, and histidine]), glycerol, albumin, alcohols, preservatives, additional surfactants, anti-oxidants, etc. A thorough discussion of such additional pharmaceutical ingredients is available in Gennaro (2000) Remington: The Science and Practice of Pharmacy. 20th edition, ISBN: 0683306472.

Additional Active Agents

The pharmaceutical products and stable liquid compositions of the disclosure may contain, in addition to the IL-17 antibody or antigen binding fragment thereof, e.g., secukinumab, one or more other active agents (e.g., psoriasis agents, psoriatic arthritis agents, ankylosing spondylitis agents, rheumatoid arthritis agents). Such additional factors and/or agents may be included in the pharmaceutical composition to produce a synergistic effect with the IL-17 antibodies or antigen binding fragments thereof or to minimize side effects caused by the IL-17 antibodies or antigen binding fragments thereof, e.g., secukinumab Examples of psoriasis agents that may be co-formulated with the disclosed IL-17 antibodies, such as secukinumab, include cyclosporine, methotrexate, mycophenolate mofetil, mycophenolic acid, sulfasalazine, 6-thioguanine, fumarates (e.g, dimethylfumarate and fumaric acid esters), azathioprine, corticosteroids, leflunomide, tacrolimus, T-cell blockers (such as Amevive® (alefacept) and Raptiva® (efalizumab), tumor necrosis factor-alpha (TNF-alpha) blockers (such as Enbrel® (etanercept), Humira® (adalimumab), Remicade® (infliximab) and Simponi® (golimumab)) and interleukin 12/23 blockers (such as Stelara® (ustekinumab), tasocitinib, and briakinumab.

Additional psoriasis agents that may be co-formulated with the disclosed IL-17 antibodies, such as secukinumab, for the treatment of psoriasis include apremilast, mometasome, voclosporin, ketokonazole, Neuroskin Forte, recombinant human interleukin-10, voclosporin, MK-3222, tofacitinib, VX-765, MED-1545, fluphenazine decanoate, acetomuinophn, bimosiamose cream, doxycycline, vancomycin, AbGn168, Vitamin D3, RO5310074, fludarabine Calcipotriol and hydrocortisone (LEO 80190), Focetria (Monovalent MF59-Adjuvanted vaccine, tgAAC94 gene therapy vector, Capsaicin, Psirelax, ABT-874 (anti IL-12), IDEC-114, MEDI-522, LE29102, BMS 587101, CD 2027, CRx-191, 8-methoxypsoralen or 5-methoxypsoralen, Bicillin L-A, LY2525623, INCB018424, LY2439821, CEP-701, CC-10004, certolizumab (CZP), GW786034 (pazopanib), doxycycline Curcuminoids C3 Complex, NYC 0462, RG3421, hOKT3gamma1 (Ala-Ala), BT061, teplizumab, Chondroitin sulphate, CNTO 1275, monoclonal antibody to IL-12p40 and IL-23 p40 subunits, BMS-582949, MK0873, MEDI-507, M518101, ABT-874, AMG 827, AN2728, AMG 714, AMG 139, PTH (1-34), U0267 Foam, CNTO 1275, QRX-101, CNTO 1959, LEO 22811, Imiquimod, CTLA4Ig, Alga Dunaliella Bardawil, pioglitazone, pimecrolimus, ranibizumab, Zidovudine CDP870 (Certolizumab pegol), Onercept (r-hTBP-1), ACT-128800, 4,4-dimethyl-benziso-2H-selenazine, CRx-191, CRx-197, doxercalciferol, LAS 41004, WBI-1001, tacrolimus, RAD001, rapamycin, rosiglitazone, pioglitazone, ABT-874, Aminopterin, AN2728, CD2027, ACT-128800, mometasone furoate, CT 327, clobetasol+LCD, BTT1023, E6201, topical vitamin B12, IP10. C8, BFH772, LEO 22811, Fluphenazine, MM-093, Clobex, SCH 527123, CF101, SRT2104, BIRT2584, CC10004, Tetrathiomolybdate, CP-690,550, U0267, ASP015K, VB-201, Acitretin (also called U0279), RWJ-445380, Clobetasol propionate, botulinum toxin type A, alefacept, erlotinib, BCT194, Roflumilast, CNTO 1275, halobetasol, ILV-094, CTA018 cream, COL-121, MEDI-507, AEB071.

Additional psoriasis agents that may be co-formulated with the disclosed IL-17 antibodies, such as secukinumab, include IL-6 antagonists, CD20 antagonistis, CTLA4 antagononists, IL-17 antagonists, IL-8 antagnoists, IL-21 antagonistis, IL-22 antagonist, VGEF antagnosits, CXCL antagonists, MMP antagonists, defensin antagonists, IL-1beta antagonists, and IL-23 antagonists (e.g., receptor decoys, antagonistic antibodies, etc.). Preferred psoriasis agents that may be co-formulated with secukinumab are DMARDs (e.g, MTX and cyclosporine), IL-12/-23 antagonists (e.g., ustekinumab), CTLA-4 antagonists (e.g., CTLA4-Ig), and TNF-alpha antagonists.

Broadly speaking, rheumatoid arthritis agents, psoriatic arthritis agents, and ankylosing spondylitis agents that may be co-formulated with the disclosed IL-17 antibodies, such as secukinumab, may be, inter alia, an immunosuppressive agent, a DMARD, a pain-control drug, a steroid, a non-steroidal anti-inflammatory drug (NSAID), a cytokine antagonist, a bone anabolic, a bone anti-resorptive, and combinations thereof. Representative agents include cyclosporin, retinoids, corticosteroids, propionic acid derivative, acetic acid derivative, enolic acid derivatives, fenamic acid derivatives, Cox-2 inhibitors, lumiracoxib, ibuprophen, cholin magnesium salicylate, fenoprofen, salsalate, difunisal, tolmetin, ketoprofen, flurbiprofen, oxaprozin, indomethacin, sulindac, etodolac, ketorolac, nabumetone, naproxen, valdecoxib, etoricoxib, MK0966; rofecoxib, acetominophen, Celecoxib, Diclofenac, tramadol, piroxicam, meloxicam, tenoxicam, droxicam, lornoxicam, isoxicam, mefanamic acid, meclofenamic acid, flufenamic acid, tolfenamic, valdecoxib, parecoxib, etodolac, indomethacin, aspirin, ibuprophen, firocoxib, methotrexate (MTX), antimalarial drugs (e.g., hydroxychloroquine and chloroquine), sulfasalazine, Leflunomide, azathioprine, cyclosporin, gold salts, minocycline, cyclophosphamide, D-penicillamine, minocycline, auranofin, tacrolimus, myocrisin, chlorambucil, TNF alpha antagonists (e.g., TNF alpha antagonists or TNF alpha receptor antagonists), e.g., ADALIMUMAB (Humira®), ETANERCEPT (Enbrel®), INFLIXIMAB (Remicade®; TA-650), CERTOLIZUMAB PEGOL (Cimzia®; CDP870), GOLIMUMAB (Simponi®; CNTO148), ANAKINRA (Kineret®), RITUXIMAB (Rituxan®; MabThera®), ABATACEPT (Orencia®), TOCILIZUMAB (RoActemra/Actemra®), integrin antagonists (TYSABRI® (natalizumab)), IL-1 antagonists (ACZ885 (Ilaris)), Anakinra (Kineret®)), CD4 antagonists, IL-23 antagonists, IL-20 antagonists, IL-6 antagonists, BLyS antagonists (e.g, Atacicept, Benlysta®/LymphoStat-B® (belimumab)), p38 Inhibitors, CD20 antagonists (Ocrelizumab, Ofatumumab (Arzerra®)), interferon gamma antagonists (Fontolizumab), prednisolone, Prednisone, dexamethasone, cortisol, cortisone, hydrocortisone, methylprednisolone, betamethasone, triamcinolone, beclometasome, fludrocottisone, deoxycorticosterone, aldosterone, SB-681323, Rob 803, AZD5672, AD 452, SMP 114, HZT-501, CP-195,543, Doxycycline, vancomycin, CRx-102, AMG108, pioglitazone, SBI-087, SCIO-469, Cura-100, Oncoxin+Viusid, TwHF, PF-04171327, AZDS672, Methoxsalen, ARRY-438162, Vitamin D-ergocalciferol, Milnacipran, Paclitaxel, GW406381, rosiglitazone, SC12267 (4SC-101); LY2439821, BTT-1023, ERB-041, ERB-041, KB003, CF101, ADL5859, MP-435, ILV-094, GSK 706769, GW856553, ASK8007, MOR103, HE3286, CP-690,550 (tasocitinib), REGN88 (SAR153191), TRU-015, BMS-582949, SBI-087, LY2127399, E-551S-551, H-551, GSK3152314A, RWJ-445380, Tacrolimus (Prograf®), RAD001, rapamune, rapamycin, fostamatinib, Fentanyl, XOMA 052, CNTO 136, JNJ 38518168, Imatinib, ATN-103, ISIS 104838, folic acid, folate, TNFa kinoid, MM-093, type II collagen, VX-509, AMG 827 70, masitinib (AB1010), LY2127399, cyclosporine, SB-681323, MK0663, NNC 0151-0000-0000, ATN-103, CCX 354-C, CAM3001, LX3305, Cetrorelix, MDX-1342, TMI-005, MK0873, CDP870, Tranilast, CF101, mycophenolic acid (and esters thereof), VX-702, GLPG0259, SB-681323, BG9924, ART621, LX3305, T-614, Fostamatinib disodium (R935788), CCI-779, ARRY-371797, CDP6038, AMG719, BMS-582949, GW856553, rosiglitazone, CH-4051, CE-224,535, GSK1827771, GW274150, BG9924, PLX3397, TAK-783, INCB028050, LY2127399, LY3009104, R788, Curcumin (Longvida™), Rosuvastatin, PRO283698, AMG 714, MTRX1011A, Maraviroc, MEDI-522, MK0663, STA 5326 mesylate, CE-224,535, AMG108, BG00012 (BG-12; Biogen), ramipril, VX-702, CRx-102, LY2189102, SBI-087, SB-681323, CDP870, Milnacipran, PD 0360324, PH-797804, AK106-001616, PG-760564, PLA-695, MK0812, ALD518, Cobiprostone, somatropin, tgAAC94 gene therapy vector, MK0359, GW856553, esomeprazole, everolimus, trastuzumab, bone anabolics and bone anti-resorptives (e.g., PTH, bisphosphonates (e.g., zoledronic acid), JAK1 and JAK2 inhibitors, pan JAK inhibitors, e.g., tetracyclic pyridone 6 (P6), 325, PF-956980, sclerostin antagonists (e.g., disclosed in WO09047356, WO2000/32773, WO2006102070, US20080227138, US20100028335, US20030229041, WO2005003158, WO2009039175 WO2009079471, WO03106657, WO2006119062, WO08115732, WO2005/014650, WO2005/003158, WO2006/119107, WO2008/061013, WO2008/133722, WO2008/115732, U.S. Pat. Nos. 7,592, 429, 7,879,322, 7,744,874, the contents of which are incorporated by reference herein in their entirety [preferred anti-sclerostin antibodies and antigen-binding portions thereof for use in the disclosed methods, pharmaceutical compositions, kits and uses are found in WO09047356 (equivalent to U.S. Pat. No. 7,879,322), WO06119107 (equivalent to U.S. Pat. Nos. 7,872,106 and 7,592,429) and WO08115732 (equivalent to U.S. Pat. No. 7,744,874]), denosumab, IL-6 antagonists, CD20 antagonistis, CTLA4 antagonists, IL-8 antagonists, IL-21 antagonists, IL-22 antagonist, integrin antagonists (Tysarbri® (natalizumab)), VGEF antagnosits, CXCL antagonists, MMP antagonists, defensin antagonists, IL-1 antagonists (including IL-1 beta antagonsits), and IL-23 antagonists (e.g., receptor decoys, antagonistic antibodies, etc.). Preferred rheumatoid arthritis agents that may be co-formulated with the disclosed IL-17 antibodies, such as secukinumab, are DMARDs, such as methotrexate, and TNF alpha antagonists. Preferred ankylosing spondylitis agents that may be co-formulated with the disclosed IL-17 antibodies, such as secukinumab, are NSAIDs, DMARDS, such as sulfasalazine, and TNF alpha antagonists. Preferred psoriatic arthritis agents that may be co-formulated with the disclosed IL-17 antibodies, such as secukinumab, are DMARDS, such as cyclosporine, CTLA-4 blockers (e.g, CLTA4-Ig), alefacept, and TNF alpha antagonists.

A skilled artisan will be able to discern the appropriate dosages of the above agents for co-composition with the disclosed IL-17 antibodies, such as secukinumab.

Disclosed herein are stable liquid pharmaceutical compositions comprising about 20 mg/ml to about 175 mg/ml (e.g., about 25 mg/ml to about 150 mg/ml) of an IL-17 antibody or antigen binding fragment thereof as disclosed herein (e.g., secukinumab), about 10 mM to about 30 mM buffer (e.g., Histidine) pH 5.2-about 6.0, about 200 mM to about 225 mM stabilizer (e.g., trehalose), about 0.02% surfactant (e.g., polysorbate 80), and about 2.5 mM to about 20 mM methionine.

In some embodiments, the concentration of methionine in the liquid pharmaceutical composition of the disclosed pharmaceutical is about 2.5 mM, about 5 mM, about 10 mM or about 20 mM, preferably about 5 mM. In some embodiments, the pH of the liquid pharmaceutical composition is about 5.8. In some embodiments, the concentration of secukinumab of the disclosed composition is about 25 mg/ml or about 150 mg/ml. In some embodiments, the liquid pharmaceutical composition comprises a buffer selected from the group consisting of a histidine buffer, a citrate buffer, an acetate buffer, and a succinate buffer. In some embodiments, the liquid pharmaceutical composition employs a histidine buffer at a concentration of about 20 mM. In some embodiments, the liquid pharmaceutical composition comprises a surfactant selected from a polysorbate and a poloxamer. In some embodiments, the liquid pharmaceutical composition further comprises a surfactant selected from polysorbate 80, polysorbate 20, and poloxamer 188. In some embodiments, the liquid pharmaceutical composition comprises polysorbate 80 at a concentration of about 0.01% (w/v) to about 0.04% (w/v), preferably at about 0.02% (w/v). In some embodiments, the liquid pharmaceutical composition comprises polysorbate 20 at a concentration of about 0.02% (w/v). In some embodiments, the liquid pharmaceutical composition comprises a stabilizer selected from the group consisting of mannitol, sodium chloride, trehalose, arginine HCL, and glycine. In some embodiments, the liquid pharmaceutical composition comprises trehalose at a concentration of about 180 mM to about 300 mM, preferably at about 200 mM or about 225 mM.

Disclosed herein are pharmaceutical products comprising: a container having a headspace, wherein the oxygen content in the headspace is less than about 12%, and a liquid pharmaceutical composition having a pH of about 5.2 to about 6.2 disposed within said container, said composition comprising: about 20 mg/ml to about 175 mg/ml (e.g., about 25 mg/ml to about 150 mg/ml) an IL-17 antibody or antigen binding fragment thereof as disclosed herein (e.g., secukinumab); and about 2.5 to about 20 mM L-methionine, wherein the liquid pharmaceutical composition is not reconstituted from a lyophilisate.

In some embodiments, the concentration of methionine in the liquid pharmaceutical composition of the disclosed pharmaceutical is about 2.5 mM, about 5 mM, about 10 mM or about 20 mM, preferably about 5 mM. In some embodiments, the oxygen content in the headspace of the disclosed pharmaceutical product is less than about 10%, e.g., less than about 8%, preferably less than about 6%. In some embodiments, the liquid pharmaceutical composition of the disclosed pharmaceutical product has a pH of about 5.8. In some embodiments, the concentration of secukinumab of the disclosed pharmaceutical product is about 25 mg/ml or about 150 mg/ml. In some embodiments, the liquid pharmaceutical composition of the disclosed pharmaceutical product further comprises a buffer selected from the group consisting of a histidine buffer, a citrate buffer, an acetate buffer, and a succinate buffer. In some embodiments, the liquid pharmaceutical composition of the disclosed pharmaceutical product employs a buffer at a concentration of about 10 mM to about 30 mM. In some embodiments, the liquid pharmaceutical composition of the disclosed pharmaceutical product employs a histidine buffer at a concentration of about 20 mM. In some embodiments, the liquid pharmaceutical composition of the disclosed pharmaceutical product further comprises a surfactant selected from a polysorbate and a poloxamer. In some embodiments, the liquid pharmaceutical composition of the disclosed pharmaceutical product further comprises a surfactant selected from polysorbate 80, polysorbate 20, and poloxamer 188. In some embodiments, the liquid pharmaceutical composition of the disclosed pharmaceutical product further comprises polysorbate 80 at a concentration of about 0.01% (w/v) to about 0.04% (w/v), preferably at about 0.02% (w/v). In some embodiments, the liquid pharmaceutical composition of the disclosed pharmaceutical product further comprises polysorbate 20 at a concentration of about 0.02% (w/v). In some embodiments, the liquid pharmaceutical composition of the disclosed pharmaceutical product further comprises a stabilizer selected from the group consisting of mannitol, sodium chloride, trehalose, arginine HCL, and glycine. In some embodiments, the liquid pharmaceutical composition of the disclosed pharmaceutical product further comprises trehalose at a concentration of about 180 mM to about 300 mM, preferably at about 200 mM or about 225 mM. In some embodiments, the container of the disclosed pharmaceutical product is a cartridge, syringe, pen or vial.

Disclosed herein are pharmaceutical products comprising: a container having a headspace, wherein the oxygen content in the headspace is less than about 6%; and a liquid pharmaceutical composition disposed within said container, said composition comprising about 20 mg/ml to about 175 mg/ml (e.g., about 25 mg/ml to about 150 mg/ml) an IL-17 antibody or antigen binding fragment thereof as disclosed herein (e.g., secukinumab), about 10 mM to about 30 mM histidine pH 5.8, about 200 mM to about 225 mM trehalose, about 0.02% polysorbate 80, and about 2.5 mM to about 20 mM methionine, wherein the liquid pharmaceutical composition is not reconstituted from a lyophilisate.

In some embodiments, the pharmaceutical product comprises about 25 mg/ml secukinumab and about 225 mM trehalose. In some embodiments, the pharmaceutical product comprises about 150 mg/ml secukinumab and about 200 mM trehalose. In some embodiments, the container of the disclosed pharmaceutical product is a cartridge, syringe, pen or vial.

In some embodiments, the pharmaceutical product has a sufficient amount of the IL-17 antagonist to allow delivery of at least about 75 mg-about 300 mg IL-17 antagonist (e.g., IL-17 antibody, e.g., secukinumab) per unit dose. In some embodiments, the pharmaceutical product has a sufficient amount of the IL-17 antagonist (e.g., IL-17 antibody, e.g., secukinumab) to allow delivery of at least about 10 mg/kg per unit dose. In some embodiments, the pharmaceutical product is formulated at a dosage to allow intravenous delivery of about 10 mg/kg IL-17 antagonist (e.g., IL-17 antibody, e.g., secukinumab) per unit dose. In some embodiments, the pharmaceutical product is formulated at a dosage to allow subcutaneous delivery of about 75 mg-about 300 mg IL-17 antagonist (e.g., IL-17 antibody, e.g., secukinumab) per unit dose.

Processes of Making Liquid Compositions and Pharmaceutical Products

Also described herein are processes of making the pharmaceutical products and liquid compositions of the disclosure. These processes help reduce oxidation of the disclosed IL-17 antibodies. In brief, a liquid composition is prepared by combining the desired excipients (e.g., group 1 stabilizer (e.g., trehalose), group 2 stabilizer (methionine), surfactant (e.g., PS80), buffer (e.g., histidine)) with an IL-17 antibody or antigen binding fragment thereof (e.g, secukinumab) to the desired concentrations (e.g., about 25 to about 150 mg/ml secukinumab, about 20 mM histidine pH 5.8, about 200 mM to about 225 mM trehalose, about 0.02% polysorbate 80, and about 2.5 mM to about 20 mM methionine) and pH (e.g., about pH 5.8). This liquid composition is then disposed in the container of choice (e.g., vial, syringe, cartridge [e.g., for use with an autoinjector]). The oxygen content in the headspace is adjusted to the desired level (e.g., less than about 12%, less than 10%, less than about 8%, less than about 6%, etc.), which may occur prior to filling of the container with the liquid composition, during filling of the container with the liquid composition, or during stoppering/sealing of the container.

Disclosed herein are processes for reducing the oxidation of secukinumab, comprising: preparing a liquid composition having a pH of about 5.2 to about 6.2 and comprising: about 20 mg/ml to about 175 mg/ml (e.g., about 25 mg/ml to about 150 mg/ml) an IL-17 antibody or antigen binding fragment thereof as disclosed herein (e.g., secukinumab); and about 2.5 mM to about 20 mM methionine; disposing said liquid composition in a container having a headspace; and adjusting the oxygen content in the headspace to less than or equal to about 12%.

In some embodiments of the disclosed processes, adjusting step c) is performed by purging the headspace using an inert gas. In some embodiments of the disclosed processes, the inert gas is nitrogen or argon. In some embodiments of the disclosed processes, the concentration of methionine in the liquid composition is about 2.5 mM, about 5 mM, about 10 mM or about 20 mM, preferably about 5 mM. In some embodiments of the disclosed processes, the oxygen content in the headspace is adjusted to less than about 10%, e.g., less than about 8%, preferably less than about 6%. In some embodiments of the disclosed processes, the liquid composition has a pH of about 5.8. In some embodiments of the disclosed processes, the concentration of secukinumab in the liquid composition is about 25 mg/ml or about 150 mg/ml. In some embodiments of the disclosed processes, the container is a cartridge, syringe, pen or vial.

Methods of Using Pharmaceutical Products and Liquid Compositions

The disclosed pharmaceutical products and liquid compositions will be used for the treatment of patients, e.g., having autoimmune diseases (e.g., psoriasis, rheumatoid arthritis, ankylosing spondylitis, psoriatic arthritis, etc.). The appropriate dosage will, of course, vary depending upon, for example, the particular IL-17 antibodies or antigen binding fragments thereof, e.g., secukinumab, to be employed, the host, the mode of administration and the nature and severity of the condition being treated, and on the nature of prior treatments that the patient has undergone. Ultimately, the attending health care provider will decide the amount of the IL-17 antibody with which to treat each individual patient. In some embodiments, the attending health care provider may administer low doses of the IL-17 antibody and observe the patient's response. In other embodiments, the initial dose(s) of IL-17 antibody administered to a patient are high, and then are titrated downward until signs of relapse occur. Larger doses of the IL-17 antibody may be administered until the optimal therapeutic effect is obtained for the patient, and the dosage is not generally increased further.

The timing of dosing is generally measured from the day of the first dose of the active compound (e.g., secukinumab), which is also known as "baseline". However, different health care providers use different naming conventions, as shown in Table 2, below.

TABLE 2

Common naming conventions for dosing regimens. Bolded items refer to the naming convention used herein.

| Week | 0/1 | 1/2 | 2/3 | 3/4 | 4/5 | 5/6 | 6/7 | 7/8 | 8/9 | Etc. |
|---|---|---|---|---|---|---|---|---|---|---|
| 1st day | 0/1 | 7/8 | 14/15 | 21/22 | 28/29 | 35/36 | 42/43 | 49/50 | 56/57 | Etc. |

Notably, week zero may be referred to as week 1 by some health care providers, while day zero may be referred to as day one by some health care providers. Thus, it is possible that different physicians will designate, e.g., a dose as being given during week 3/on day 21, during week 3/on day 22, during week 4/on day 21, during week 4/on day 22, while referring to the same dosing schedule. For consistency, the first week of dosing will be referred to herein as week 0, while the first day of dosing will be referred to as day 1. However, it will be understood by a skilled artisan that this naming convention is simply used for consistency and should not be construed as limiting, i.e., weekly dosing is the provision of a weekly dose of the IL-17 antibodies or antigen binding fragments thereof, e.g., secukinumab, regardless of whether the physician refers to a particular week as "week 1" or "week 2". As an example of naming using the convention designated herein, five doses of secukinumab administered weekly may be provided during week 0 (e.g., on about day 1), during week 1 (e.g., on about day 8), during week 2 (e.g., on about day 15), during week 3 (e.g., on about day 22), and during week 4 (e.g., on about day 29). It will be understood that a dose need not be provided at an exact time point, e.g., a dose due approximately on day 29 could be provided, e.g., on day 24 to day 34, e.g., day 30, as long as it is provided in the appropriate week.

In some embodiments, the disclosed methods and uses employ an initial (sometimes called "induction") regimen that lasts 1, 2, 3, 4, 5, 6, 7, 8, 9, 10, 11, 12, 13, 14, 15, or 16 weeks. In some embodiments, the initial regimen uses dosing during weeks 0, 1, 2, and 3. In other embodiments, the initial regimen uses dosing during weeks 0, 1, 2, 3, 4, 8 and 12. In some embodiments, the initial regimen comprises administering several (e.g., 1, 2, 3, 4, 5, 6, 7, preferably 4 or 5) doses of about 150 mg-300 mg, e.g., about four or five doses of 150 mg or 300 mg (preferably five doses of about 150 mg-about 300 mg) of the IL-7 antibody, e.g., secukinumab. In further embodiments, initial doses are delivered weekly, bi-weekly, every other week, or monthly [every 4 weeks], preferably weekly. In some embodiments, 150 mg or 300 mg of the IL-17 antibody, e.g., secukinumab is administered by subcutaneous injection, with initial dosing at weeks 0, 1, 2 and 3.

For a maintenance regimen, a dose may be provided every month (also called "monthly" dosing) (i.e., every 4 weeks, i.e., about every 28 days), every two months (i.e., every 8 weeks, i.e., about every 56 days), or every three months (i.e., every 12 weeks, i.e., about every 84 days). In some embodiments, the maintenance regimen begins following week 12. In some embodiments, the maintenance regimen begins following week 3. A first dose of a maintenance regimen will be administered on a date usually measured from the final dose of the induction regimen. Thus, as an example, if the final dose of the induction regimen is provided during week 12, then the first dose as part of a monthly [every 4 weeks] maintenance regimen will be delivered during week 16, the first dose as part of an every two month maintenance regimen will be delivered during week 20, the first dose as part of an every three month maintenance regimen will be delivered during week 24, etc. In some embodiments, the maintenance regimen comprises administering a dose of the IL-17 antibody or antigen binding fragment thereof, e.g., secukinumab, weekly, every two weeks, monthly [every 4 weeks], every other month, quarterly, bi yearly, or yearly. In some embodiments, the maintenance regimen employs monthly dosing (every 4 weeks). In some embodiments, the first dose of the maintenance regimen is delivered during week 4 or during 16. In some embodiments, the maintenance regimen comprises administering a dose of about 150 mg-300 mg, e.g., about 150 mg or about 300 mg of the IL-17 antibody or antigen binding fragment thereof, e.g., secukinumab.

Delivery of an IL-17 antibody, such as secukinumab, during a loading regimen, induction regimen and/or maintenance regimen may be via a subcutaneous route, e.g., delivery of dosages of about 75 mg-about 300 mg (e.g., about 50 mg, about 75 mg, about 100 mg, about 125 mg, about 150 mg, about 175 mg, about 200 mg, about 225 mg, about 250 mag, about 275 mg, about 300 mg, about 325 mg), via an intravenous route, e.g., delivery of dosages of about 1 mg/kg,-about 50 mg/kg (e.g., about 1 mg/kg, about 3 mg/kg, about 10 mg/kg, about 30 mg/kg, about 40 mg/kg, about 50 mg/kg, etc.) or any other route of administration (e.g, intramuscular, i.m.). In preferred embodiments, the dose of the IL-17 antibody is delivered s.c.

In preferred embodiments the patient is administered a dose of about 150 mg-about 300 mg (e.g., about 150 mg or about 300 mg) of the IL-17 antibody or antigen binding fragment thereof, e.g., secukinumab, by subcutaneous injection, with initial dosing at weeks 0, 1, 2 and 3, followed by monthly maintenance dosing, starting at week 4. In this regimen, dosing occurs during each of weeks 0, 1, 2, 3, 4, 8, 12, 16, 20, etc. A 300 mg dose may be given as two subcutaneous injections of 150 mg.

Disclosed herein are methods of treating an autoimmune disease (e.g., psoriasis, rheumatoid arthritis, ankylosing spondylitis, psoriatic arthritis), comprising administering to a patient in need thereof a dose of about 150 mg-about 300 mg (e.g., about 150 mg or about 300 mg) of an IL-17 antibody or antigen binding fragment thereof, e.g., secukinumab, by subcutaneous injection, with initial dosing at weeks 0, 1, 2 and 3, followed by monthly maintenance dosing, starting at week 4, wherein the IL-17 antibody or antigen binding fragment thereof, e.g., secukinumab, is provided as part of a pharmaceutical composition comprising: about 20 mg/ml to about 175 mg/ml (e.g., about 25 mg/ml to about 150 mg/ml) an IL-17 antibody or antigen binding fragment thereof as disclosed herein (e.g., secukinumab); a buffer having a pH of about 5.2 to about 6.2; and about 2.5 to 20 mM methionine, wherein the liquid pharmaceutical composition is not reconstituted from a lyophilisate.

Disclosed herein is the use of an IL-17 antibody (e.g., secukinumab) for the manufacture of a medicament for the treatment of an autoimmune disease (e.g., psoriasis, rheumatoid arthritis, ankylosing spondylitis, psoriatic arthritis) in a patient, wherein the medicament is formulated to comprise containers, each container having headspace with an oxygen content of less than about 12% (e.g., less than about 10%, less than about 8%, less than about 7%, less than about 6%, etc.) and a liquid pharmaceutical composition disposed within said container, said composition comprising: about 20 mg/ml to about 175 mg/ml (e.g., about 25 mg/ml to about 150 mg/ml) an IL-17 antibody or antigen binding fragment thereof as disclosed herein (e.g., secukinumab); a buffer having a pH of about 5.2 to about 6.2; and about 2.5 to 20 mM methionine, wherein the liquid pharmaceutical composition is not reconstituted from a lyophilisate Kits Comprising Pharmaceutical Products and Liquid Compositions The disclosure also encompasses kits for treating various autoimmune diseases (e.g., psoriasis). Such kits broadly include at least one of the disclosed pharmaceutical products or liquid compositions and instructions for use. The instructions will disclose appropriate techniques for the provision of the stable liquid composition to the patient as part of a dosing regimen. These kits may also contain additional agents (described supra) for treating autoimmune diseases, e.g., psoriasis, for delivery in combination with (i.e., simultaneously or sequentially [before or after]) the enclosed liquid composition.

Disclosed herein are kits for the treatment of a patient having an autoimmune disease (e.g., psoriasis), comprising: a) a container having a headspace, wherein the oxygen content in the headspace is less than about 12% (e.g., less than about 10%, less than about 8%, less than about 7%, less than about 6%, etc.), b) a liquid pharmaceutical composition disposed within said container, said composition comprising: i) about 20 mg/ml to about 175 mg/ml (e.g., about 25 mg/ml to about 150 mg/ml) an IL-17 antibody or antigen binding fragment thereof as disclosed herein (e.g., secukinumab); ii) a buffer having a pH of about 5.2 to about 6.2; and iii) about 2.5 to 20 mM methionine, wherein the liquid pharmaceutical composition is not reconstituted from a lyophilisate; and c) instructions for administering the liquid pharmaceutical composition to the patient. In some embodiments, the container is a pen, pre-filled syringe, autoinjector or vial.

General

In some embodiments of the disclosure, the IL-17 antibody or antigen binding fragment thereof is selected from the group consisting of: a) an IL-17 antibody that binds to an epitope of IL-17 comprising Leu74, Tyr85, His86, Met87, Asn88, Val124, Thr125, Pro126, Ile127, Val128, His129; b) an IL-17 antibody that binds to an epitope of IL-17 comprising Tyr43, Tyr44, Arg46, Ala79, Asp80; c) an IL-17 antibody that binds to an epitope of an IL-17 homodimer having two mature IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain; d) an IL-17 antibody that binds to an epitope of an IL-17 homodimer having two mature IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain, wherein the IL-17 binding molecule has a $K_D$ of about 100-about 200 pM (e.g., as measured by Biacore®), and wherein the IL-17 binding molecule has an in vivo half-life of about 23-about 30 days; and e) an IL-17 antibody that comprises an antibody selected from the group consisting of: i) an immunoglobulin heavy chain variable domain ($V_H$) comprising the amino acid sequence set forth as SEQ ID NO:8; ii) an immunoglobulin light chain variable domain ($V_L$) comprising the amino acid sequence set forth as SEQ ID NO:10; iii) an immunoglobulin $V_H$ domain comprising the amino acid sequence set forth as SEQ ID NO:8 and an immunoglobulin $V_L$ domain comprising the amino acid sequence set forth as SEQ ID NO: 10; iv) an immunoglobulin $V_H$ domain comprising, in sequence, the hypervariable regions set forth as SEQ ID NO:1, SEQ ID NO:2, and SEQ ID NO:3; v) an immunoglobulin $V_L$ domain comprising, in sequence, the hypervariable regions set forth as SEQ ID NO:4, SEQ ID NO:5 and SEQ ID NO:6; vi) an immunoglobulin $V_H$ domain comprising, in sequence, the hypervariable regions set forth as SEQ ID NO:11, SEQ ID NO: 12 and SEQ ID NO: 13; vii) an immunoglobulin $V_H$ domain comprising, in sequence, the hypervariable regions set forth as SEQ ID NO: 1, SEQ ID NO:2, and SEQ ID NO:3 and an immunoglobulin $V_L$ domain comprising, in sequence, the hypervariable regions set forth as SEQ ID NO:4, SEQ ID NO:5 and SEQ ID NO:6; and viii) an immunoglobulin $V_H$ domain comprising, in sequence, the hypervariable regions set forth as SEQ ID NO:11, SEQ ID NO:12 and SEQ ID NO:13 and an immunoglobulin $V_L$ domain comprising, in sequence, the hypervariable regions set forth as SEQ ID NO:4, SEQ ID NO:5 and SEQ ID NO:6; ix) an immunoglobulin heavy chain comprising the amino acid sequence set forth as SEQ ID NO:15 (with or without the C-terminal lysine); x) an immunoglobulin light chain comprising the amino acid sequence set forth as SEQ ID NO:14; xi) an immunoglobulin heavy chain comprising the amino acid sequence set forth as SEQ ID NO: 15 (with or without the C-terminal lysine) and an immunoglobulin light chain comprising the amino acid sequence set forth as SEQ ID NO: 14. In some embodiments of the disclosure, the IL-17 antibody or antigen binding fragment thereof is a human antibody, preferably secukinumab.

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference. The following Examples are presented in order to more fully illustrate the preferred embodiments of the disclosure. These examples should in no way be construed as limiting the scope of the disclosed patient matter, as defined by the appended claims.

EXAMPLES

It is understood that the examples and embodiments described herein are for illustrative purposes only and that various modifications and changes in light thereof will be suggested to persons skilled in the art and are to be included within the spirit and purview of this application and scope of the amended claims.

These examples describe the development of stable liquid compositions of secukinumab. The data shows that the composition pH and the choice of group 2 stabilizer had a large effect on the stability of the liquid composition. The data also shows an impact of headspace oxygen content as influencing the stability of the liquid composition. The antibody concentration, choice of surfactant, choice of group 1 stabilizer and choice of buffer system had a smaller influence on stability. Therefore, when considering the variables having greater influence on stability, the disclosed pharmaceutical products comprise a container (e.g., PFS or vial) having a headspace, wherein the oxygen content in the headspace is less than about 12%, and a liquid pharmaceutical composition disposed within said container, said composition having a pH of about 5.2 to about 6.2 and comprising secukinumab in a concentration of about 20 mg/mL to 175 mg/mL and about 2.5 to about 20 mM L-methionine. When considering the variables having both large and small impacts on stability, the disclosed pharmaceutical products comprise a container (e.g., PFS or vial) having a headspace, wherein the oxygen content in the headspace is less than about 12%, and a liquid pharmaceutical composition disposed within said container, said composition having a pH of about 5.2 to about 6.2 and comprising secukinumab; a buffer; a surfactant, a stabilizer, and about 2.5 to about 20 mM L-methionine.

Based on the data disclosed below, preferred liquid compositions comprise about 25 mg/mL-about 165 mg/mL secukinumab, about 185 mM-about 225 mM trehalose, about 0.01%-about 0.03% polysorbate 80, about 2.5 mM- about 20 mM L-methionine and about 10-30 mM histidine buffer (e.g., about 20 mM histidine buffer) at pH about 5.8.

A preferred liquid composition I comprises about 150 mg/mL secukinumab, about 200 mM trehalose, about 0.02% polysorbate 80, about 5 mM L-methionine, and about 20 mM histidine buffer at pH about 5.8. A preferred pharmaceutical product I comprises the aforementioned liquid composition 1 disposed in a pre-filled syringe (PFS).

Another preferred liquid composition II comprises about 25 mg/mL secukinumab, about 225 mM trehalose, about 0.02% polysorbate 80, about 5 mM L-methionine, and about 20 mM histidine buffer at pH about 5.8. A preferred pharmaceutical product II comprises the aforementioned liquid composition II disposed in a vial.

TABLE 3

Abbreviations used in Examples

| Abbreviation | Definition |
| --- | --- |
| CE-SDS | Capillary Electrophoresis (Sodium Dodecyl Sulfate) |
| CEX | Cation Exchange Chromatography |
| Cys-CEX | Cystamine Cation Exchange Chromatography |
| DLS | Dynamic Light Scattering |
| DoE | Design of Experiment |
| HPLC | High Performance Liquid Chromatography |
| LLS | Laser Light Scattering |
| RH | Relative humidity |
| RP-HPLC | Reverse phase-High Performance Liquid Chromatography |
| SDS-PAGE | Sodium Dodecyl Sulfate-Polyacrylamid Gel Electrophoresis |
| SEC | Size Exclusion Chromatography |
| AP-SEC | Aggregation Products by SEC |
| DP-SEC | Degradation Products by SEC |

TABLE 4

Analytics used in Examples.

Analytical Assay
UV: Assay of protein by UV absorption
SEC: Purity by SEC, AP-SEC, DP-SEC
SDS-PAGE: purity by SDS-PAGE (non-reducing), purity by SDS-PAGE (reducing), impurities by SDS-PAGE (reducing)
CE-SDS: Purity by CE-SDS (non-reducing), Impurities by CE-SDS (non-reducing)
LLS: average molecular weight by LLS
DLS: polydispersity by DLS, hydrodynamic radius by DLS
Turbidity
Sub-visible particles by light obscuration
Visible particles
RP-HPLC: purity by RP-HPLC, and pre-main peak species by RP-HPLC
CEX: purity by CEX, acidic variants by CEX, basic variants by CEX
Color
activity by Cys-CEX
Free SH-groups (Ellmans test)
biological activity Part I—Detailed Analysis of Variables with Greater Influence on Secukinumab Liquid State Stability (Headspace Oxygen, pH and L-methionine)

Example 1: L-Methionine

The effect of several anti-oxidative stabilizers on secukinumab stability was characterized using a broad set of analytical techniques.

In early studies, a range of anti-oxidative stabilizers, comprising tetra sodium EDTA sodium ascorbate, cysteine, sodium bisulfite and sodium citrate were evaluated. Although none of these adequately stabilized the molecule, a small stabilizing effect on aggregation products by SEC of tetra sodium EDTA and sodium citrate as compared to the compositions containing no anti-oxidative stabilizers has been seen (data not shown).

In further studies, the stabilizers cysteine, tetra sodium EDTA and L-methionine were evaluated at a concentration of 10 mM and compared to no stabilizer using secukinumab concentration of 150 mg/mL with a DoE approach. The compositions were filled in PFS and placed on a 2 months stability study at long-term (5° C.), accelerated (25° C.) and stressed (40° C.) conditions and were evaluated with regards to physical stability (AP-SEC, DLS, turbidity, visible and sub-visible particles by light obscuration), chemical stability (purity by CEX, purity by RP-HPLC, color) and indicators of biological activity (activity by Cys-CEX, free SH-groups). In addition, freeze-thaw (5 cycles of −20° C. to room temperature) and shaking stress (150 rpm for one week) was applied to compositions filled in 2 mL vials.

L-methionine was found to be the best group 2 stabilizer for secukinumab. This was demonstrated by higher purity levels as measured by CEX and purity by RP-HPLC and lower turbidity levels and visible particles counts. A significantly better stability was shown in the presence of L-methionine as compared to a composition without stabilizer. Compositions with L-methionine had lower levels of AP-SEC, more consistent DLS data, lower turbidity and lower amounts of pre-main peak species by RP-HPLC after 8 weeks of stability at accelerated conditions of 25° C. and 40° C. EDTA was disadvantageous due to increases in AP-SEC, DLS, basic variants by CEX and pre-main peak species by RP-HPLC. Cysteine lead to increases in almost all aggregation and degradation products as indicated by various analytic methods.

FIG. 1 lists selected quality attributes after storage under different conditions. Only L-methionine was observed to have a consistently stabilizing effect on secukinumab. The stabilizing effect was especially observed on pre-main peak species by RP-HPLC (FIG. 1B) and AP-SEC (FIG. 1D). Further effects were also observed in turbidity and hydrodynamic radius by DLS. The effect of different L-methionine concentrations on secukinumab quality attributes was evaluated in subsequent studies.

Figure 2:
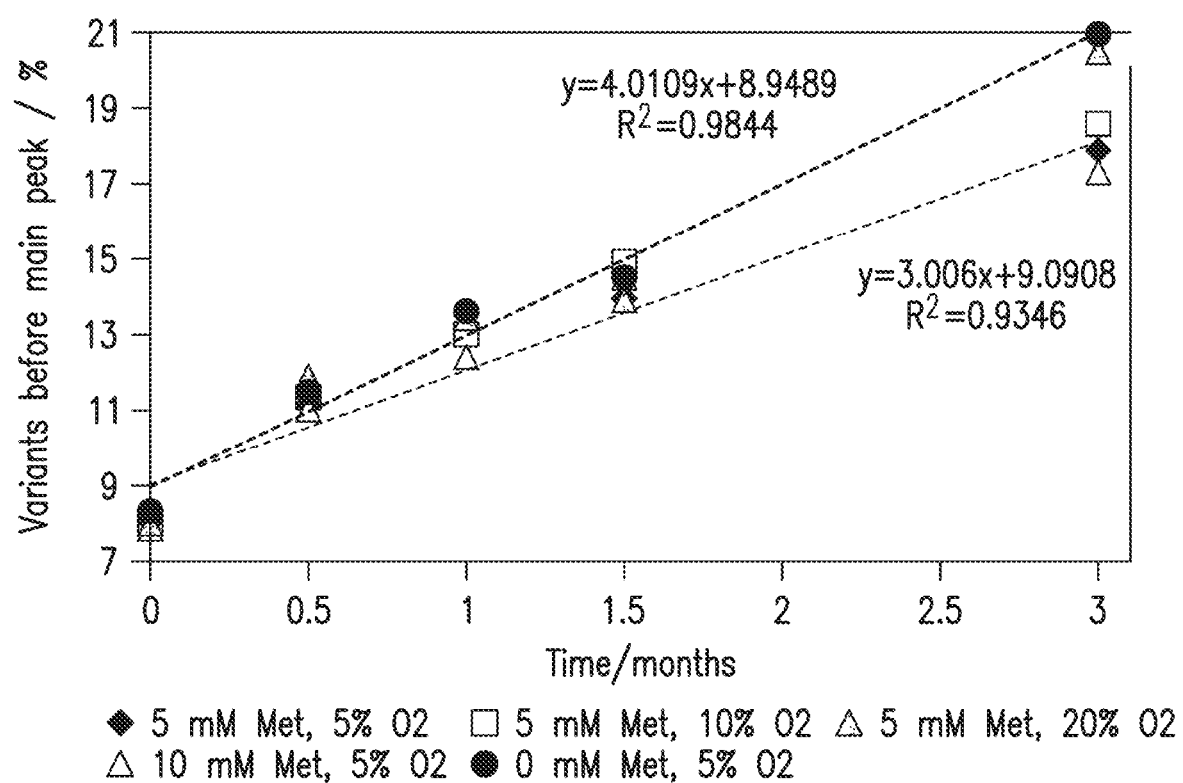
FIG. 2 shows the effect of L-methionine concentration on 25 mg/ml secukinumab stability at 25° C. storage: pre-main peak species by RP-HPLC (%). Grey dashed line: linear fit to 10 mM L-methionine/5% headspace oxygen content data; black dashed line: linear fit to 0 mM L-methionine/5% headspace oxygen content data.

FIG. 2 displays the change in pre-main peak species by RP-HPLC during storage at 25° C. at a secukinumab concentration of 25 mg/mL and a trehalose concentration of 225 mM and a polysorbate 80 concentration of 0.02% in histidine buffer pH 5.8 in the presence and absence of L-methionine. Compositions were filled into 2 mL vials and stored for up to 3 months under stressed conditions. The black dashed line represents a linear fit to the values obtained for the composition containing 0 mM L-methionine, the grey dashed line represents a linear fit to the values obtained for the composition containing 10 mM L-methionine. Clearly, reduced degradation kinetics were observed in the presence of L-methionine.

A concentration dependent effect was also observed for compositions containing 150 mg/mL secukinumab. A study was conducted with compositions containing trehalose at concentrations between 200 mM and 300 mM, polysorbate 80 between 0.01% and 0.04% as well as L-methionine from 0 mM to 10 mM. Compositions were filled into 1 mL PFS and stored for up to three months at long-term, accelerated and stressed conditions. Secukinumab physical (AP-SEC, DLS, sub-visible particles by light obscuration and visible particles, turbidity) and chemical (purity by CEX, purity by RP-HPLC, color) stability as well as biological activity were monitored FIG. 3 displays the pre-main peak species by RP-HPLC after 6 months storage at 25° C. Whereas the effect of trehalose and polysorbate 80 on degradation was negligible, clearly reduced degradation levels were observed in the presence of L-methionine. This effect was more pronounced comparing secukinumab stability with and without L-methionine, but also concentration dependence in the range of 2.5-10 mM L-methionine was observed.

Figure 4A:
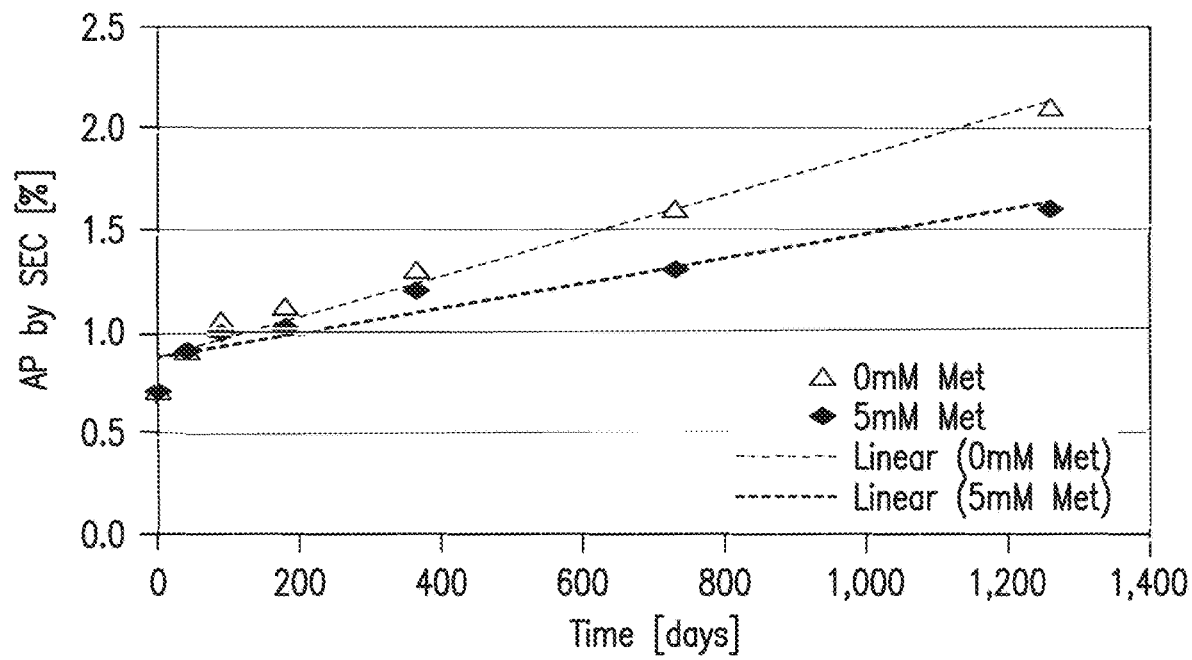
FIGS. 4A and B show the effect of L-methionine concentration on 150 mg/ml secukinumab liquid in syringe stability stored at 5° C. AP-SEC (%) (A) and pre-main peak species by RP-HPLC (%) (B) in the presence of 5 mM and 0 mM L-methionine.
Figure 4B:
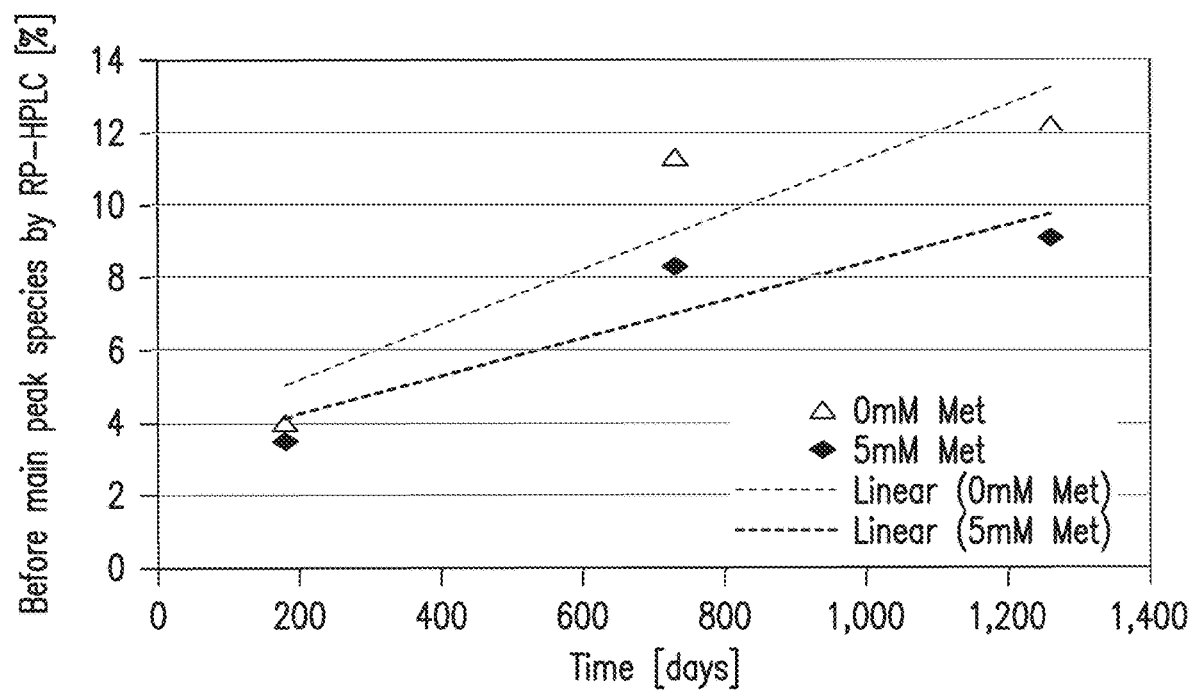

The same stabilizing effect of L-methionine was observed after long-term storage (up to 30 months) in compositions containing 150 mg/mL secukinumab, 200 mM trehalose, 0.02% polysorbate 80 in a histidine buffer pH 5.8 filled into 1 mL PFS. FIG. 4 displays AP-SEC (A) and pre-main peak species by RP-HPLC (B) during up to 30 months of storage at 5° C. The black dashed line represents a linear fit to the values obtained for the composition containing 5 mM L-methionine, the grey dashed line represents a linear fit to the values obtained for the composition containing 0 mM L-methionine. Clearly, reduced degradation kinetics were observed in the presence of L-methionine.

Figure 5A:
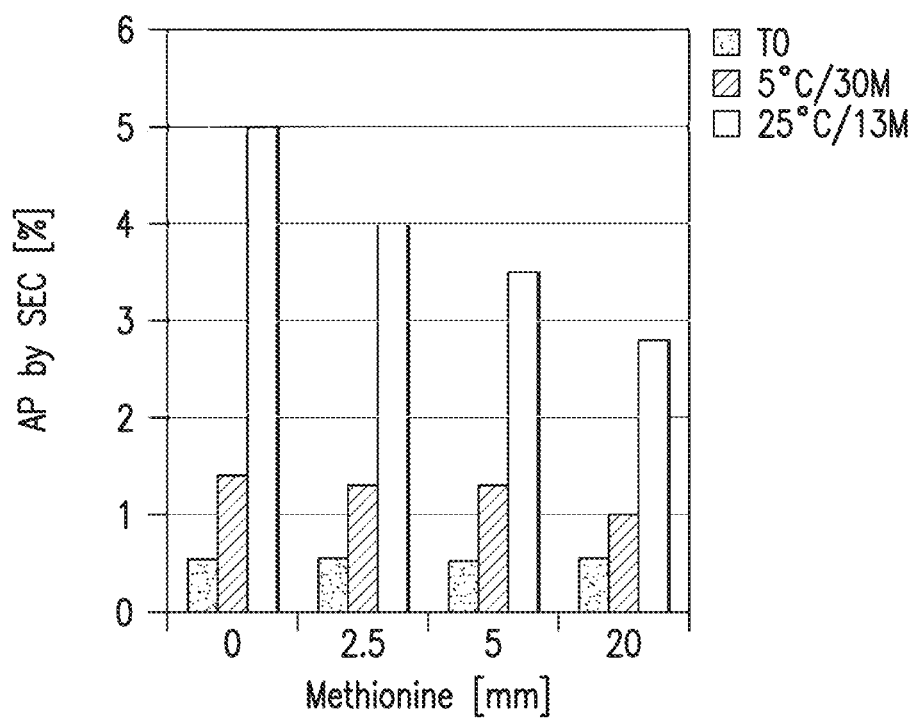
FIGS. 5A and B shows the effect of L-methionine concentration on 150 mg/ml secukinumab liquid in syringe stability after 30 months at 5° C. and 13 months at 25° C.: AP-SEC (%) (A) and pre-main peak species by RP-HPLC (%) (B).
Figure 5B:
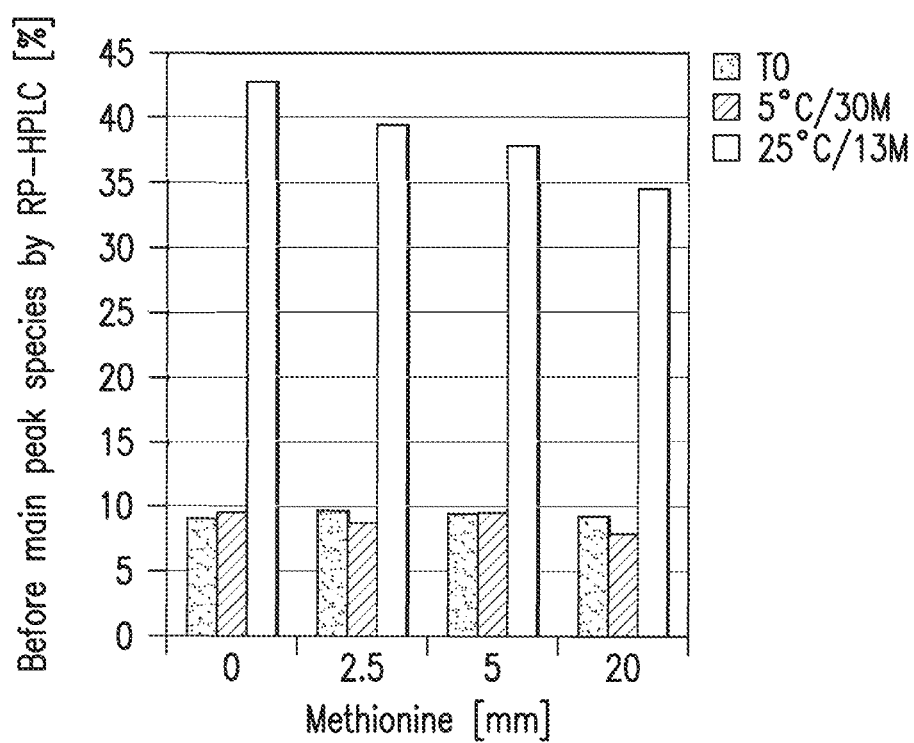

The concentration dependence was further confirmed in a study that evaluated the impact of L-methionine concentration (0-20 mM) on secukinumab stability (150 mg/mL, trehalose 200 mM, polysorbate 80 0.02%, histidine buffer pH 5.8). The different compositions were filled into PFS and stored at long-term and accelerated conditions for 13 months and 30 months (5° C. only). Secukinumab stability was assessed by a set of selected analytical techniques that was observed to be stability-indicating in previous screens (purity by RP-HPLC, purity by SEC, turbidity). No clear trend could be concluded from turbidity measurements. However, AP-SEC and pre-main peak species by RP-HPLC showed a clear dependence on the L-methionine concentration. This effect was small at real-time storage conditions, but distinct differences were observed at 25° C. (FIG. 5).

After 13 months storage at 25° C. storage, the levels of aggregates by SEC in the composition without L-methionine increased by 4.5% from a starting level of <1% at t0. With the addition of L-methionine in the composition, this increase in aggregate formation was reduced to 3.5% for 2.5 mM, 3.0% for 5 mM and 2.2% for 20 mM L-methionine. At 5° C., the difference between the composition without L-methionine and the composition with 20 mM L-methionine was only 0.3%. The pre-main peak species by RP-HPLC increased from 9.1% to 42.7% during 13 months storage at 25° C. in the sample containing 0 mM L-methionine. This increase in pre-main peak species by RP-HPLC was reduced to 39.4% for 2.5 mM, 37.8% for 5.0 mM and 34.5% for 20 mM L-methionine containing samples. In summary, reduced levels of AP-SEC and pre-main peak species by RP-HPLC were observed in the presence of L-methionine during storage at 5° C. and 25° C. in PFS. Differences were observed to be more distinct after storage at 25° C., but were also detectable after 5° C. storage.

Already at a level of 2.5 mM L-methionine, degradation rates were distinctly reduced as compared to compositions without L-methionine. This was also confirmed in a further study comparing secukinumab stability in the presence of 0, 2.5 and 5.0 mM L-methionine. No difference was observed between the composition containing 2.5 mM and 5.0 mM L-methionine in purity by RP-HPLC, purity by SEC as well as turbidity after 24 months storage at the intended storage condition.

Figure 6A:
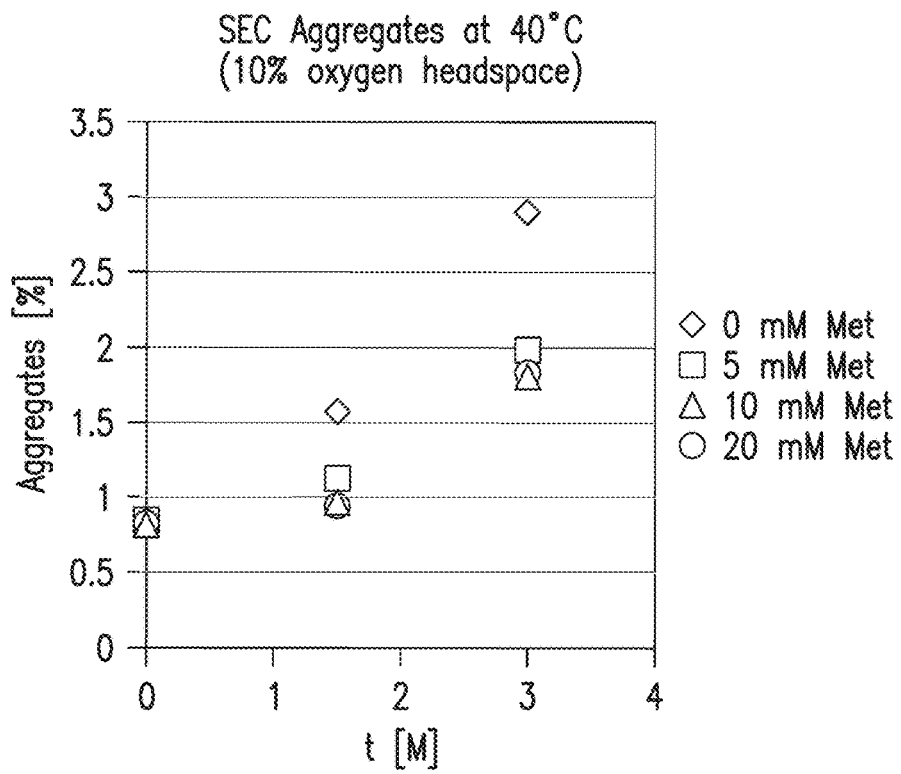
FIGS. 6A and B show the effect of L-methionine concentration on 25 mg/ml secukinumab liquid in vial (10% headspace oxygen content) stability after 3 months storage at 40° C. AP-SEC (%) (A) and sum of impurities by CE-SDS (non-reducing) (%) (B)
Figure 6B:
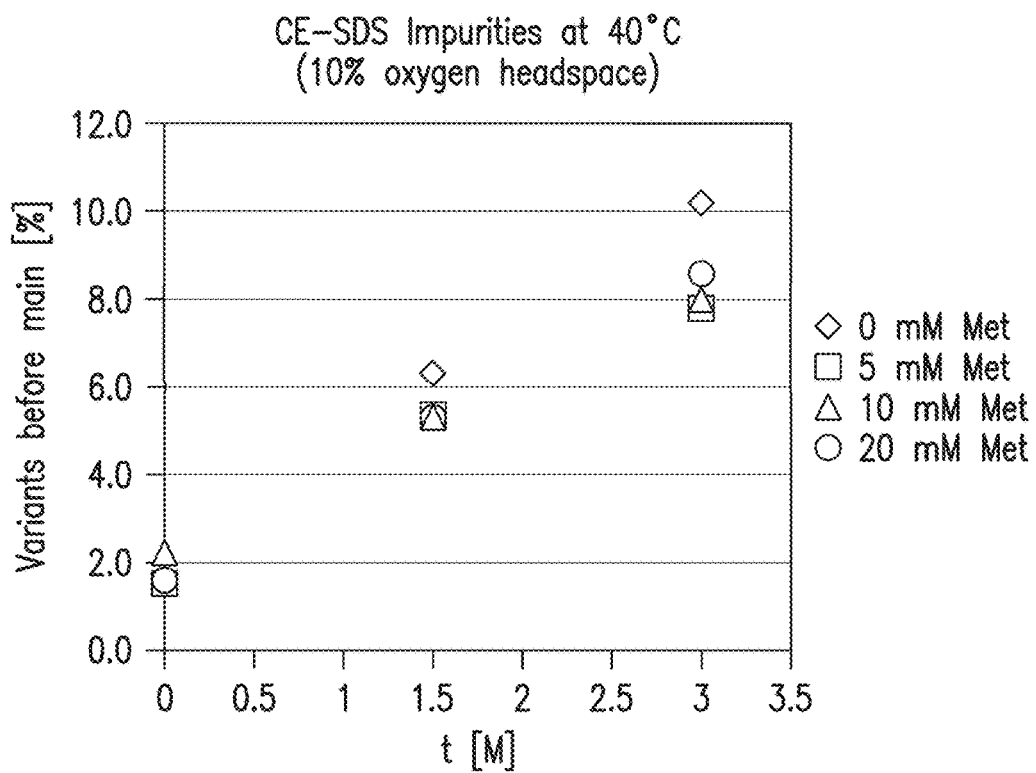

Addition of L-methionine to liquid antibody compositions in vials also decreased AP-SEC and impurities by CE-SDS (non-reducing) (FIG. 6). Interestingly, reduced L-methionine concentration dependence was observed for liquid antibody compositions in vials having 25 mg/mL secukinumab (FIG. 6), suggesting that a lower concentration of L-methionine is sufficient to maintain the integrity and stability of antibody in compositions having lower antibody concentration.

Based on the combined data from the above experiments, a methionine concentration of at least 2.5 mM (preferably about 5 mM) is ideal for liquid compositions of secukinumab, and is superior to other group 2 stabilizers.

Example 2: Headspace Oxygen Content 1.1.2.1 Primary Packaging—PFS:

The effect of headspace oxygen content on secukinumab stability was evaluated at a concentration of 150 mg/mL secukinumab and in a composition with 200 mM trehalose, 5 mM L-methionine, 0.02% polysorbate 80 in a histidine buffer pH 5.8. Compositions were filled into 1 mL PFS from various PFS suppliers. The headspace oxygen content was measured to be either between 13% and 15% (0.5 mL fill volume) or between 3-4% (0.5 mL fill volume)/7-8% (1.0 mL fill volume), respectively. The samples were stored for up to six months at long-term, accelerated and stressed conditions. Selected compositions were stored for up to 24 months under long-term conditions. Secukinumab stability was monitored by purity by SEC, purity by RP-HPLC, purity by CEX, purity by CE-SDS (non-reducing), turbidity, color, free SH-groups, biological activity, sub-visible by light obscuration and visible particles.

Figure 7:
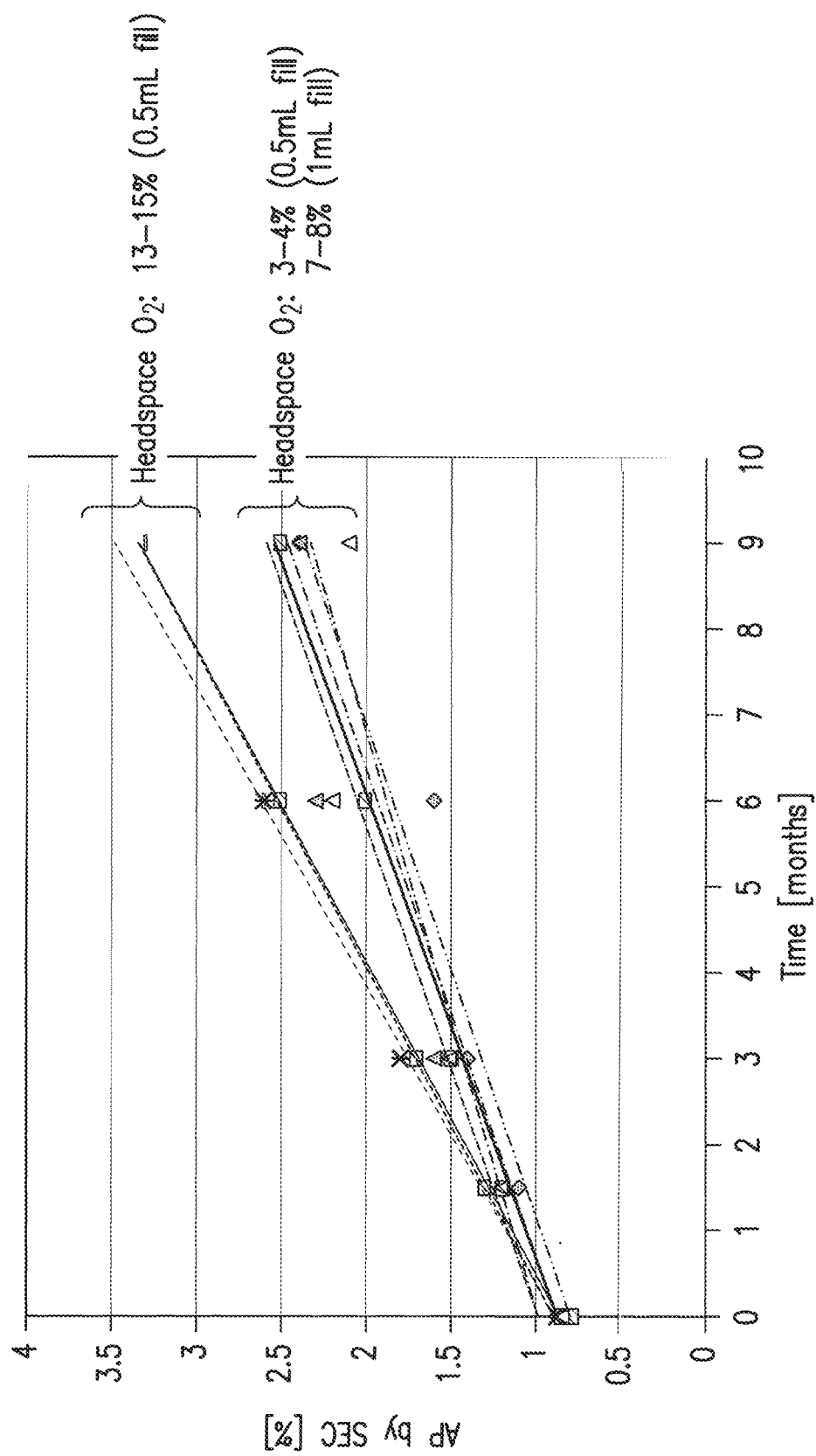
FIG. 7 shows the effect of headspace oxygen content on 150 mg/ml secukinumab liquid in Syringe stored at 25° C.: AP-SEC (%).
Figure 8A:
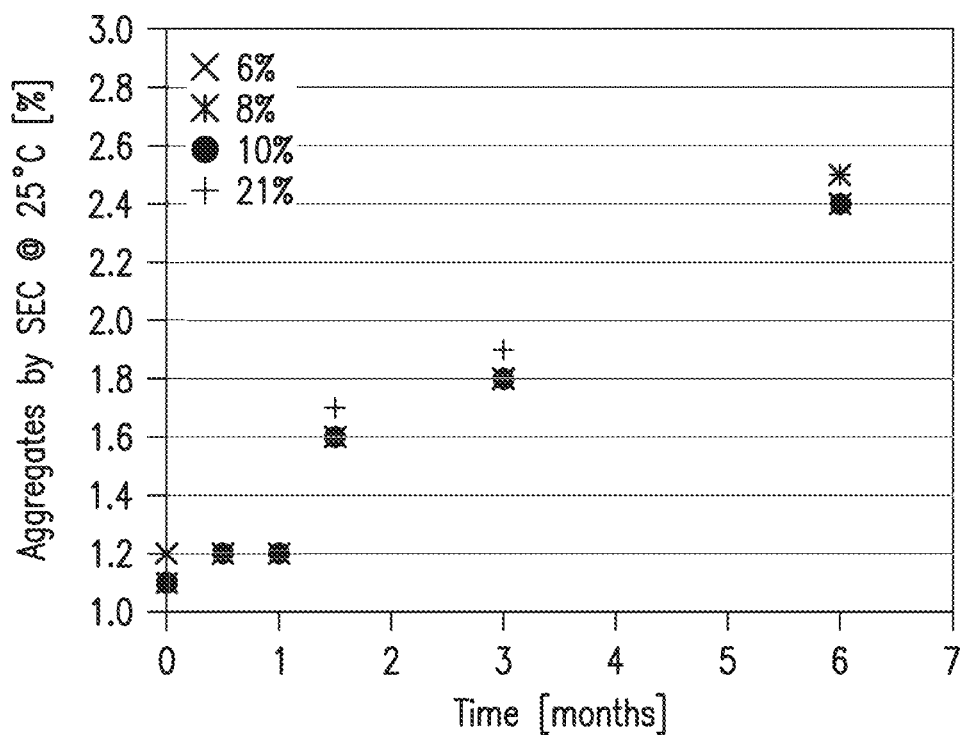
FIG. 8A-D show the effect of headspace oxygen content and fill volume on AP-SEC (%) in 150 mg/ml secukinumab liquid in syringe after storage at 25° C. (A, B) and 5° C. (C, D). Fill volume for A & C is 0.5 mL. Fill volume for B & D is 1.0 mL.
Figure 8B:
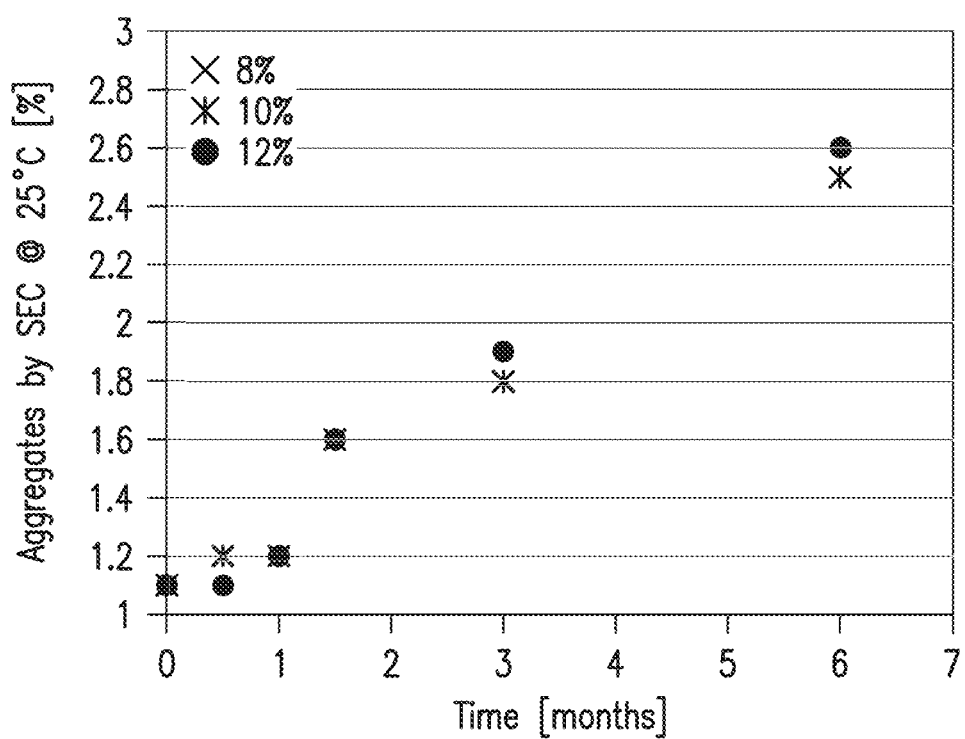
Figure 8C:
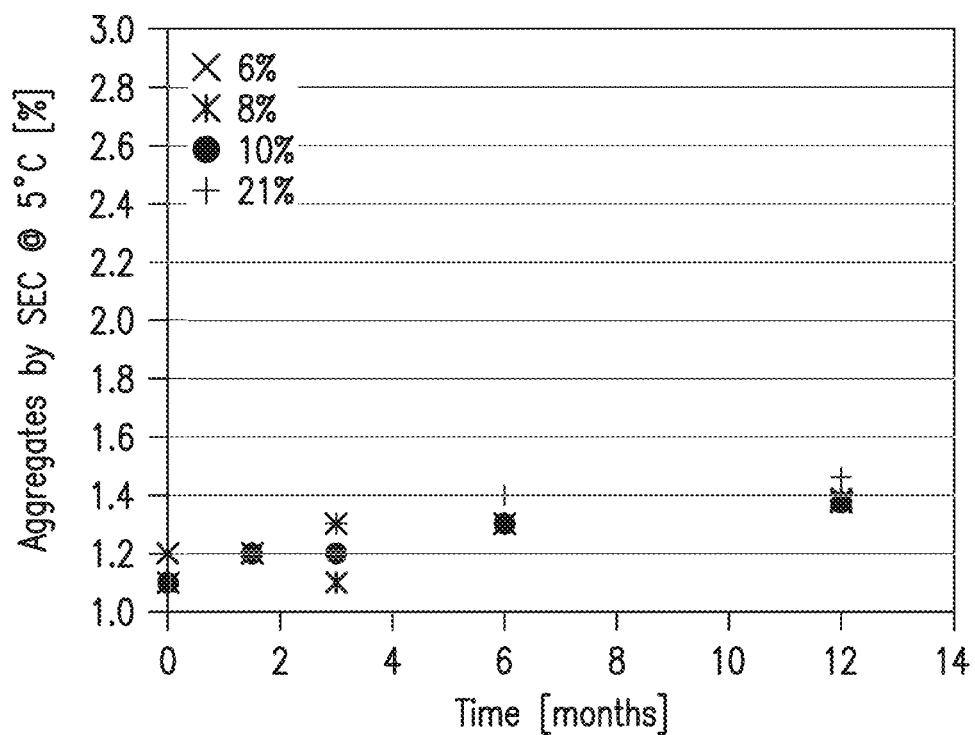
Figure 8D:
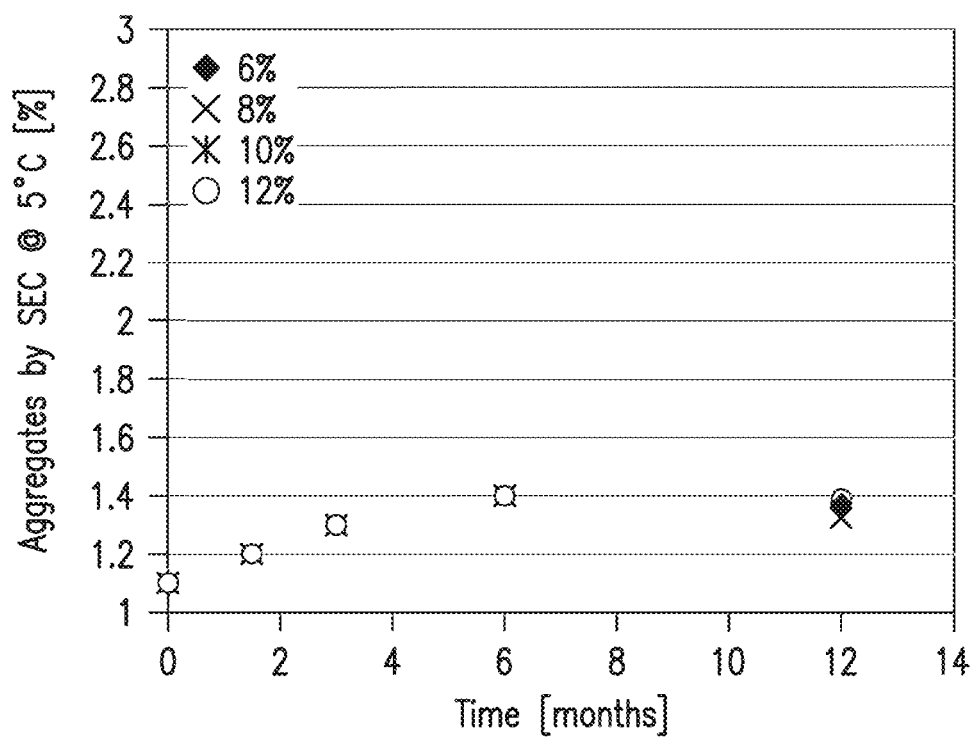

An impact of headspace oxygen content was observed on pre-main peak species by RP-HPLC and AP-SEC at long-term, accelerated and stressed conditions. FIG. 7 displays AP-SEC during up to 9 months storage at 25° C. Clearly, PFS with a headspace oxygen content between 13-15% showed increased aggregation at 25° C. However, there was little absolute difference in aggregate level relative to headspace oxygen content at 2-8° C. storage conditions (6 months data) (data not shown).

The impact of different headspace oxygen content levels ranging from 6% to 21% (i.e. not purged) on secukinumab quality attributes (turbidity, purity by SEC, purity by RP-HPLC, purity by CE-SDS (non-reducing), free SH groups, biological activity, sub-visible particles by light obscuration, visible particles, color) was further evaluated during storage at 5° C. for 12 months as well as under accelerated conditions (25° C.) for 6 months and under stressed conditions (40° C.) for 3 months. The study was performed at 150 mg/mL secukinumab and in a composition with 200 mM trehalose, 5 mM L-methionine, 0.02% polysorbate 80 in a histidine buffer pH 5.8. Samples were filled into PFS and purged with certified oxygen mixtures to yield the targeted headspace oxygen content.

Over storage time no change was observed in turbidity; no distinct effect of headspace oxygen content on sub-visible particles by light obscuration, color and free SH-groups was observed and differences between the different headspace oxygen content samples were within the scatter of the method. The methionine concentration did not relevantly change during storage at 5° C. or 25° C. and was observed to be 4.9 mM (initial value 4.9-5.0 mM) after 12 months at 5° C. regardless of the headspace oxygen content.

Figure 9:
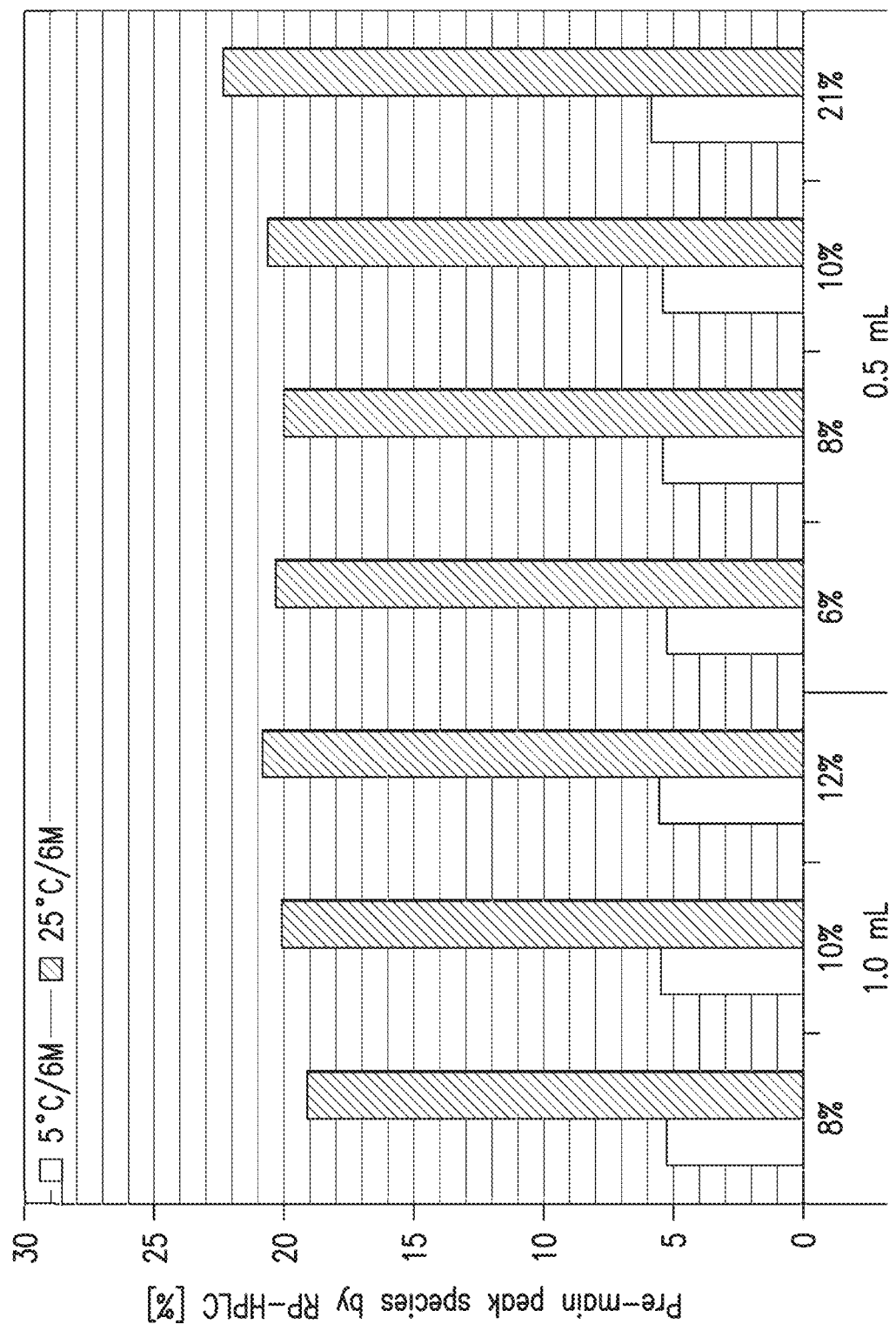
FIG. 9 shows the effect of headspace oxygen content and fill volume on 150 mg/ml secukinumab liquid in syringe stability after 6 months at 5° C. and 25° C.: purity by RP-HPLC.

In contrast to our earlier findings, which showed a relatively large impact of headspace oxygen content on aggregation products by SEC, in this experiment only small changes were observed during storage up to 12 months at the intended storage condition (5° C.), even in the non-purged reference sample. No relevant differences in purity and aggregates by SEC were observed between samples with different oxygen levels in the headspace for the different stability points tested (up to 12 months storage at 2-8° C. and up to 6 months storage at 25° C.) (FIG. 8). In contrast, we did note an increase in main purity by RP-HPLC with increasing headspace oxygen content. This was observed at 5° C. (after 12 months of storage) (data not shown) and at 25° C. (after 6 months of storage) (FIG. 9). No new peaks appeared.

1.1.2.2 Primary Packaging—Vials:

Compositions were filled into 2 mL vials and stored for 12 months at refrigerated conditions and up to 3 months under accelerated and stressed conditions. Tables 5-7 summarize the change in pre-main peak species by RP-HPLC and SEC-AP during storage at 5° C., 25° C. and 40° C. at a secukinumab concentration of 25 mg/mL and a trehalose concentration of 225 mM and a polysorbate 80 concentration of 0.02% in histidine buffer pH 5.8 in the presence and absence of 5 mM L-methionine.

TABLE 5

RP-HPLC and SEC results for 25 mg/ml secukinumab liquid in vial after 6 and 12-months storage at 5° C. Composition 25 mg/ml secukinumab, 225 mM trehalose, 5 mM L-methionine, 0.02% PS80.

| Headspace oxygen content | Pre-main peak species by RP-HPLC (%) | | | AP-SEC (%) | | |
|---|---|---|---|---|---|---|
| | T0 | 6 M | 12 M | T0 | 6 M | 12 M |
| 5% | — | — | 4.5 | — | — | 0.81 |
| 10% | 8.2 | 3.4 | 6.1 | 0.84 | 0.78 | 0.86 |
| 20% | — | 4.2 | 7.1 | — | 0.79 | 0.91 |

TABLE 6

RP-HPLC and SEC results for 25 mg/ml secukinumab liquid in vial after 3 months storage at 25° C. and 40° C. Composition 25 mg/ml secukinumab, 225 mM trehalose, 5 mM L-methionine, 0.02% PS80.

| Headspace oxygen content | Pre-main peak species by RP-HPLC (%) | | | AP-SEC (%) | | |
|---|---|---|---|---|---|---|
| | T0 | 25° C. 3 M | 40° C. 3 M | T0 | 25° C. 3 M | 40° C. 3 M |
| 5% | — | 17.9 | 40.6 | — | 1.10 | 1.80 |
| 10% | 8.0 | 18.4 | 43.1 | 0.84 | 1.00 | 2.00 |
| 20% | — | 20.6 | 46.2 | — | 0.93 | 2.50 |

TABLE 7

RP-HPLC and SEC results for 25 mg/ml secukinumab liquid in vial after 6 and 12-months storage at 5° C. Composition 25 mg/ml secukinumab, 225 mM trehalose, 0 mM L-methionine, 0.02% PS80.

| Headspace oxygen content | Pre-main peak species by RP-HPLC (%) | | | AP-SEC (%) | | |
|---|---|---|---|---|---|---|
| | T0 | 6 M | 12 M | T0 | 6 M | 12 M |
| 5% | 8.3 | 3.8 | 6.1 | 0.84 | 0.82 | 0.91 |

TABLE 8

RP-HPLC and SEC results for 25 mg/ml secukinumab
liquid in vial after 3 months storage at 25°
C. and 40° C. Composition 25 mg/ml secukinumab,
225 mM trehalose, 0 mM L-methionine, 0.02% PS80.

| Headspace oxygen content | Pre-main peak species by RP-HPLC (%) | | | AP-SEC (%) | | |
|---|---|---|---|---|---|---|
| | T0 | 25° C. 3 M | 40° C. 3 M | T0 | 25° C. 3 M | 40° C. 3 M |
| 5% | — | 20.9 | 44.6 | — | 1.10 | 2.60 |
| 10% | 8.3 | 21.4 | 46.7 | 0.84 | 1.10 | 2.90 |
| 20% | — | 25.5 | 50.9 | — | 1.30 | 3.50 |

An impact of headspace oxygen content on 25 mg/ml secukinumab liquid in vial stability is seen by pre-main peak species by RP-HPLC after 12 months at 5° C. (4.5% at 5% headspace oxygen content vs. 7.1% at 20% headspace oxygen content, see Table 5), after 3 months at 25° C. (17.9% at 5% headspace oxygen content vs. 20.6% at 20% oxygen, see Table 6) and after 3 months at 40° C. (40.6% at 5% headspace oxygen content vs. 46.2% at 20% headspace oxygen content, see Table 6). The same trend is deductible for AP-SEC after 3 months at 40° C. (1.8% at 5% headspace oxygen content vs. 2.5% at 20% headspace oxygen content, see Table 6). Moreover, L-methionine concentration has a further impact when combined with lower headspace oxygen content. For example, comparing pre-main peak species by RP-HPLC in the compositions containing 5% oxygen headspace content data after 12 months storage at 5° C., 6.1% (Table 7) were found for the composition containing no L-methionine as compared to 4.5% (Table 5) for the composition with 5 mM L-Methionine. The same difference is seen for pre-main peak species by RP-HPLC after 3 months at 25° C. (5%-20% oxygen: 20.9-25.5% in absence of L-methionine (Table 8) vs. 17.9-25.5% in presence of 5 mM L-methionine (Table 6)), and after 3 months at 40° C. (5%-20% oxygen: 44.6-50.9% in absence of L-methionine (Table 8) vs. 40.6-46.2% in presence of 5 mM L-methionine (Table 6)).

Based on the above experiments, a nitrogen purge to decrease the headspace oxygen content to less than about 12% is viewed as beneficial in enhancing the stability of the liquid composition in both PFS and vials (as assessed by pre-main peak species by RP-HPLC).

Figure 10:
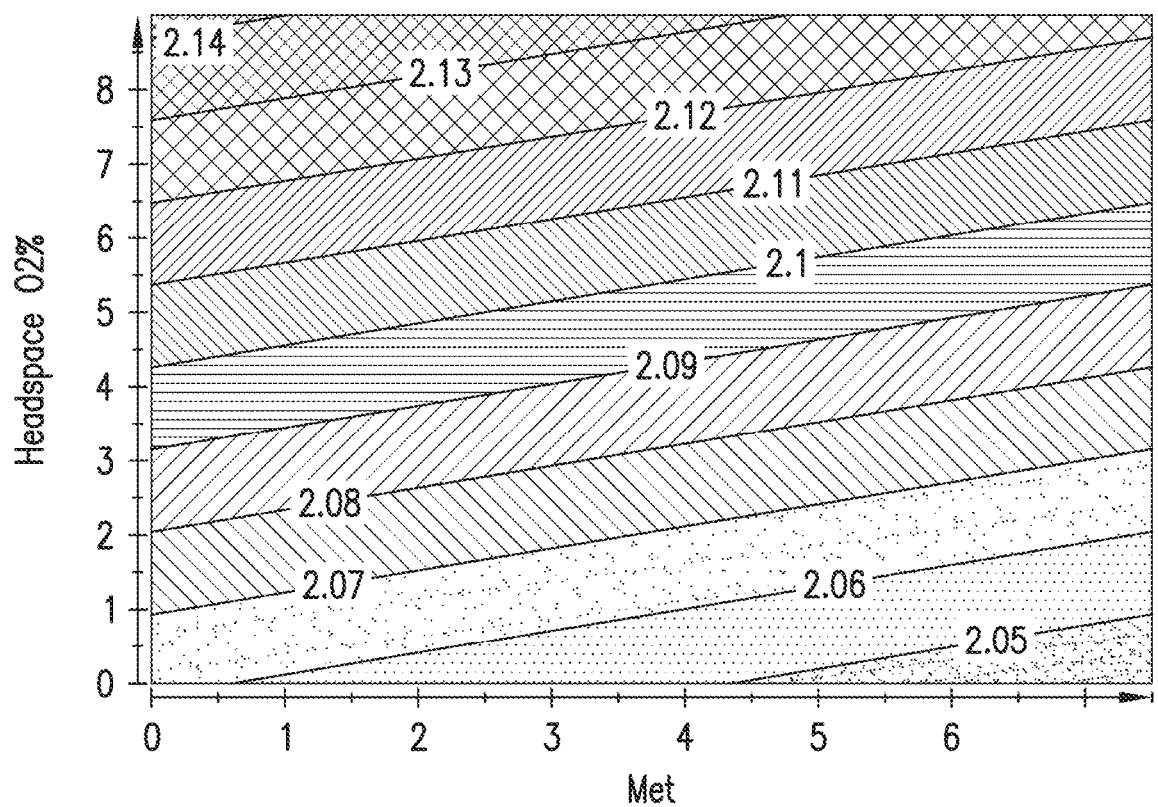
FIG. 10 shows the effect of L-methionine concentration and headspace oxygen content on 150 mg/ml secukinumab liquid in syringe stability after 6 months storage at 25° C. (A): AP-SEC (%)

Example 3: Interaction of L-Methionine Concentration and Headspace Oxygen Content A further study evaluated the interaction between the L-methionine concentration and the headspace oxygen content. Compositions containing L-methionine in a range of 2.5-7.5 mM and headspace oxygen content between 3 and 9% were prepared. Compositions were filled into PFS and stored under long-term and accelerated conditions for 6 months. Relevant secukinumab quality attributes (purity by SEC, purity by RP-HPLC, purity by CEX, free SH-groups, biological activity, sub-visible and visible particles by light obscuration, turbidity and color of the solution) were monitored after 3 and 6 months storage. FIG. 10 displays purity by AP-SEC after 6 months storage at 25° C. as a function of L-methionine and headspace oxygen content. No interaction was observed in the tested range when analyzed using purity by AP-SEC.

In another study, the effect of reduced headspace oxygen content and L-methionine concentration was evaluated at secukinumab concentration of 150 mg/mL. The compositions comprised 270 mM mannitol, 0.04% polysorbate 80 and different L-methionine concentrations ranging from 0.15% to 2%. Compositions were filled into 2 mL glass vials, either purged with nitrogen or not and stored at long-term, accelerated and stressed conditions for up to 6 months.

Figure 11:
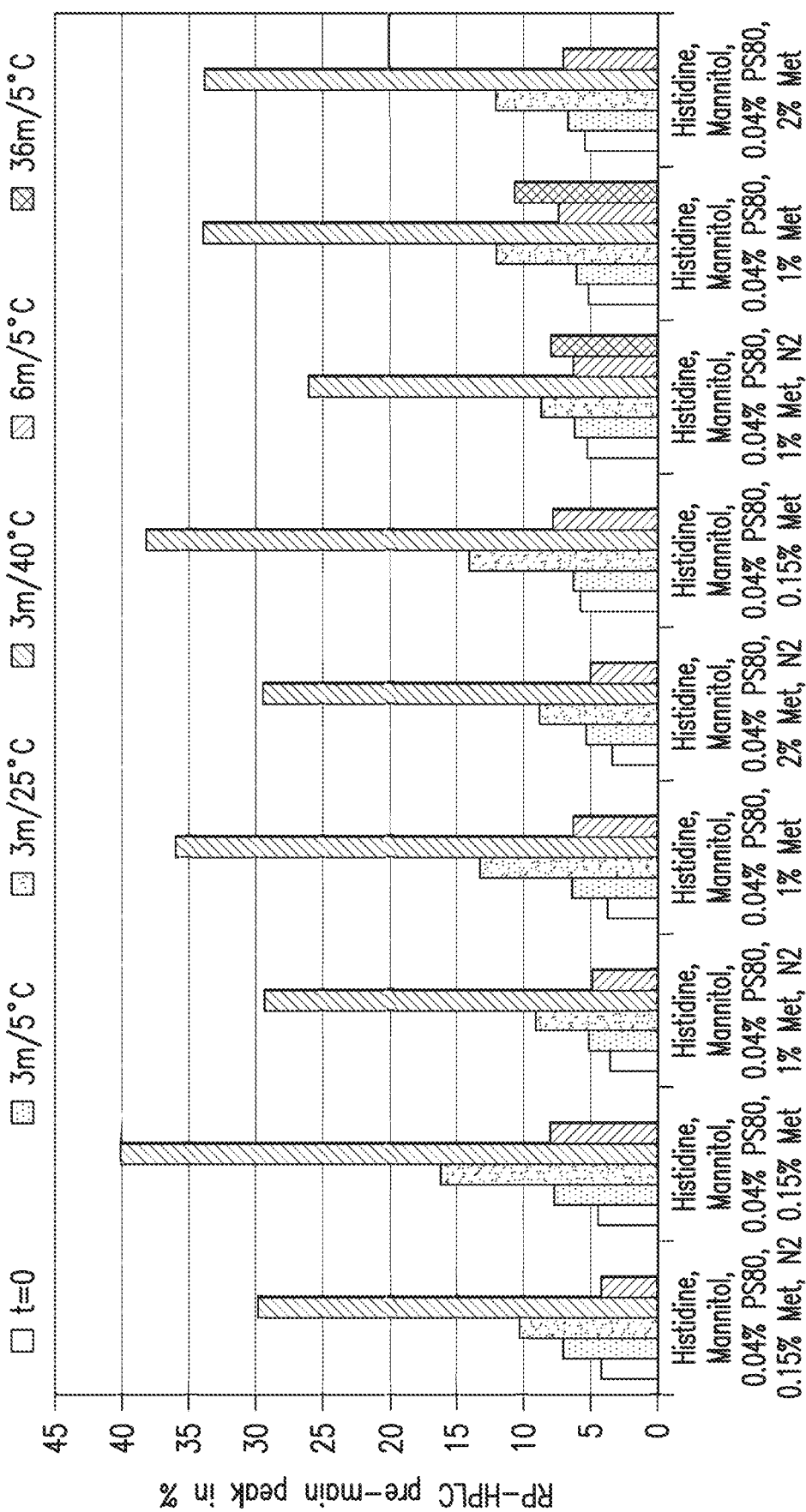
FIG. 11 shows the effect of nitrogen purge and L-methionine concentration on 150 mg/ml secukinumab liquid in syringe stability: pre-main peak species by RP-HPLC (%).

FIG. 11 depicts pre-main peak species by RP-HPLC after up to 36 months storage in compositions containing 0.15% (10 mM), 1% (67 mM) or 2% (134 mM) L-methionine and either a nitrogen or air headspace. As observed before, pre-main peak species by RP-HPLC were at a lower level in compositions containing higher amounts of L-methionine. The same composition showed lower levels of pre-main peak species by RP-HPLC when the headspace was purged with nitrogen.

Based on the combined data from various experiments using both vials and PFS as primary packaging, a headspace oxygen content of less than about 12% in combination with an L-methionine concentration of at least about 2.5 mM is ideal for liquid compositions of secukinumab.

Example 4: pH

The effect of pH on secukinumab stability was initially evaluated at a concentration of 10 mg/ml in 100 mM citric acid/sodium phosphate buffer containing 90 mM sodium chloride in a pH range between 4.0 and 7.5. Samples were stored for 3 weeks at 5° C. and 40° C. In parallel, secukinumab stability after five freeze thaw cycles from ≤−60° C. to room temperature was monitored.

The optimal pH for secukinumab varied depending on the degradation pathway analyzed. Aggregation and proteolysis determined by purity by SEC, purity by SDS-PAGE (reducing) and the average molecular weight by LLS were minimal at pH 5.7 to 6.2, whereas optimal pH for purity by CEX was pH 5.3. Active secukinumab contains one free Cysteine residue on each light chain, thus, 2 Mol thiol groups/Mol secukinumab are expected. Since a reduced level of free SH-groups correlates with loss of biological activity in secukinumab, the free SH-groups were quantified using a method based on Ellman's reagent. Only at pH 4.3, a slightly lower value of 1.94 Mol/Mol was observed. The secukinumab freeze thaw resistance monitored by purity by SEC and the average molecular weight by LLS was maximum at pH 5.3 to 5.7. A pH 5.8 was selected for further formulating secukinumab.

Figure 12A:
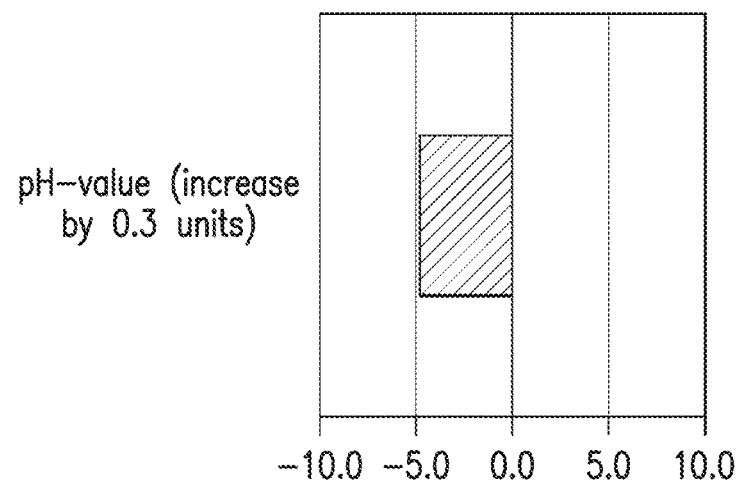
FIGS. 12A and B show the effect of pH on 150 mg/ml secukinumab liquid in syringe stability after 4 weeks storage at 40° C.: scaled estimates/2 (effect of increase in pH by 0.3 units) for stability pre-main peak species by RP-HPLC (% change) (A) and AP-SEC (% change) (B).
Figure 12B:
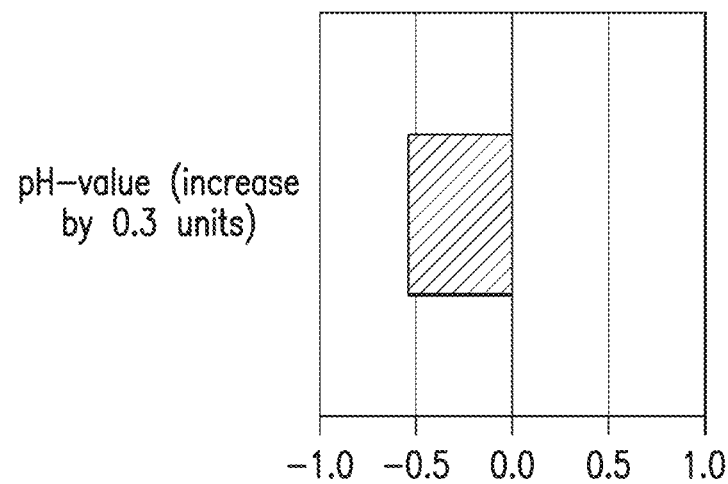
Figure 13A:
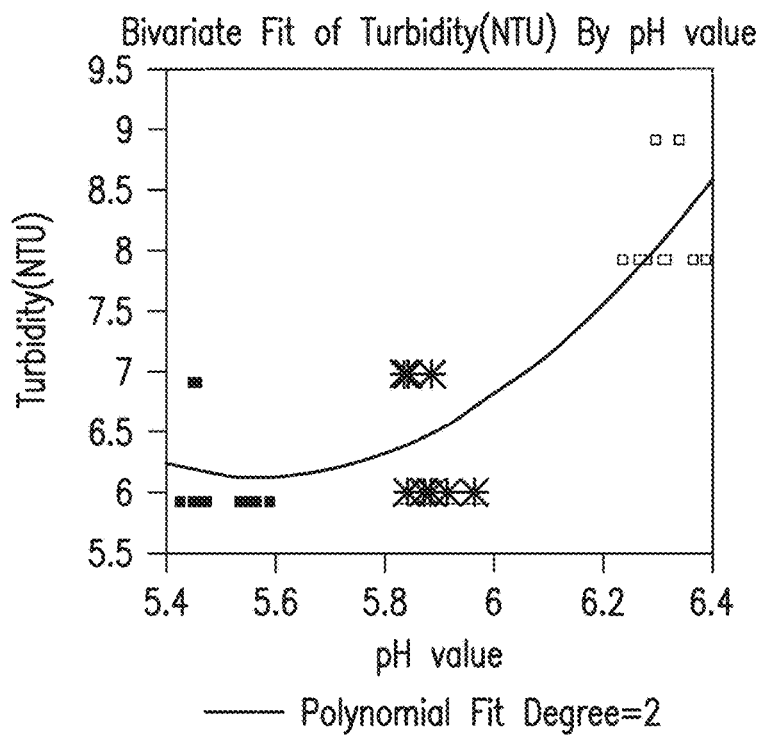
FIG. 13A-D show the effect of pH on 150 mg/ml secukinumab Liquid in Syringe stability after storage at 5° C.: Turbidity (NTU) (A), Purity by SEC (%) (B), Acidic variants by CEX (%) (C), AP-SEC (%) (D).
Figure 13B:
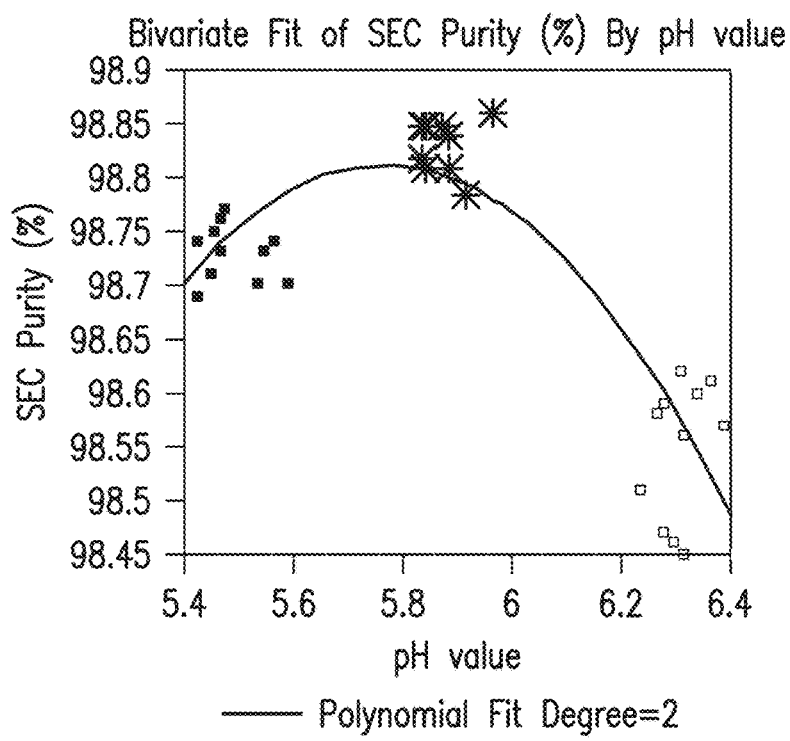
Figure 13C:
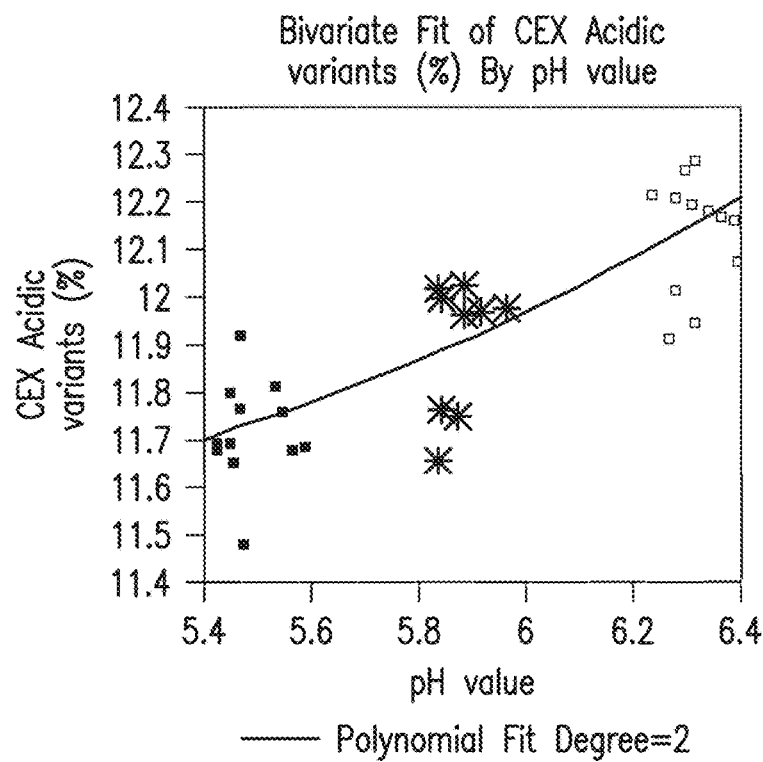
Figure 13D:
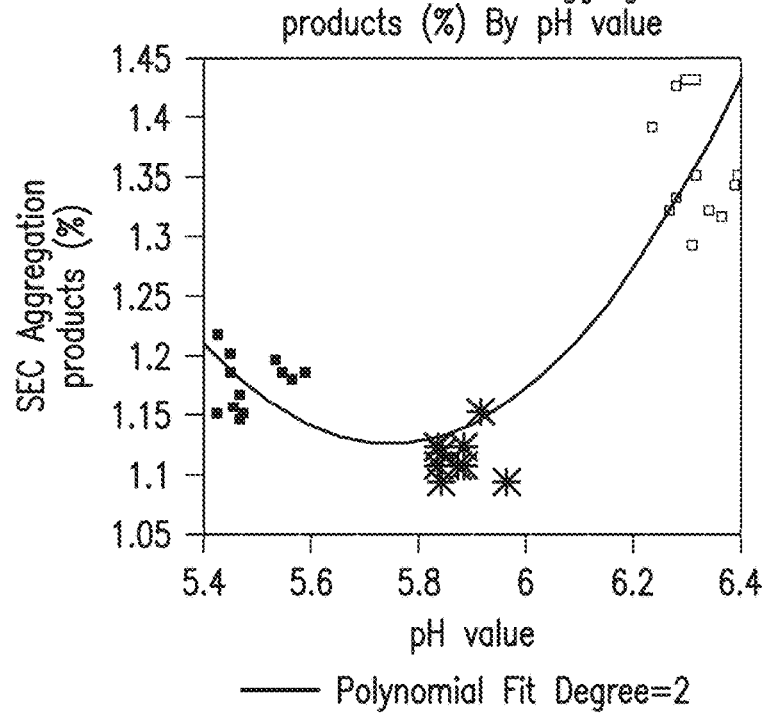

Further studies on the effect of pH on secukinumab stability were conducted in PFS using a DoE approach. The effect of pH in the range of 5.2-5.8 was evaluated at a secukinumab concentration of 150 mg/mL. Compositions were placed on a 2 months stability study at long-term (5° C.), accelerated (25° C.) and stressed (40° C.) conditions and were evaluated with regards to physical stability (AP-SEC, DLS, turbidity, visible particles and sub-visible particles by light obscuration), chemical stability (purity by CEX, purity by RP-HPLC, color) and indicators of biological activity (activity by Cys-CEX, free SH-groups). In addition, freeze-thaw (5 cycles of −20° C. to room temperature) and shaking stress (150 rpm for one week) was applied to compositions filled in 2 mL vials. pH-values in the investigated range were found to significantly impact secukinumab stability (AP-SEC, DP-SEC, DLS, basic variants by CEX, purity by RP-HPLC). Results from earlier studies were confirmed with regard to pH 5.8 as ideal (AP-SEC, DP-SEC and pre-main peak species by RP-HPLC) (FIG. 12).

The effect of pH was further evaluated in compositions containing secukinumab at a concentration of 150 mg/mL, trehalose 200 mM, L-methionine in a range of 2.5-7.5 mM and headspace oxygen content between 3 and 9%. The pH of the histidine buffer was varied between 5.4 and 6.2. Compositions were filled into PFS and stored under long-term and accelerated conditions for 6 months. Relevant secukinumab quality attributes (purity by SEC, purity by RP-HPLC; purity by CEX, free SH-groups, biological activity, sub-visible particles by light obscuration, visible particles, turbidity and color of the solution,) were monitored after 3 and 6 months storage. FIG. 13 depicts the effect of pH on secukinumab quality attributes after storage at 5° C. Increased turbidity, AP-SEC and acidic variants by CEX as well as decreased purity by SEC were observed at higher pH values, further confirming observations from the initial screen.

Based on the combined data from various experiments, a pH range from about 5.2 to about 6.2 is ideal for liquid compositions of secukinumab.

Part 2—Detailed Analysis of Excipients with Smaller Influence on Secukinumab Liquid State Stability (Stabilizer, Surfactant and Buffer)

Example 5: The Choice of Stabilizer has Little Influence on Stability

Initial composition development for the liquid dosage form focused on the evaluation of different stabilizers with regards to secukinumab soluble and insoluble aggregate formation (AP-SEC, purity by SDS-PAGE, light scattering techniques), chemical stability (purity by RP-HPLC, purity by CEX, color) and biological activity (activity by Cys-CEX, free SH-groups, biological activity) during storage at long-term storage condition as well as accelerated and stressed conditions.

Stabilizers were divided into three different classes: Group I comprised non-ionic (mannitol, trehalose dihydrate) and ionic (sodium chloride and arginine hydrochloride) stabilizers. All group 1 stabilizers provided benefit over no stabilizer. However, non-ionic stabilizers (trehalose and mannitol) were observed to better stabilize the molecule as observed by lower aggregate levels and higher activity by Cys-CEX.

Figure 14:
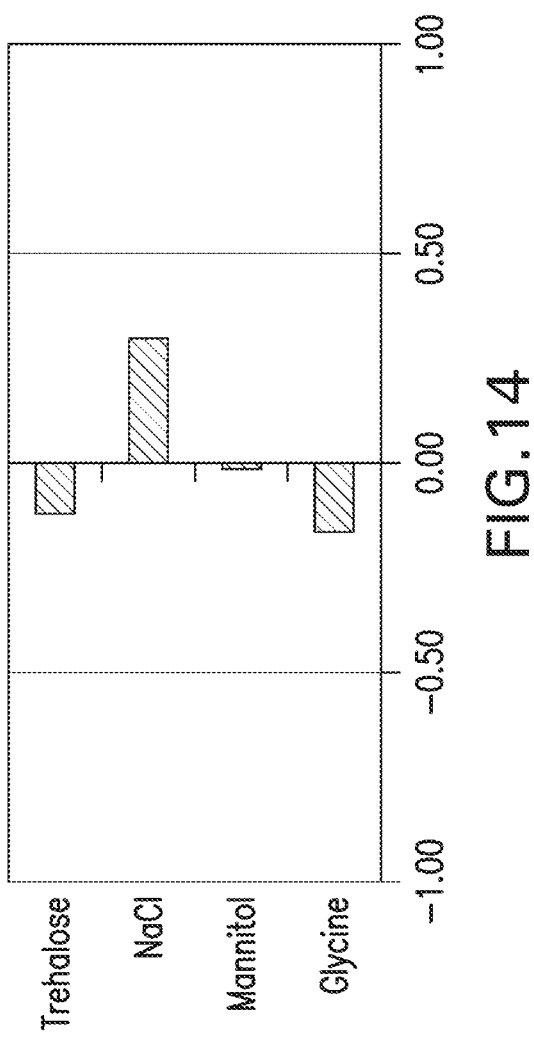
FIG. 14 shows the impact of stabilizer on 150 mg/ml secukinumab liquid in syringe stability after 8 weeks storage at 25° C.: parameter estimates for AP-SEC.

Based on the conclusions from the initial composition development studies, further studies were conducted in PFS using a DoE approach. The effect of stabilizer group I (glycine, mannitol, trehalose dihydrate, sodium chloride) was evaluated. The compositions were filled in pre-filled syringes and placed on a 2 months stability study at long-term, accelerated and stressed conditions and were evaluated with regards to physical stability (AP-SEC, DLS, turbidity, visible and sub-visible particles by light obscuration), chemical stability (purity by CEX, purity by RP-HPLC, color) and indicators of biological activity (activity by Cys-CEX, free SH-groups). In addition, freeze-thaw (5 cycles of −20° C. to room temperature) and shaking stress (150 rpm for one week) was applied to compositions filled in 2 mL vials. With regards to stabilizer class I, observations from earlier screens were confirmed: 1) all group 1 stabilizers provided benefit over no stabilizer; and 2) non-ionic stabilizers were found to be better stabilizers for secukinumab protein (FIG. 14). This was especially prominent in purity by SEC, purity by RP-HPLC and polydispersity by DLS. Comparing different non-ionic stabilizers, no relevant effect was observed.

Figure 3:
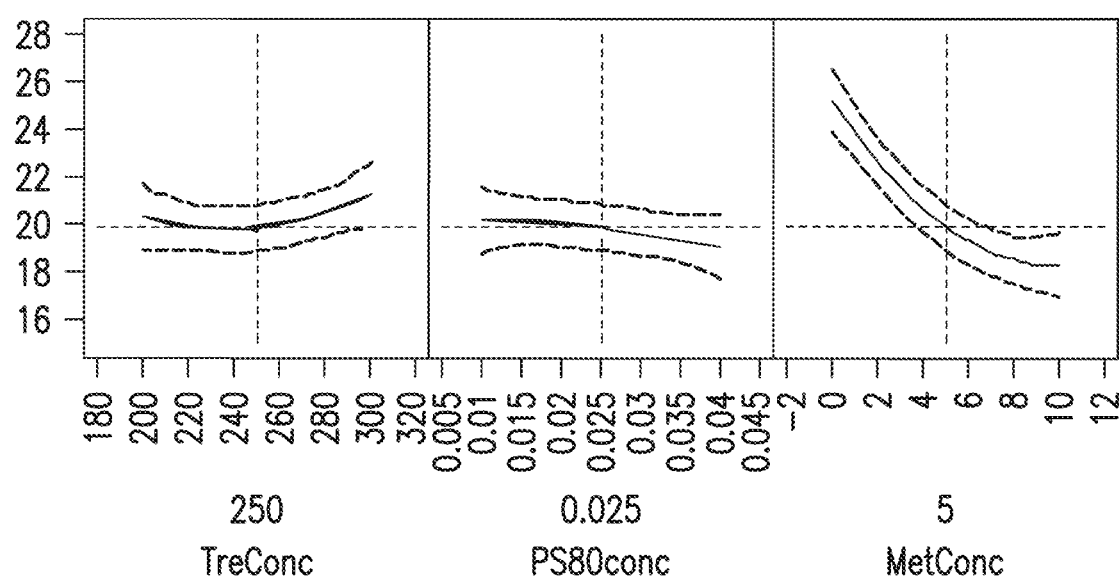
FIG. 3 shows the effect of L-methionine, trehalose and polysorbate 80 on 150 mg/ml secukinumab liquid in syringe stability stored for 6 months at 25° C.: pre-main peak species by RP-HPLC (%).

Next, we identified the ideal concentration of the stabilizer class I (trehalose dihydrate, 200-300 mM). Samples were filled in PFS and stored for up to three months at long-term, accelerated and stressed conditions. Secukinumab physical (AP-SEC, DLS, sub-visible particles by light obscuration, visible particles, turbidity) and chemical (purity by CEX, purity by RP-HPLC, color) stability as well as biological activity were monitored. No relevant difference in secukinumab quality attributes was observed with varying trehalose concentrations (FIG. 3).

Example 6: The Choice of Surfactant has Little Influence on Stability

Initial composition development for the 150 mg/ml liquid composition focused on the evaluation of different excipients (e.g., stabilizers and surfactants) with regards to secukinumab soluble and insoluble aggregate formation (AP-SEC, purity by SDS-PAGE, light scattering techniques), chemical stability (purity by RP-HPLC, purity by CEX, color) and biological activity (activity by Cys-CEX, free SH-groups, biological activity) during storage at long-term storage condition as well as accelerated and stressed conditions. Excipients were divided into three different classes: Group III comprised the surfactants polysorbate 20 and 80. No difference was observed between polysorbate 20 and 80 at a concentration of 0.04% as compared to no surfactant during quiescent storage.

Figure 15:
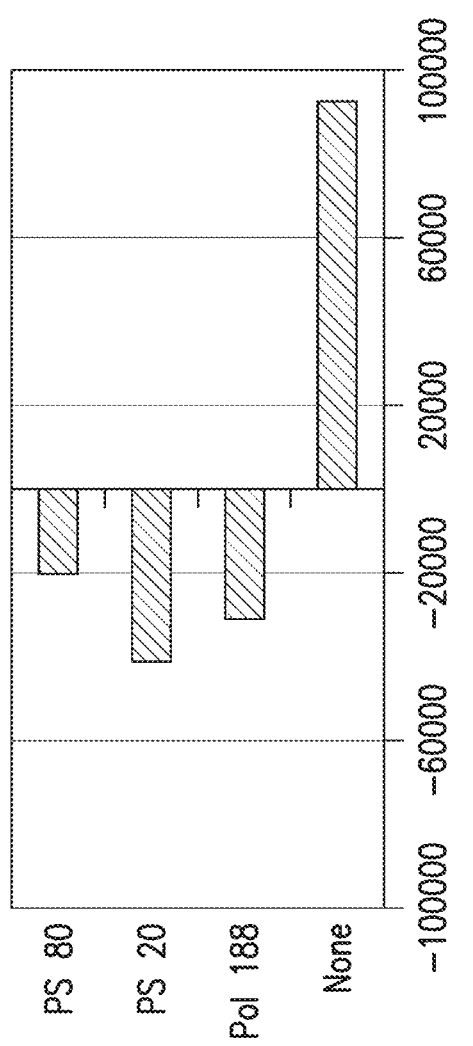
FIG. 15 shows the effect of surfactant on 150 mg/ml secukinumab liquid in syringe stability after shaking: Parameter estimates for sub-visible particles ≥1 μm by light obscuration (particles per ml).
Figure 16B:
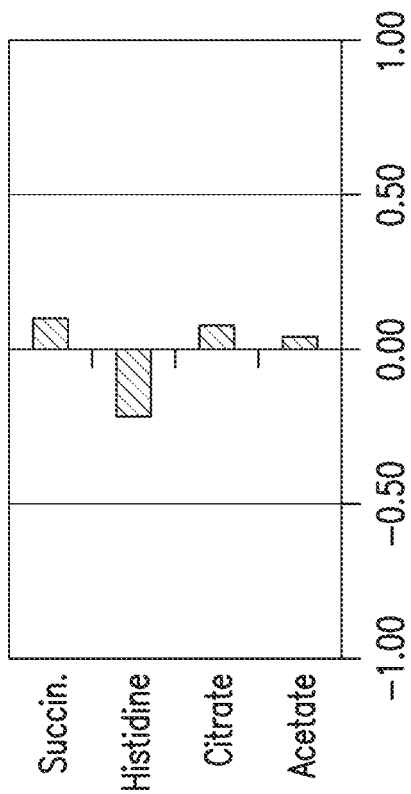
FIG. 16A-D shows the effect of buffer type on 150 mg/ml secukinumab liquid in syringe stability: parameter estimates for AP-SEC (%) after freeze-thaw stress (A), AP-SEC (%) after shaking stress (B), pre-main peak species by RP-HPLC (%) after 8 weeks storage at 25° C. (C), DP-SEC (%) after shaking stress (D)
Figure 16D:
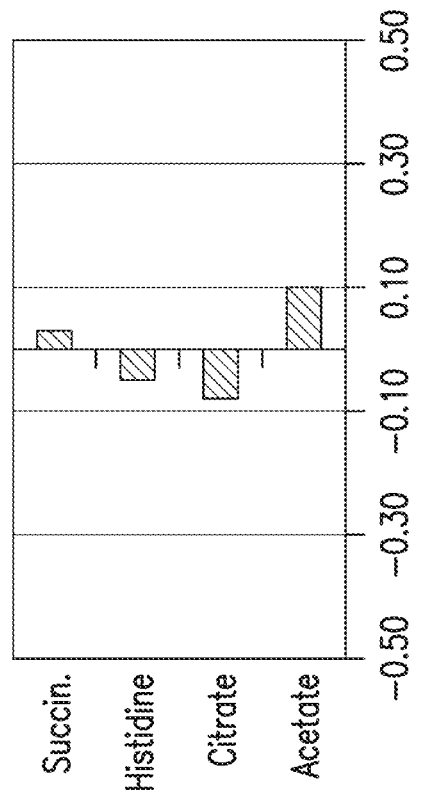
Figure 16A:
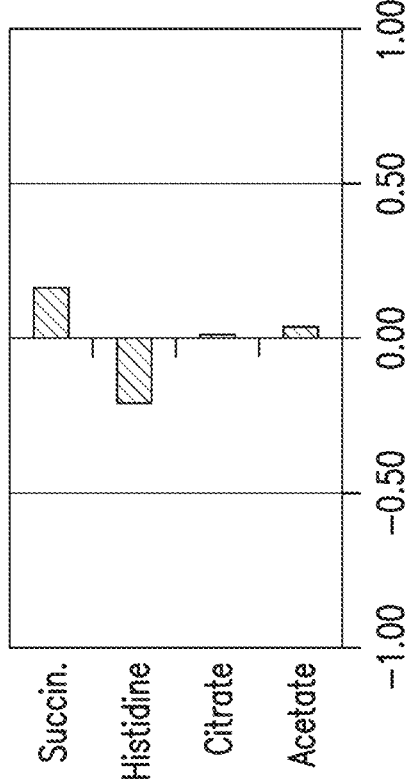
Figure 16C:
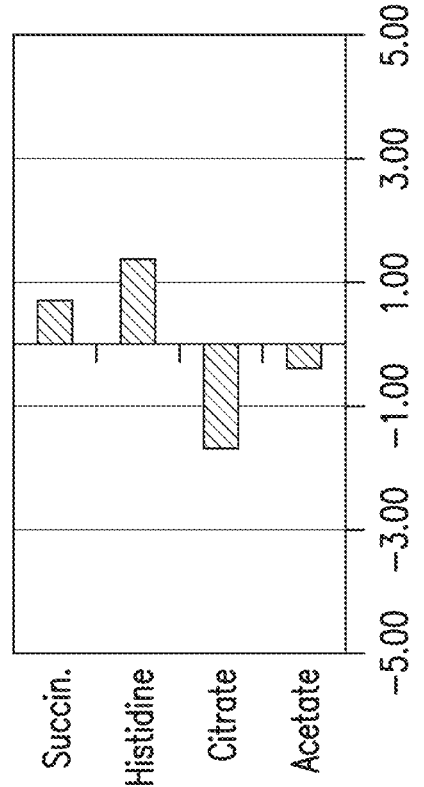

Based on the conclusions from the initial composition development studies, further studies were conducted in PFS using a DoE approach. The effect of surfactant (polysorbate 20, polysorbate 80, Poloxamer 188, none) was evaluated. The compositions were filled in PFS and placed on a 2 months stability study at long-term, accelerated and stressed conditions and were evaluated with regards to physical stability (AP-SEC, DLS, turbidity, visible and sub-visible particles by light obscuration), chemical stability (purity by CEX, purity by RP-HPLC, color) and indicators of biological activity (activity by Cys-CEX, free SH-groups). In addition, freeze-thaw (5 cycles of −20° C. to room temperature) and shaking stress (150 rpm for one week) was applied to compositions filled in 2 mL vials. The presence of a surfactant was beneficial as observed by lower turbidity levels and visible and sub-visible particles by light obscuration counts. However, there was only a weak impact of the surfactant type (FIG. 15).

We next identified the ideal concentration of the surfactant group III (polysorbate 80 0.01-0.04 (w/v) %). Samples were filled in PFS and stored for up to three months at long-term, accelerated and stressed conditions. Secukinumab physical (AP-SEC, DLS, sub-visible particles by light obscuration, visible particles, turbidity) and chemical (purity by CEX, purity by RP-HPLC, color) stability as well as biological activity were monitored. No distinct effect of polysorbate 80 concentrations on secukinumab quality attributes was observed during quiescent storage (FIG. 3) as well as after 1 week of shaking at 150 rpm. Polydispersity by DLS and sub-visible particles by light obscuration were slightly increased at higher surfactant concentrations; therefore the concentration of polysorbate 80 was defined as 0.02%, in order to keep a safety margin for the lowest evaluated concentration.

Example 5: The Choice of Buffer has Little Influence on Stability

The effect of buffer species (citrate, histidine, succinate, acetate) was evaluated in PFS using a DOE-approach. The compositions were filled in PFS and placed on a 2 months stability study at long-term, accelerated and stressed conditions and were evaluated with regards to physical stability (AP-SEC, DLS, turbidity, visible and sub-visible particles by light obscuration), chemical stability (purity by CEX, purity by RP-HPLC, color) and indicators of biological activity (activity by CysCEX, free SH-groups). In addition, freeze-thaw (5 cycles of −20° C. to room temperature) and shaking stress (150 rpm for one week) was applied to compositions filled in 2 mL vials. No relevant impact of the buffer type was observed. FIG. 16 shows selected quality attributes.

Example 6: Antibody-Concentration in The Range Tested has Little Influence on Stability The effect of secukinumab concentration on liquid composition quality attributes was evaluated in a range of 124.5-175.5 mg/mL. Compositions also contained 200 mM trehalose, 5 mM L-methionine and 0.02% polysorbate 80 in a histidine buffer pH 5.8. Compositions were filled into PFS and stored under long-term and accelerated conditions for 6 months. Relevant secukinumab quality attributes (purity by SEC, purity by RP-HPLC; purity by CEX, free SH-groups, biological activity, sub-visible particles by light obscuration, visible particles, turbidity and color of the solution) were monitored after 3 and 6 months storage. No relevant impact of secukinumab concentration on liquid composition quality attributes was observed within the range of 25 mg/ml to 150 mg/ml (data not shown).

Part 3—Properties of a Preferred Final Market Composition

A preferred pharmaceutical product of secukinumab comprises a liquid composition of 150 mg/ml secukinumab in 20 mM histidine buffer, pH 5.8, 200 mM trehalose, 0.02% polysorbate 80 and 5 mM L-methionine, which is provided in PFS. At initial fill and finish, the headspace in the PFS has an oxygen content of less than 12%. These pharmaceutical products have excellent shelf life and overall stability.

Stability testing of various batches of the secukinumab drug product (150 mg/ml secukinumab, 200 mM trehalose dihydrate, 20 mM L-histidine/L-histidine hydrochloride monohydrate, 5 mM L-methionine, 0.02% polysorbate 80 (% w/v), pH 5.8) in PFS was performed. Results of testing under long term storage conditions (2-8° C.) up to 24 months of storage, under accelerated storage conditions (25° C.) up to 6 months storage, and under temperature stressed conditions (30° C.) up to 6 months of storage months are shown in Tables 9-11, below. Based on the stability data presented, up to 24 months real time data for secukinumab 150 mg/1 ml Liquid in pre-filled syringe (PFS) and up to 36 months stability data generated during development (bulk-syringe), a shelf life of 24 months is proposed for secukinumab 150 mg/1 ml liquid in PFS commercial product when stored at long term conditions of 5° C.±3° C., protected from light and preventing from freezing.

TABLE 9

Purity by SEC, CEX and RP-HPLC.

| | | Purity by SEC | | | Purity by CEX | | | Purity by RP-HPLC | |
| --- | --- | --- | --- | --- | --- | --- | --- | --- | --- |
| | | | | | | Sum of | Sum of | | Sum of |
| | | | | | | | | | pre- main |
| | | Purity/ | AP- | DP- | Main | basic | acidic | Main | peak |
| | | Monomer | SEC | SEC | variant | variants | variants | variant | species |
| Storage conditions | | [%] | [%] | [%] | [%] | [%] | [%] | [%] | [%] |
| | Initial analysis | 99.1 | 0.90 | <0.10 | 78.2 | 11.3 | 10.5 | 88.7 | 2.2 |
| −20° C. | 1.5 months | 99.0 | 0.92 | <0.10 | 77.5 | 11.8 | 10.6 | 89.4 | 1.8 |
| 5° C. ± 3° C. | 1.5 months | 99.0 | 0.96 | <0.10 | 77.2 | 12.0 | 10.7 | 89.4 | 1.9 |
| | 3 months | 98.7 | 1.0 | 0.20 | 77.5 | 12.1 | 10.3 | 88.7 | 1.9 |
| | 6 months | 98.8 | 1.1 | <0.10 | 77.5 | 11.5 | 10.9 | 86.5 | 4.1* |
| | 9 months | 98.7 | 1.2 | 0.10 | 76.7 | 12.4 | 10.8 | 88.2 | 2.1 |
| | 12 months | 98.5 | 1.3 | 0.16 | 76.4 | 12.6 | 10.9 | 88.6 | 3.0 |
| | 18 months | 98.2 | 1.3 | 0.43 | 73.8 | 14.7 | 11.5 | 84.8 | 6.8* |
| | 24 months | 97.9 | 1.4 | 0.56 | 76.5 | 11.5 | 11.9 | 87.3 | 4.3 |
| 25° C./60% RH | 1.5 months | 98.6 | 1.2 | 0.14 | 72.3 | 14.6 | 12.7 | 87.9 | 3.8 |
| | 3 months | 97.5 | 1.6 | 0.83 | 68.6 | 15.9 | 15.4 | 81.1 | 9.9 |
| | 6 months | 96.2 | 2.0 | 1.7 | 62.8 | 16.2 | 21.0 | 76.1 | 15.3 |
| 30° C./75% RH | 1.5 months | 97.6 | 1.5 | 0.90 | 67.9 | 16.4 | 15.5 | 86.7 | 5.1 |
| | 3 months | 96.5 | 2.0 | 1.4 | 60.9 | 17.2 | 21.8 | 77.1 | 14.0 |
| | 6 months | 94.1 | 3.0 | 2.8 | 50.6 | 17.4 | 31.9 | 60.3 | 22.0 |

*This higher value is related to the appearance of a small peak just before the main peak. As this new peak is integrated separately from the main peak, the sum of variants before main peak becomes higher.

TABLE 10

Purity by CE-SDS (non-reducing) and Impurities by SDS-PAGE (reducing).

| Storage conditions | | Purity by CE-SDS (non-reducing) Purity/Monomer [%] | Impurity by SDS-PAGE (reducing) Sum of impurities [%] |
|---|---|---|---|
| | Initial analysis | 97.5 | 0.60 |
| −20° C. | 1.5 months | 97.3 | 0.92 |
| 5° C. ± 3° C. | 1.5 months | 97.2 | 0.91 |
| | 3 months | 97.4 | 0.63 |
| | 6 months | 97.4 | 0.57 |
| | 9 months | 97.5 | 0.66 |
| | 12 months | 97.4 | 0.58 |
| | 18 months | 97.1 | 0.63 |
| | 24 months | 97.2 | 0.61 |
| 25° C./60% RH | 1.5 months | 97.1 | 1.3 |
| | 3 months | 96.7 | 0.86 |
| | 6 months | 95.3 | 1.1 |
| 30° C./75% RH | 1.5 months | 96.8 | 1.1 |
| | 3 months | 95.6 | 1.3 |
| | 6 months | 94.0 | 1.9 |

TABLE 11

Potency and quantity.

| Storage conditions | | Inhibition of IL-16 from C-20/A4 chondrocytes [%] Potency [%] | Assay of protein by UV absorption Quantity [mg/mL] |
|---|---|---|---|
| | Initial analysis | 107 | 147.9 |
| −20° C. | 1.5 months | 107 | 149.6 |
| 5° C. ± 3° C. | 1.5 months | 92 | 149.4 |
| | 3 months | 92* | 149.5 |
| | 6 months | 102* | 149.6 |
| | 9 months | 103 | 149.5 |
| | 12 months | 90* | 149.0 |
| | 18 months | 88 | 147.9 |
| | 24 months | 98 | 149.4 |
| 25° C./60% RH | 1.5 months | 100 | 149.4 |
| | 3 months | 107* | 149.7 |
| | 6 months | 94* | 149.6 |
| 30° C./75% RH | 1.5 months | 90 | 149.1 |
| | 3 months | 119* | 149.3 |
| | 6 months | 85* | 149.4 |

*samples were tested >30 days after pull date, this deviation has no impact on potency assay results.

---

What is claimed is:

1. A stable liquid pharmaceutical composition comprising:
   (a) about 25 mg/mL to about 175 mg/mL secukinumab;
   (b) at least 2.5 mM methionine;
   (c) a buffer;
   (d) a non-ionic stabilizer; and
   (e) a surfactant;
   wherein the composition has a pH of about 5.2 to about 6.2.

2. The composition of claim 1, wherein the secukinumab is at a concentration of about 75 mg/mL to about 150 mg/mL.

3. The composition of claim 1, wherein:
   (a) the buffer is gluconate, histidine, citrate, phosphate, succinate, acetate, Tris, glycine, arginine, or a combination thereof;
   (b) the non-ionic stabilizer is mannitol, trehalose, raffinose, maltose, sorbitol, or a combination thereof; or
   (c) the surfactant is a polysorbate, a poloxamer, or a combination thereof.

4. The composition of claim 1, wherein:
   (a) the buffer is gluconate, histidine, citrate, phosphate, succinate, acetate, Tris, glycine, arginine, or a combination thereof;
   (b) the non-ionic stabilizer is mannitol, trehalose, raffinose, maltose, sorbitol, or a combination thereof; and
   (c) the surfactant is a polysorbate, a poloxamer, or a combination thereof.

5. The composition of claim 4, wherein:
   (a) the buffer is at a concentration of 10 mM to 30 mM;
   (b) the non-ionic stabilizer is at a concentration of about 175 mM to about 350 mM; and
   (c) the surfactant is at a concentration of 0.01% (w/v) to 0.04% (w/v).

6. The composition of claim 5, wherein:
   (a) the buffer comprises citrate;
   (b) the non-ionic stabilizer is sorbitol; and
   (c) the surfactant is polysorbate.

7. The composition of claim 1, wherein upon storage at 2-8° C. for about 24 months:
   (a) no more than 10% of secukinumab monomer is degraded as measured by size exclusion chromatography (SEC);
   (b) no more than 10% of secukinumab main variant is degraded as measured by cation exchange chromatography (CEX); or
   (c) no more than 10% of secukinumab main variant is degraded as measured by reverse phase-high performance liquid chromatography (RP-HPLC).

8. The composition of claim 1, wherein upon storage at 2-8° C. for about 24 months:
   (a) no more than 10% of secukinumab monomer is degraded as measured by size exclusion chromatography (SEC);

(b) no more than 10% of secukinumab main variant is degraded as measured by cation exchange chromatography (CEX); and
(c) no more than 10% of secukinumab main variant is degraded as measured by reverse phase-high performance liquid chromatography (RP-HPLC).

9. The composition of claim 1, wherein upon storage at 25° C. for about 6 months:
(a) no more than 10% of secukinumab monomer is degraded as measured by size exclusion chromatography (SEC);
(b) no more than 10% of secukinumab main variant is degraded as measured by cation exchange chromatography (CEX); or
(c) no more than 10% of secukinumab main variant is degraded as measured by reverse phase-high performance liquid chromatography (RP-HPLC).

10. The composition of claim 1, wherein upon storage at 25° C. for about 6 months:
(a) no more than 10% of secukinumab monomer is degraded as measured by size exclusion chromatography (SEC);
(b) no more than 10% of secukinumab main variant is degraded as measured by cation exchange chromatography (CEX); and
(c) no more than 10% of secukinumab main variant is degraded as measured by reverse phase-high performance liquid chromatography (RP-HPLC).

11. The composition of claim 7, wherein the relative biological activity of secukinumab in the composition is at least 80% of a reference standard as measured by the inhibition of interleukin-6 (IL-6) release from human chondrocytes upon storage at 2-8° C. for about 24 months.

12. The composition of claim 8, wherein the relative biological activity of secukinumab in the composition is at least 80% of a reference standard as measured by the inhibition of interleukin-6 (IL-6) release from human chondrocytes upon storage at 2-8° C. for about 24 months.

13. A liquid pharmaceutical composition comprising:
(a) about 25 mg/mL to about 175 mg/mL secukinumab;
(b) at least 2.5 mM methionine;
(c) a buffer;
(d) a non-ionic stabilizer; and
(e) a surfactant;
wherein the composition has a pH of 5.2 to 6.2; and
wherein no more than 10% of secukinumab monomer is degraded as measured by SEC upon storage at 2-8° C. for about 24 months.

14. The composition of claim 13, wherein secukinumab is at a concentration of about 75 mg/mL to about 150 mg/mL.

15. The composition of claim 13, wherein:
(a) the buffer is gluconate, histidine, citrate, phosphate, succinate, acetate, Tris, glycine, arginine, or a combination thereof;
(b) the non-ionic stabilizer is mannitol, trehalose, raffinose, maltose, sorbitol, or a combination thereof; and
(c) the surfactant is a polysorbate, a poloxamer, or a combination thereof.

16. The composition of claim 15, wherein:
(a) the buffer is at a concentration of 10 mM to 30 mM;
(b) the non-ionic stabilizer is at a concentration of about 175 mM to about 350 mM; and
(c) the surfactant is at a concentration of 0.01% (w/v) to 0.04% (w/v).

17. The composition of claim 13, wherein the relative biological activity of secukinumab in the composition is at least 80% of a reference standard as measured by the inhibition of interleukin-6 (IL-6) release from human chondrocytes upon storage at 2-8° C. for about 24 months.

18. A liquid pharmaceutical composition comprising:
(a) about 25 mg/mL to about 175 mg/mL secukinumab;
(b) at least 2.5 mM methionine;
(c) a buffer;
(d) a non-ionic stabilizer; and
(e) a surfactant;
wherein the composition has a pH of 5.2 to 6.2; and
wherein no more than 10% of secukinumab main variant is degraded as measured by CEX upon storage at 2-8° C. for about 24 months.

19. The composition of claim 18, wherein secukinumab is at a concentration of about 75 mg/mL to about 150 mg/mL.

20. The composition of claim 18, wherein:
(a) the buffer is gluconate, histidine, citrate, phosphate, succinate, acetate, Tris, glycine, arginine, or a combination thereof;
(b) the non-ionic stabilizer is mannitol, trehalose, raffinose, maltose, sorbitol, or a combination thereof; and
(c) the surfactant is a polysorbate, a poloxamer, or a combination thereof.

21. The composition of claim 20, wherein:
(a) the buffer is at a concentration of 10 mM to 30 mM;
(b) the non-ionic stabilizer is at a concentration of about 175 mM to about 350 mM; and
(c) the surfactant is at a concentration of 0.01% (w/v) to 0.04% (w/v).

22. The composition of claim 18, wherein the relative biological activity of secukinumab in the composition is at least 80% of a reference standard as measured by the inhibition of interleukin-6 (IL-6) release from human chondrocytes upon storage at 2-8° C. for about 24 months.

23. A liquid pharmaceutical composition comprising:
(a) about 25 mg/mL to about 175 mg/mL secukinumab;
(b) at least 2.5 mM methionine;
(c) a buffer;
(d) a non-ionic stabilizer; and
(e) a surfactant;
wherein the composition has a pH of 5.2 to 6.2; and
wherein no more than 10% of secukinumab main variant is degraded as measured by RP-HPLC upon storage at 2-8° C. for about 24 months.

24. The composition of claim 23, wherein secukinumab is at a concentration of about 75 mg/mL to about 150 mg/mL.

25. The composition of claim 23, wherein:
(a) the buffer is gluconate, histidine, citrate, phosphate, succinate, acetate, Tris, glycine, arginine, or a combination thereof;
(b) the non-ionic stabilizer is mannitol, trehalose, raffinose, maltose, sorbitol, or a combination thereof; and
(c) the surfactant is a polysorbate, a poloxamer, or a combination thereof.

26. The composition of claim 25, wherein:
(a) the buffer is at a concentration of 10 mM to 30 mM;
(b) the non-ionic stabilizer is at a concentration of about 175 mM to about 350 mM; and
(c) the surfactant is at a concentration of 0.01% (w/v) to 0.04% (w/v).

27. The composition of claim 23, wherein the relative biological activity of secukinumab in the composition is at least 80% of a reference standard as measured by the inhibition of interleukin-6 (IL-6) release from human chondrocytes upon storage at 2-8° C. for about 24 months.

28. The liquid composition of claim 23, wherein no more than 10% of secukinumab monomer is degraded as measured by size exclusion chromatography (SEC) upon storage at 25° C. for about 6 months.

29. The composition of claim 28, wherein:
(a) the buffer is gluconate, histidine, citrate, phosphate, succinate, acetate, Tris, glycine, arginine, or a combination thereof;
(b) the non-ionic stabilizer is mannitol, trehalose, raffinose, maltose, sorbitol, or a combination thereof; and
(c) the surfactant is a polysorbate, a poloxamer, or a combination thereof.

30. The composition of claim 29, wherein:
(a) secukinumab is at a concentration of about 75 mg/mL to about 150 mg/mL;
(b) the buffer is at a concentration of 10 mM to 30 mM;
(c) the non-ionic stabilizer is at a concentration of about 175 mM to about 350 mM; and
(d) the surfactant is at a concentration of 0.01% (w/v) to 0.04% (w/v).

31. The composition of claim 2, wherein the secukinumab is at a concentration of about 150 mg/mL and the methionine is at a concentration of 2.5 mM to about 134 mM.

32. The composition of claim 6, wherein the secukinumab is at a concentration of about 150 mg/mL and the methionine is at a concentration of 2.5 mM to about 134 mM.

33. The composition of claim 14, wherein the secukinumab is at a concentration of about 150 mg/mL and the methionine is at a concentration of 2.5 mM to about 134 mM.

34. The composition of claim 19, wherein the secukinumab is at a concentration of about 150 mg/mL and the methionine is at a concentration of 2.5 mM to about 134 mM.

35. The composition of claim 24, wherein the secukinumab is at a concentration of about 150 mg/mL and the methionine is at a concentration of 2.5 mM to about 134 mM.

36. The composition of claim 1, wherein the methionine is at a concentration of 2.5 mM to about 134 mM.

37. The composition of claim 13, 18, or 23, wherein the methionine is at a concentration of 2.5 mM to about 134 mM.

38. A pharmaceutical product comprising a container and the composition of claim 34 disposed within the container, wherein the product is a syringe or an autoinjector.

* * * * *